(12) United States Patent
Potyrailo et al.

(10) Patent No.: US 10,914,698 B2
(45) Date of Patent: Feb. 9, 2021

(54) SENSING METHOD AND SYSTEM

(71) Applicant: General Electric Company, Schenectady, NY (US)

(72) Inventors: Radislav Alexandrovich Potyrailo, Niskayuna, NY (US); Igor Tokarev, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 231 days.

(21) Appl. No.: 14/585,690

(22) Filed: Dec. 30, 2014

(65) Prior Publication Data

US 2015/0115983 A1  Apr. 30, 2015

Related U.S. Application Data

(63) Continuation-in-part of application No. 11/560,476, filed on Nov. 16, 2006, now Pat. No. 9,589,686, and a continuation-in-part of application No. 12/325,653, filed on Dec. 1, 2008, now abandoned, and a continuation-in-part of application No. 12/824,436, filed on Jun. 28, 2010, now abandoned, and a continuation-in-part of application No. 12/827,623, filed on Jun. 30, 2010, now Pat. No. 8,936,191, and a continuation-in-part of application No. 12/977,568, filed on Dec. 23, 2010, now abandoned, and a continuation-in-part of application No. 13/331,003, filed on Dec. 20, 2011, now Pat. No. 9,045,973, and (Continued)

(51) Int. Cl.
*G01N 27/12* (2006.01)
*G01N 33/18* (2006.01)

(52) U.S. Cl.
CPC ....... *G01N 27/126* (2013.01); *G01N 33/1893* (2013.01)

(58) Field of Classification Search
CPC .................. G01N 27/126; G01N 33/1893
See application file for complete search history.

(56) References Cited

U.S. PATENT DOCUMENTS

| D218,009 S | 7/1970 | Bosack |
|---|---|---|
| D219,617 S | 12/1970 | Swift |

(Continued)

FOREIGN PATENT DOCUMENTS

| CN | 1363844 A | 8/2002 |
|---|---|---|
| CN | 1532372 A | 9/2004 |

(Continued)

OTHER PUBLICATIONS

Dervos, Constantine T., et al. "A complex permittivity based sensor for the electrical characterization of high-voltage transformer oils." Sensors 5.4 (2005): 302-316.*

(Continued)

*Primary Examiner* — Robert J Eom
(74) *Attorney, Agent, or Firm* — Armstrong Teasdale LLP

(57) ABSTRACT

A system that includes a sensor for measuring a resonant impedance spectral response of an inductor-capacitor-resistor (LCR) resonator and correlating the measured response of one or more spectral parameters to one or more characteristics of the fluid. Such characteristics may be the age or health of the fluid and/or the identification of and concentration of components in the fluid.

23 Claims, 23 Drawing Sheets

Related U.S. Application Data a continuation-in-part of application No. 13/484,674, filed on May 31, 2012, now Pat. No. 9,052,263, which is a continuation-in-part of application No. 12/424,016, filed on Apr. 15, 2009, now Pat. No. 8,364,419, application No. 14/585,690, which is a continuation-in-part of application No. 13/538,570, filed on Jun. 29, 2012, now Pat. No. 9,538,657, and a continuation-in-part of application No. 13/558,499, filed on Jul. 26, 2012, now Pat. No. 9,195,925, and a continuation-in-part of application No. 13/630,939, filed on Sep. 28, 2012, now Pat. No. 9,389,260, and a continuation-in-part of application No. 13/630,954, filed on Sep. 28, 2012, now Pat. No. 9,147,144, and a continuation-in-part of application No. 13/630,587, filed on Sep. 28, 2012, now Pat. No. 9,658,178, and a continuation-in-part of application No. 13/630,739, filed on Sep. 28, 2012, now Pat. No. 9,176,083, and a continuation-in-part of application No. 13/729,800, filed on Dec. 28, 2012, now Pat. No. 9,097,639, and a continuation-in-part of application No. 13/729,851, filed on Dec. 28, 2012, now Pat. No. 9,261,474, and a continuation-in-part of application No. 13/838,884, filed on Mar. 15, 2013, now Pat. No. 9,389,296, and a continuation-in-part of application No. 14/031,951, filed on Sep. 19, 2013, now Pat. No. 9,037,418, and a continuation-in-part of application No. 14/031,965, filed on Sep. 19, 2013, now Pat. No. 8,990,025, and a continuation-in-part of application No. 14/532,168, filed on Nov. 4, 2014, now Pat. No. 9,536,122.

(60) Provisional application No. 61/987,853, filed on May 2, 2014.

(56) References Cited

U.S. PATENT DOCUMENTS

| | | | |
|---|---|---|---|
| 3,675,121 | A | 7/1972 | Thompson |
| 3,778,706 | A | 12/1973 | Thompson |
| 3,927,369 | A | 12/1975 | Billeter et al. |
| 4,096,385 | A | 6/1978 | Marett |
| 4,273,636 | A | 6/1981 | Shimada et al. |
| 4,275,364 | A | 6/1981 | Skatvold |
| 4,372,164 | A | 2/1983 | Brown et al. |
| 4,553,434 | A | 11/1985 | Spaargaren |
| 4,728,892 | A | 3/1988 | Vinegar et al. |
| 4,820,989 | A | 4/1989 | Vail, III |
| 4,844,097 | A | 7/1989 | Bellhouse et al. |
| 4,876,512 | A | 10/1989 | Kroeger et al. |
| 4,882,542 | A | 11/1989 | Vail, III |
| 4,887,455 | A | 12/1989 | Payne et al. |
| 4,887,798 | A | 12/1989 | Julius |
| 4,922,745 | A | 5/1990 | Rudkin et al. |
| 4,941,958 | A | 7/1990 | Byers |
| 4,965,522 | A | 10/1990 | Hazen et al. |
| 4,996,490 | A | 2/1991 | Scott et al. |
| 5,010,301 | A | 4/1991 | Leung et al. |
| 5,025,346 | A | 6/1991 | Tang et al. |
| 5,059,790 | A | 10/1991 | Klainer et al. |
| 5,089,780 | A | 2/1992 | Megerle |
| 5,157,338 | A | 10/1992 | Motherbaugh et al. |
| 5,208,165 | A | 5/1993 | Law et al. |
| 5,241,364 | A | 11/1993 | Kimura |
| 5,260,569 | A | 11/1993 | Kimura |
| 5,306,644 | A | 4/1994 | Myerholtz et al. |
| 5,344,547 | A | 9/1994 | Vlasov et al. |
| 5,421,983 | A | 6/1995 | Slack et al. |
| 5,443,985 | A | 8/1995 | Lu et al. |
| 5,497,140 | A | 3/1996 | Tuttle |
| 5,543,722 | A | 8/1996 | Suzuki et al. |
| 5,591,896 | A | 1/1997 | Lin |
| 5,592,040 | A | 1/1997 | Yamamoto |
| 5,607,566 | A | 3/1997 | Brown et al. |
| 5,646,592 | A | 7/1997 | Tuttle |
| 5,672,319 | A | 9/1997 | Eisum |
| 5,744,902 | A | 4/1998 | Vig |
| 5,751,475 | A | 5/1998 | Ishiwata et al. |
| 5,754,055 | A | 5/1998 | McAdoo et al. |
| 5,785,181 | A | 7/1998 | Quartararo, Jr. |
| 5,786,595 | A | 7/1998 | Herron et al. |
| 5,817,943 | A | 10/1998 | Welles, II et al. |
| 5,831,439 | A | 11/1998 | Suenram et al. |
| 5,840,168 | A | 11/1998 | Chaniotakis et al. |
| 5,874,047 | A | 2/1999 | Schoening et al. |
| 5,961,923 | A | 10/1999 | Nova et al. |
| 5,997,817 | A | 12/1999 | Crismore et al. |
| 6,025,725 | A | 2/2000 | Gershenfeld et al. |
| 6,025,783 | A | 2/2000 | Steffens, Jr. |
| 6,107,924 | A | 8/2000 | Kasai et al. |
| 6,111,520 | A | 8/2000 | Allen et al. |
| 6,166,546 | A | 12/2000 | Scheihing et al. |
| 6,189,656 | B1 | 2/2001 | Morgenstern et al. |
| 6,192,753 | B1 | 2/2001 | Czarnek |
| 6,204,764 | B1 | 3/2001 | Maloney |
| 6,278,379 | B1 | 8/2001 | Allen et al. |
| 6,287,765 | B1 | 9/2001 | Cubicciotti |
| 6,359,444 | B1 | 3/2002 | Grimes |
| 6,360,585 | B1 | 3/2002 | Potyrailo et al. |
| 6,398,931 | B1 | 6/2002 | Burchette et al. |
| 6,399,375 | B2 | 6/2002 | Vajta |
| 6,406,668 | B1 | 6/2002 | Dordick et al. |
| 6,461,872 | B1 | 10/2002 | Sivavec |
| 6,471,838 | B1 | 10/2002 | Igel et al. |
| 6,506,346 | B1 | 1/2003 | Monro |
| 6,532,834 | B1 | 3/2003 | Pinto et al. |
| 6,544,193 | B2 | 4/2003 | Abreu |
| 6,586,946 | B2 | 7/2003 | Hefti et al. |
| 6,614,229 | B1 | 9/2003 | Clark et al. |
| 6,657,429 | B1 | 12/2003 | Goldfine et al. |
| 6,672,512 | B2 | 1/2004 | Bridgelall |
| 6,676,903 | B2 | 1/2004 | Potyrailo |
| 6,730,201 | B1 | 5/2004 | Kuhlman et al. |
| 6,751,557 | B1 | 6/2004 | Shehab et al. |
| 6,771,074 | B2 | 8/2004 | Zou et al. |
| 6,773,926 | B1 | 8/2004 | Freund et al. |
| 6,780,307 | B2 | 8/2004 | Kidwell |
| 6,782,736 | B1 | 8/2004 | Hammer |
| 6,804,544 | B2 | 10/2004 | Van Antwerp et al. |
| 6,818,450 | B2 | 11/2004 | Eaton et al. |
| 6,864,801 | B2 | 3/2005 | Tabanou et al. |
| 6,891,383 | B2 | 5/2005 | Nicholson et al. |
| 6,911,818 | B2 | 6/2005 | Julius |
| 6,953,520 | B2 | 10/2005 | Yengoyan et al. |
| 7,017,404 | B1 | 3/2006 | Kain |
| 7,031,560 | B2 | 4/2006 | Lelong-Feneyrou et al. |
| 7,034,660 | B2 | 4/2006 | Watters et al. |
| 7,038,470 | B1 | 5/2006 | Johnson |
| 7,040,139 | B2 | 5/2006 | Sunshine |
| 7,076,858 | B2 | 7/2006 | Eckstein et al. |
| 7,089,099 | B2 | 8/2006 | Shostak et al. |
| 7,109,859 | B2 | 9/2006 | Peeters |
| 7,113,125 | B2 | 9/2006 | Le Sesne |
| 7,125,382 | B2 | 10/2006 | Zhou et al. |
| 7,126,013 | B2 | 10/2006 | Heeney et al. |
| 7,168,310 | B2 | 1/2007 | Al-Ruwaili |
| 7,171,312 | B2 | 1/2007 | Steinthal et al. |
| 7,178,416 | B2 | 2/2007 | Whelan et al. |
| 7,204,128 | B1 | 4/2007 | Liu et al. |
| 7,252,010 | B2 | 8/2007 | Ohta et al. |
| 7,276,916 | B2 | 10/2007 | Hammer |
| 7,293,450 | B2 | 11/2007 | Liu et al. |
| 7,317,989 | B2 | 1/2008 | DiFoggio et al. |
| 7,335,336 | B1 | 2/2008 | Kim |
| 7,343,800 | B2 | 3/2008 | Harman et al. |
| 7,350,367 | B2 | 4/2008 | Matsiev et al. |
| 7,434,457 | B2 | 10/2008 | Goodwin et al. |
| 7,445,143 | B2 | 11/2008 | Pang et al. |
| 7,449,893 | B1 | 11/2008 | Tsironis |
| 7,455,108 | B2 | 11/2008 | Jenkins et al. |
| 7,456,744 | B2 | 11/2008 | Kuhns |

(56) References Cited

U.S. PATENT DOCUMENTS

| | | |
|---|---|---|
| 7,466,041 B2 | 12/2008 | Urman |
| 7,481,771 B2 | 1/2009 | Fonseca et al. |
| 7,483,743 B2 | 1/2009 | Mann et al. |
| 7,486,495 B1 | 2/2009 | Diederichs et al. |
| 7,495,454 B2 | 2/2009 | Rivera |
| 7,523,647 B2 | 4/2009 | Scott |
| 7,562,557 B2 | 7/2009 | Bennett et al. |
| 7,569,810 B1 | 8/2009 | Troxler et al. |
| 7,629,167 B2 | 12/2009 | Hodge et al. |
| 7,677,307 B2 | 3/2010 | Vasques et al. |
| 7,691,329 B2 | 4/2010 | Potyrailo et al. |
| 7,697,574 B2 | 4/2010 | Suematsu et al. |
| 7,808,235 B2 | 10/2010 | Rollins et al. |
| 7,812,609 B2 | 10/2010 | Martinez et al. |
| 7,814,786 B2 | 10/2010 | Woodard |
| 7,948,380 B2 | 5/2011 | Kuhns et al. |
| 7,948,385 B2 | 5/2011 | Potyrailo et al. |
| 7,958,772 B2 | 6/2011 | Permuy et al. |
| 7,969,307 B2 | 6/2011 | Peeters |
| 8,018,342 B2 | 9/2011 | Monk et al. |
| 8,063,648 B2 | 11/2011 | Nilsson et al. |
| 8,111,143 B2 | 2/2012 | Tong et al. |
| 8,154,389 B2 | 4/2012 | Rowland et al. |
| 8,155,891 B2 | 4/2012 | Kong et al. |
| 8,159,347 B2 | 4/2012 | Potyrailo et al. |
| 8,184,290 B2 | 5/2012 | Hertens et al. |
| 8,190,394 B2 | 5/2012 | Davis et al. |
| 8,215,166 B2 | 7/2012 | Cunningham et al. |
| 8,232,091 B2 | 7/2012 | Maltezos et al. |
| 8,246,910 B2 | 8/2012 | Dhirani et al. |
| 8,261,618 B2 | 9/2012 | Engle et al. |
| 8,318,099 B2 | 11/2012 | Potyrailo et al. |
| 8,342,242 B2 | 1/2013 | Roddy et al. |
| 8,429,985 B2 | 4/2013 | Furlong |
| 8,452,716 B2 | 5/2013 | Howley et al. |
| 8,468,871 B2 | 6/2013 | Potyrailo et al. |
| 8,508,368 B2 | 8/2013 | Potyrailo et al. |
| 8,547,110 B2 | 10/2013 | Kesil et al. |
| 8,643,388 B2 | 2/2014 | Hedges |
| 8,676,436 B2 | 3/2014 | Raimarckers et al. |
| 8,710,973 B2 | 4/2014 | Schneider et al. |
| 8,732,938 B2 | 5/2014 | Kolosov et al. |
| 8,736,425 B2 | 5/2014 | Potyrailo |
| 8,833,145 B2 | 9/2014 | Fischer et al. |
| 8,933,706 B1 | 1/2015 | Karlquist |
| 8,952,708 B2 | 2/2015 | Nikolenko |
| 9,074,966 B2 | 7/2015 | Sanderlin et al. |
| 9,176,083 B2 | 11/2015 | Surman et al. |
| 9,536,122 B2 | 1/2017 | Potyrailo |
| 2001/0045355 A1 | 11/2001 | Gephart et al. |
| 2002/0050929 A1 | 5/2002 | Parrotta et al. |
| 2002/0081231 A1 | 6/2002 | Shapiro et al. |
| 2002/0089356 A1 | 7/2002 | Perrott et al. |
| 2002/0149466 A1 | 10/2002 | Sunshine et al. |
| 2002/0173040 A1 | 11/2002 | Potyrailo et al. |
| 2002/0177232 A1 | 11/2002 | Melker et al. |
| 2002/0197725 A1 | 12/2002 | Eaton et al. |
| 2003/0042149 A1 | 3/2003 | Smith et al. |
| 2003/0053936 A1 | 3/2003 | Potyrailo |
| 2003/0154031 A1 | 8/2003 | Potyrailo et al. |
| 2003/0179024 A1 | 9/2003 | Montagnana |
| 2003/0232223 A1 | 12/2003 | Leddy et al. |
| 2004/0051154 A1 | 3/2004 | Yamakawa et al. |
| 2004/0113790 A1 | 6/2004 | Hamel et al. |
| 2004/0125442 A1 | 7/2004 | Yun et al. |
| 2004/0155667 A1 | 8/2004 | Kesil et al. |
| 2004/0189487 A1 | 9/2004 | Hoefel et al. |
| 2004/0219523 A1 | 11/2004 | Stanton et al. |
| 2004/0227682 A1 | 11/2004 | Anderson |
| 2004/0248315 A1 | 12/2004 | Klein et al. |
| 2005/0004439 A1 | 1/2005 | Shin et al. |
| 2005/0022581 A1 | 2/2005 | Sunshine |
| 2005/0058460 A1 | 3/2005 | Wang |
| 2005/0087235 A1 | 4/2005 | Skorpik et al. |
| 2005/0088299 A1 | 4/2005 | Bandy et al. |
| 2005/0093760 A1 | 5/2005 | Rochelle et al. |
| 2005/0104790 A1 | 5/2005 | Duron |
| 2005/0130292 A1 | 6/2005 | Ahn et al. |
| 2005/0161405 A1 | 7/2005 | Holland |
| 2005/0193832 A1 | 9/2005 | Tombs et al. |
| 2005/0199731 A9 | 9/2005 | Empedocles et al. |
| 2006/0014172 A1 | 1/2006 | Muller et al. |
| 2006/0020427 A1 | 1/2006 | Kahn et al. |
| 2006/0055531 A1 | 3/2006 | Cook et al. |
| 2006/0081471 A1 | 4/2006 | Kidwell |
| 2006/0133720 A1 | 6/2006 | Hochberg et al. |
| 2006/0141469 A1 | 6/2006 | Rossier et al. |
| 2006/0198760 A1 | 9/2006 | Potyrailo |
| 2006/0202821 A1 | 9/2006 | Cohen |
| 2006/0205093 A1 | 9/2006 | Prins |
| 2006/0210440 A1 | 9/2006 | Potyrailo |
| 2006/0238349 A1 | 10/2006 | Hu et al. |
| 2006/0265150 A1 | 11/2006 | Hu et al. |
| 2007/0029195 A1 | 2/2007 | Li et al. |
| 2007/0064839 A1 | 3/2007 | Luu |
| 2007/0072009 A1 | 3/2007 | Matsumoto et al. |
| 2007/0084277 A1 | 4/2007 | Steinsiek |
| 2007/0085686 A1 | 4/2007 | Oz |
| 2007/0090926 A1 | 4/2007 | Potyrailo et al. |
| 2007/0100666 A1 | 5/2007 | Stivoric et al. |
| 2007/0111222 A1 | 5/2007 | Chasin et al. |
| 2007/0131418 A1 | 6/2007 | Barrow et al. |
| 2007/0148670 A1 | 6/2007 | O'Malley |
| 2007/0176773 A1 | 8/2007 | Smolander et al. |
| 2007/0213684 A1 | 9/2007 | Hickle et al. |
| 2007/0215709 A1 | 9/2007 | Baude et al. |
| 2007/0222605 A1 | 9/2007 | Andresky |
| 2007/0236338 A1 | 10/2007 | Maruyama |
| 2007/0241890 A1 | 10/2007 | Yoshioka |
| 2008/0004904 A1 | 1/2008 | Tran |
| 2008/0024301 A1 | 1/2008 | Fritchie et al. |
| 2008/0033368 A1 | 2/2008 | Fago |
| 2008/0057526 A1 | 3/2008 | Caduff et al. |
| 2008/0093219 A1 | 4/2008 | Goldberg et al. |
| 2008/0116908 A1 | 5/2008 | Potyrailo et al. |
| 2008/0135614 A1 | 6/2008 | Werner et al. |
| 2008/0142366 A1 | 6/2008 | Tamirisa et al. |
| 2008/0157901 A1 | 7/2008 | Matekovits et al. |
| 2008/0177150 A1 | 7/2008 | Li et al. |
| 2008/0179197 A1 | 7/2008 | Wu |
| 2008/0180249 A1 | 7/2008 | Butler et al. |
| 2008/0184787 A1 | 8/2008 | Coates |
| 2008/0191859 A1 | 8/2008 | Tiek et al. |
| 2008/0236814 A1 | 10/2008 | Roddy |
| 2008/0280374 A1 | 11/2008 | Potyrailo et al. |
| 2009/0035856 A1 | 2/2009 | Galliher et al. |
| 2009/0039864 A1 | 2/2009 | Gordon |
| 2009/0087862 A1 | 4/2009 | Carter et al. |
| 2009/0095073 A1 | 4/2009 | Fukumura et al. |
| 2009/0104707 A1 | 4/2009 | Wang et al. |
| 2009/0120169 A1 | 5/2009 | Chandler et al. |
| 2009/0204250 A1 | 8/2009 | Potyrailo et al. |
| 2009/0215646 A1 | 8/2009 | Anslyn et al. |
| 2009/0256679 A1 | 10/2009 | Potyrailo et al. |
| 2009/0265037 A1 | 10/2009 | Bassa |
| 2009/0278685 A1 | 11/2009 | Potyrailo et al. |
| 2009/0289776 A1 | 11/2009 | Moore et al. |
| 2009/0308155 A1 | 12/2009 | Zhang |
| 2010/0021993 A1 | 1/2010 | Wang |
| 2010/0042338 A1 | 2/2010 | Giurgiutiu et al. |
| 2010/0059221 A1 | 3/2010 | Vannuffelen et al. |
| 2010/0075405 A1 | 3/2010 | Broadley |
| 2010/0102004 A1 | 4/2010 | Holland |
| 2010/0134257 A1 | 6/2010 | Puleston et al. |
| 2010/0134286 A1 | 6/2010 | Potyrailo |
| 2010/0138267 A1 | 6/2010 | Vittal et al. |
| 2010/0153323 A1 | 6/2010 | Hennessy et al. |
| 2010/0225482 A1 | 9/2010 | Kasai et al. |
| 2010/0231407 A1 | 9/2010 | Carr |
| 2010/0250170 A1 | 9/2010 | Kalinin et al. |
| 2010/0261226 A1 | 10/2010 | Niazi |
| 2010/0280788 A1 | 11/2010 | Bohan et al. |
| 2010/0295558 A1 | 11/2010 | Eberheim et al. |
| 2011/0006878 A1 | 1/2011 | Nyffeler et al. |

(56) References Cited

U.S. PATENT DOCUMENTS

| | | |
|---|---|---|
| 2011/0006900 A1 | 1/2011 | Nyffeler et al. |
| 2011/0012736 A1 | 1/2011 | Potyrailo et al. |
| 2011/0018649 A1 | 1/2011 | David et al. |
| 2011/0022318 A1 | 1/2011 | Zhao et al. |
| 2011/0029156 A1 | 2/2011 | Vernacchia et al. |
| 2011/0045601 A1 | 2/2011 | Gryska et al. |
| 2011/0051775 A1 | 3/2011 | Ivanov et al. |
| 2011/0101996 A1 | 5/2011 | Potyrailo |
| 2011/0117538 A1 | 5/2011 | Niazi |
| 2011/0152706 A1 | 6/2011 | Christopherson et al. |
| 2011/0152750 A1 | 6/2011 | Dacey, Jr. et al. |
| 2011/0156177 A1 | 6/2011 | Merz |
| 2011/0160681 A1 | 6/2011 | Dacey, Jr. et al. |
| 2011/0221667 A1 | 9/2011 | Lee |
| 2011/0248825 A1 | 10/2011 | Hamel et al. |
| 2011/0263036 A1 | 10/2011 | Blauw et al. |
| 2011/0282540 A1 | 11/2011 | Armitage et al. |
| 2011/0283821 A1 | 11/2011 | Ober et al. |
| 2011/0320142 A1 | 12/2011 | Surman |
| 2012/0001730 A1 | 1/2012 | Potyrailo et al. |
| 2012/0004851 A1 | 1/2012 | Potyrailo |
| 2012/0025526 A1 | 2/2012 | Luo et al. |
| 2012/0053881 A1 | 3/2012 | Schulz et al. |
| 2012/0116683 A1 | 5/2012 | Potyrailo et al. |
| 2012/0161787 A1 | 6/2012 | Potyrailo et al. |
| 2012/0166095 A1 | 6/2012 | Potyrailo |
| 2012/0206155 A1 | 8/2012 | Wang |
| 2012/0231504 A1 | 9/2012 | Niazi |
| 2012/0235690 A1 | 9/2012 | Potyrailo |
| 2012/0258441 A1 | 10/2012 | Gebauer et al. |
| 2012/0265036 A1 | 10/2012 | Estes et al. |
| 2012/0289757 A1 | 11/2012 | Boyden et al. |
| 2013/0041334 A1 | 2/2013 | Prioleau et al. |
| 2013/0060112 A1 | 3/2013 | Pryor et al. |
| 2013/0154847 A1 | 6/2013 | Potyrailo |
| 2013/0182819 A1 | 7/2013 | Dvorkin et al. |
| 2013/0285677 A1 | 10/2013 | Hammer |
| 2014/0002111 A1 | 1/2014 | Potyrailo et al. |
| 2014/0028330 A1 | 1/2014 | Potyrailo |
| 2014/0090454 A1 | 4/2014 | Surman et al. |
| 2014/0091811 A1 | 4/2014 | Potyrailo |
| 2014/0095102 A1 | 4/2014 | Potyrailo et al. |
| 2014/0182362 A1 | 7/2014 | Potyrailo et al. |
| 2014/0305194 A1 | 10/2014 | Surman et al. |
| 2015/0185173 A1 | 7/2015 | Potyrailo et al. |
| 2015/0233887 A1 | 8/2015 | Surman et al. |
| 2016/0187277 A1 | 6/2016 | Potyrailo et al. |

FOREIGN PATENT DOCUMENTS

| | | |
|---|---|---|
| CN | 2809215 Y | 8/2006 |
| CN | 1865966 A | 11/2006 |
| CN | 101022760 A | 8/2007 |
| CN | 101057124 A | 10/2007 |
| CN | 201000455 Y | 1/2008 |
| CN | 101218487 A | 7/2008 |
| CN | 101988574 A | 3/2011 |
| CN | 102022264 A | 4/2011 |
| CN | 102422330 A | 4/2012 |
| CN | 102612638 A | 7/2012 |
| CN | 203923208 U | 11/2014 |
| EP | 2498076 A1 | 9/2012 |
| GB | 193953 A | 4/1958 |
| JP | 5774097 A | 5/1982 |
| JP | 59116855 U | 8/1984 |
| JP | 59160746 A | 9/1984 |
| JP | 61112971 A | 5/1986 |
| JP | 0381659 A | 4/1991 |
| JP | 06160317 A | 6/1994 |
| JP | 6086057 U | 12/1994 |
| JP | 0773282 A | 3/1995 |
| JP | 07120423 A | 5/1995 |
| JP | 08509549 A | 10/1996 |
| JP | 06194333 A | 7/1997 |
| JP | 09292453 A | 11/1997 |
| JP | 10504388 A | 4/1998 |
| JP | 2000111547 A | 4/2000 |
| JP | 2001502791 A | 2/2001 |
| JP | 2002125206 A | 4/2002 |
| JP | 2003503011 A | 1/2003 |
| JP | 2003506706 A | 2/2003 |
| JP | 2003161637 A | 6/2003 |
| JP | 2005156569 A | 6/2005 |
| JP | 2005233976 A | 9/2005 |
| JP | 2006516721 A | 7/2006 |
| JP | 2007516509 A | 6/2007 |
| JP | 2007516814 A | 6/2007 |
| JP | 2008501448 A | 1/2008 |
| JP | 2008129009 A | 6/2008 |
| JP | 2008236617 A | 10/2008 |
| JP | 2008298565 A | 12/2008 |
| JP | 2009092633 A | 4/2009 |
| JP | 2009530908 A | 8/2009 |
| JP | 2009540292 A | 11/2009 |
| JP | 2011258627 A | 12/2011 |
| WO | 9845779 A1 | 10/1998 |
| WO | 0055583 A1 | 9/2000 |
| WO | 0060120 A2 | 9/2000 |
| WO | 0173380 A1 | 10/2001 |
| WO | 0212129 A1 | 2/2002 |
| WO | 0223176 A1 | 3/2002 |
| WO | 02095675 A1 | 11/2002 |
| WO | 03050529 A1 | 6/2003 |
| WO | 03098175 A1 | 11/2003 |
| WO | 2004032191 A2 | 4/2004 |
| WO | 2006131697 A2 | 12/2006 |
| WO | 2007072009 A2 | 6/2007 |
| WO | 2007075619 A1 | 7/2007 |
| WO | 2007101992 A1 | 9/2007 |
| WO | 2008082654 A2 | 7/2008 |
| WO | 2013057630 A1 | 4/2013 |
| WO | 2015090358 A1 | 6/2015 |
| WO | 2015128050 A1 | 9/2015 |

OTHER PUBLICATIONS

Zaretsky, Mark C., James R. Melcher, and Chathan M. Cooke. "Moisture sensing in transformer oil using thin-film microdielectrometry." IEEE Transactions on Electrical Insulation 24.6 (1989): 1167-1176.*

Wakamatsu, Hideki. "A dielectric spectrometer for liquid using the electromagnetic induction method." Hewlett Packard Journal 48 (1997): 37-44.*

Want, Roy. "Enabling ubiquitous sensing with RFID." Computer 37.4 (2004): 84-86.*

Dehennis, Andrew D., and Kensall D. Wise. "A wireless microsystem for the remote sensing of pressure, temperature, and relative humidity." Journal of Microelectromechanical Systems 14.1 (2005): 12-22. (Year: 2005).*

Heeger, "Semiconducting and Metallic Polymers: The Fourth Generation of Polymeric Materials", The Journal of Physical Chemistry B, vol. No.105, Issue No. 36, pp. 8475-8491, 2001.

Mourzina et al., "Development of Multisensor Systems based on Chalcogenide Thin Film Chemical Sensors for the Simulataneous Multicomponent Analysis of Metal Ions in Complex Solutions", Electrochimica Acta, vol. No. 47, Issue No. 1-2, pp. 251-258, Sep. 1, 2001.

Gawad et al., "Micromachined Impedance Spectroscopy Flow Cytometer for Cell Analysis and Particle Sizing", Lab on a Chip, vol. No. 1, Issue No. 1, pp. 76-82, Sep. 2001.

Akyildiz et al., "Wireless Sensor Networks: A survey", Computer Networks, vol. No. 38, pp. 393-422, 2002.

Harpster et al., "A Passive Humidity Monitoring System for In-Situ Remote Wireless Testing of Micropackages", Microelectromechanical System, vol. No. 11, Issue No. 1, pp. 61-67, 2002.

Haes et al., "A Nanoscale Optical Biosensor: Sensitivity and Selectivity of an Approach Based on the Localized Surface Plasmon Resonance Spectroscopy of Triangular Silver Nanoparticles", Journal of the American Chemical Society, vol. No. 124, Issue No. 35, pp. 10596-10604, 2002.

(56) References Cited

OTHER PUBLICATIONS

Janata et al., "Electrochemical Sensors and their Impedances: A Tutorial", Critical Reviews in Analytical Chemistry, vol. No. 32, Issue No. 2, pp. 109-120, 2002.
Ceresa et al., "Rational Design of Potentiometric Trace Level Ion Sensors. A Ag+-Selective Electrode with a 100 ppt Detection Limit", Analytical Chemistry, vol. No. 74, Issue No. 16, pp. 4027-4036, 2002.
Alary et al.,"Subsea Water Separation: A Cost-effective Solution for Ultra Deep Water Production", 17th World Petroleum Congress, Rio de Janeiro, Brazil, Sep. 1-5, 2002.
Butler et al., "Wireless, Passive, Resonant-Circuit, Inductively Coupled, Inductive Strain Sensor", Sensors and Actuators A: Physical, vol. No. 102, Issue No. 1, pp. 61-66, Dec. 1, 2002.
Johns et al., "Sensitive Indirect Photometric Detection of Inorganic and Small Organic Anions by Capillary Electrophoresis Using Orange G as a Probe Ion", Electrophoresis, vol. No. 24, Issue No. 3, pp. 557-566, Jan. 2003.
Fauveau et al., "Guided-Wave Radar helps Level-Detection in Harsh Settings Control Engineering", Control Engineering, vol. No. 50, Issue No. 3, pp. 16, Mar. 2003.
Grate et al., "Sorptive Behavior of Monolayer-Protected Gold Nanoparticle Films: Implications for Chemical Vapor Sensing", Analytical Chemistry, vol. No. 75, Issue No. 8, pp. 1868-1879, Apr. 15, 2003.
Grimes et al., "Resonance Sensors: A Critical Review Sensors", Analytical Chemistry, vol. No. 75, Issue No. 8, pp. 1868-1879, Apr. 15, 2003.
De Borba et al., "Determination of Sodium at Low Ng/L Concentrations in Simulated Power Plant Waters by Ion Chromatography", Journal of Chromatography, vol. No. 995, Issue No. 1-2, pp. 143-152, May 2, 2003.
Sakharov et al., "Liquid Level Sensor using Ultrasonic Lamb Waves", Ultrasonics, vol. No. 41, Issue No. 4, pp. 319-322, Jun. 2003.
Kumar et al., "Investigation into the Interaction between Surface-Bound Alkylamines and Gold Nanoparticles", Langmuir, vol. No. 19, Issue No. 15, pp. 6277-6282, 2003.
Potyrailo et al., "Fluorescence Spectroscopy and Multivariate Spectral Descriptor Analysis for High-Throughput Multiparameter Optimization of Polymerization Conditions of Combinatorial 96-Microreactor Arrays", Journal of Combinatorial Chemistry, vol. No. 5, Issue No. 1, pp. 8-17, 2003.
Mabic et al., "Quality Adjustment of Treated Water in an Experimental Detection", GIT Labor-Fachzeitschrift, vol. No. 47, pp. 724-727, 2003.
Pasquale, "Mechanical Sensors and Actuators", Sensors and Actuators, A: Physical, vol. No. 106, Issue No. 1-3, pp. 142-148, 2003.
Chopra et al., "Selective Gas Detection Using a Carbon Nanotube Sensor", Applied Physics Letters, vol. No. 83, pp. 2280-2282, 2003.
Janata et al., "Conducting Polymers in Electronic Chemical Sensors", Nature Materials, vol. No. 2, pp. 19-24, 2003.
Bauer et al., "Resonant Nanocluster Technology—From Optical Coding and High Quality Security Features to Biochips", Nanotechnology, vol. No. 14, Issue No. 12, pp. 1289-1311, Nov. 4, 2003.
Joseph et al., "Chemiresistor Coatings from Pt- and Au-Nanoparticle/Nonanedithiol Films: Sensitivity to Gases and Solvent Vapors", Sensors and Actuators B: Chemical, vol. No. 98, Issue No. 2-3, pp. 188-195, Mar. 15, 2004.
Shamsipur et al., "New Macrocyclic Diamides as Neutral Ionophores for Highly Selective and Sensitive PVC-Membrane Electrodes for Be2+Ion", Electroanalysis, vol. No. 16, Issue No. 4, pp. 282-288, Mar. 2004.
Fransen, "New Control System Detects Desalter Problems before Upsets Occur", Agar Corporation, Prepared for presentation at The Aiche 2004 Spring National Meeting, Apr. 2004.
Bennett et al., "Monitoring the Operation of an Oil/Water Separator using Impedance Tomography", Minerals Engineering, vol. No. 17, Issue No. 5, pp. 605-614, May 2004.
Pavlov et al., "Aptamer-Functionalized Au Nanoparticles for the Amplified Optical Detection of Thrombin", Journal of Ihe American Chemical Society, vol. No. 126, Issue No. 38, pp. 11768-11769, 2004.
Varma et al., "High-Speed Label-Free Detection by Spinning-Disk Micro-Interferometry", Biosensors and Bioelectronics, vol. No. 19, Issue No. 11, pp. 1371-1376, 2004.
Seyfried et al., "Measurement of Soil Water Content with a 50-MHz Soil Dielectric Sensor", Soil Science Society of America, vol. No. 68, Issue No. 2, pp. 394-403, 2004.
Want et al., "Enabling Ubiquitous Sensing with RFID", Computer, vol. No. 37, Issue No. 4, pp. 84-86, 2004.
Briglln et al., "Detection of Organic Mercaptan Vapors using Thin Films of Alkylamine-Passivated Gold Nanocrystals", Langmuir, vol. No. 20, Issue No. 2, pp. 299-305, 2004.
Ikenishi et al., "The Dielectric Characteristics of Agricultural Land for On-site and Real Time Measurement", SICE 2004 Annual Conference on, IEEE Xplore, vol. No. 2, pp. 1489-1492, Aug. 4-6, 2004.
Thomas et al., "Conjugated Polymer Sensors: Design Principles Towards Enhanced Versatility", Report No. A035334, 2 pages, Dec. 2004.
Rose et al., "Sensitivity Gains in Chemosensing by Lasing Action in Organic Polymers", Nature, vol. No. 434, pp. 876-879, Apr. 14, 2005.
Holstad et al., "Scattered Gamma Radiation Utilized for Level Measurements in Gravitational Separators", IEEE Sensors, vol. No. 5, Issue No. 2, pp. 175-182, Apr. 2005.
Cheung et al., "Impedance Spectroscopy Flow Cytometry: on-Chip Label-Free cell Differentiation", Cytometry A, vol. No. 65, Issue No. 2, pp. 124-132, Jun. 2005.
Jang et al., "Chemical Sensors Based on Highly Conductive Poly(3,4-Ethylene- Dioxythiophene) Nanorods", Advanced Materials, vol. No. 17. Issue No. 13, pp. 1616-1620, Jul. 2005.
Rakow et al., "Molecular Recognition and Discrimination of Amines with a Colorimetric Array", Angewandte Chemie, vol. No. 44, Issue No. 29, pp. 4528-4532, Jul. 18, 2005.
Zhang et al., "Colorimetric Sensor Array for Organics in Water", Journal of the American Chemical Society, vol. No. 127, Issue No. 33, pp. 11548-11549, 2005.
Jaworski et al., "Measurements of Oil-Water Separation Dynamics in Primary Separation Systems Using Distributed Capacitance Sensors", Flow Measurement and Instrumentation, vol. No. 16, Issue No. 2-3, pp. 113-127, 2005.
Burnell et al., "Synthesis and Electrooptical Properties of Copolymers Derived from Phenol-Functionalized Telechelic Oligofluorenes", Macromolecules, vol. No. 38, Issue No. 26, pp. 10667-10677, 2005.
Chuang et al., "Embeddable Wireless Strain Sensor Based on Resonant RF Cavities", Review of Scientific Instruments, vol. No. 20, pp. 1-7, Sep. 2005.
Bang et al., "A Novel Electrochemical Detection Method for Aptamer Biosensors", Biosensors and Bioelectronics, vol. No. 21, Issue No. 6, pp. 863-870, Dec. 15, 2005.
Locklin et al., "Effect of Morphology on Organic Thin Film Transistor Sensors", Analytical and Bioanalytical Chemistry, vol. No. 384, Issue No. 2, pp. 336-342, Jan. 2006.
Meng et al., "A Multi-Electrode Capacitance Probe for Phase Detection in Oil-Water Separation Processes: Design, Modelling and Validation", Measurement Science and Technology, vol. No. 17, Issue No. 4, pp. 881-894, Mar. 2006.
Casanella et al., "Oil-water Interface Level Sensor Based on an Electrode Array", Instrumentation and Measurement Technology Coference, Sorrento, Italy, pp. 710-713, Apr. 24-27, 2006.
Lange et al., "Measuring Biomolecular Binding Events with a Compact Disc Player Device", Angewandte Chemie International Edition, vol. No. 45, pp. 270-273, 2006.
Yang, "Sensors and Instrumentation for Monitoring and Control of Multi-Phase Separation", Measurement and Control, vol. No. 39, Issue No. 6, pp. 178-184, Jul. 2006.
Morris et al., "Wireless Sensor Array System for Combinatorial Screening of Sensor Materials", Combinatorial Methods and Informatics in Materials Science, vol. No. 894, pp. 219-224, 2006.

(56) References Cited

OTHER PUBLICATIONS

Persaud et al., "Analysis of Discrimination Mechanisms in the Mammalian Olfactory System Using a Model Nose", Nature, vol. No. 299, pp. 352-355, Sep. 23, 1982.

Sen et al., "Frequency Dependent Dielectric and Conuctivity Response of Sedimentary Rocks", Journal of Microwave Power, vol. No. 18, Issue No. 1, pp. 95-105, 1983.

Raythatha et al., "Dielectric Properties of Clay Suspensions in MHz to GHz Range", Journal of Colloid and Interface Science, vol. No. 109, Issue No. 2, pp. 301-309, Feb. 1986.

Ward et al., "In Situ Interfacial Mass Detection with Piezoelectric Transducers", Science, vol. No. 249, Issue No. 1972, pp. 1000-1007, Aug. 31, 1990.

Shi et al., "Capacitance-Based Instrumentation for Multi-Interface Level Measurement", Measurement Science and Technology, vol. No. 2, Issue No. 10, pp. 923-933, 1991.

Wise et al., "Microfabrication Techniques for Integrated Sensors and Microsystem", Science, vol. No. 254, pp. 1335-1342, 1991.

Mullen et al., "Trace Detection of Ionic Species with Surface Enhanced Raman Spectroscopy", Spectroscopy, vol. No. 7, pp. 24-32, 1992.

Ervin et al., "Development of a Fiber-Optic Sensor for Trace Metal Detection in Aqueous Environments", Applied Optics, vol. No. 32, Issue No. 22, pp. 4287-4290, Aug. 1, 1993.

Agar et al., "Energy Absorption Probes Control Oily-Water Discharges", Hydrocarbon Processing, vol. No. 72, Issue No. 8, Aug. 1, 1993.

Wensink, "Dielectric Properties of Wet Soils in the Frequency Range 1-3000 MHz", Geophysical Prospecting, vol. No. 41, Issue No. 6, pp. 671-696, Aug. 1993.

Garrouch et al., "The Influence of Clay Content, Salinity, Stress, and Wettability on the Dielectric Properties of Brine-Saturated Rocks: 10 Hz to 10 MHz", Geophysics, vol. No. 59, Issue No. 6, pp. 909-917, Jun. 1994.

Pal, "Techniques for Measuring the Composition (Oil and Water Content) of Emulsions-Astate of the Art Review", Colloids and Surfaces: A Physicochemical and Engineering Aspects, vol. No. 84, Issue No. 2-3, pp. 141-193, 1994.

Isaksen et al., "A Capacitance-Based Tomography System for Interface Measurement in Separation Vessels", Measurement Science and Technology, vol. No. 5, Issue No. 10, pp. 1262-1271, Jun. 1994.

Yang et al., "A Multi-Interface Level Measurement System using a Segmented Capacitance Sensor for Oil Separators", Measurement Science and Technology, pp. 1177-1180, Jul. 19, 1994.

Amrani et al., "High-Frequency Measurements of Conducting Polymers: Development of a New Technique for Sensing Volatile Chemicals", http://iopscience.iop.org/0957-0233/6/10/010; 8 Pages, 1995.

Legin et al "Development and Analytical Evaluation of a Multisensor System for Water Quality Monitoring", Sensors and Actuators B: Chemical, vol. No. 27, Issue No. 1-3, pp. 377-379, Jun. 1995.

Nicolaou et al., "Radiofrequency Encoded Combinatorial Chemistry", Angewandte Chemie International Edition, vol. No. 34, pp. 2289-2291, 1995.

Garcia-Golding et al., "Sensor for Determining the Water Content of Oil-in-water Emulsion by Specific Admittance Measurement", Sensors and Actuators: A. Physical, vol. No. 47, Issue No. 1-3, pp. 337-341, 1995.

Hutzler et al., "Measurement of Foam Density Profiles Using AC Capacitance", Europhysics Letters, vol. No. 31, Issue No. 8, pp. 497-502, Sep. 10, 1995.

Di Natale et al., "Multicomponent Analysis of Heavy Metal Cations and Inorganic Anions in Liquids by a Non-Selective Chalcogenide Glass Sensor Array", Sensors and Actuators B: Chemical, vol. No. 34, Issue No. 1-3, pp. 539-542, Aug. 1996.

Malinowska et al., "Enhanced Electrochemical Performance of Solid-State Ion Sensors Based on Silicone Rubber Membranes", Sensors and Actuators B: Chemical, vol. No. 43, Issue No. 1-3, pp. 161-167, Jul. 1996.

Amrani et al., "Multi-frequency Measurements of Organic Conducting Polymers for Sensing of Gases and Vapours", Sensors and Actuators B: Chemical, vol. No. 33, Issue No. 1-3, pp. 137-141, Jul. 1996.

Leff et al., "Synthesis and Characterization of Hydrophobic, Organically-Soluble Gold Nanocrystals Functionalized with Primary Amines", Langmuir, vol. No. 12, Issue No. 20, pp. 4723-4730, 1996.

Chinowsky et al., "Experimental Data from a Trace Metal Sensor Combining Surface Plasmon Resonance with Anodic Stripping Voltametry", Sensors and Actuators B: Chemical, vol. No. 35, Issue No. 1-3, pp. 37-43, Sep. 1996.

Josse et al., "AC-Impedance-Based Chemical Sensors for Organic Solvent Vapors", Sensors and Actuators B: Chemical, vol. No. 36, Issue No. 1-3, pp. 363-369, Oct. 1996.

Kress-Rogers, "Handbook of Biosensors and Electronic Noses: Medicine, Food, and the Environment", CRC Press, 20 pages, Oct. 24, 1996 (Summary).

Santamarina et al., "Dielectric Permittivity of Soils Mixed With Organic and Inorganic Fluids (0.02ghz to 1.30 GHz)", Journal of Environmental and Engineering Geophysics, vol. No. 2, Issue No. 1, pp. 37-52, 1997.

MacDiarmid, "Synthetic Metals": A Novel Role for Organic Polymers (Nobel Lecture), Angew. Chem. Int. Ed. 2001, vol. 40, pp. 2581-2590.

Vlasov et al., "Cross-Sensitivity Evaluation of Chemical Sensors for Electronic Tongue: Determination of Heavy Metal Ions", Sensors and Actuators B: Chemical, vol. No. 44, Issue No. 1-3, pp. 532-537, Oct. 1997.

Di Natale et al., "Multicomponent Analysis on Polluted Waters by Means of an Electronic Tongue", Sensors and Actuators B: Chemical, vol. No. 44, Issue No. 1-3, pp. 423-428, Oct. 1997.

Ehret et al., "On-line Control of Cellular Adhesion with Impedance Measurements Using Interdigitated Electrode Structures", Medical & Biological Engineering & Computing, vol. No. 36, Issue No. 3, pp. 365-370, May 1998.

Wohltjen et al., "Colloidal Metal-Insulator-Metal Ensemble Chemiresistor", Anal.Chem, vol. No. 70, Issue No. 14, pp. 2856-2859, 1998.

Chyan et al., "Ultrapure Water Quality Monitoring by a Silicon-Based Potentiometric Sensor" Analyst, vol. No. 125, Issue No. 1, pp. 175-178, 1999.

Homola et al., "Surface Plasmon Resonance Sensors: Review", Sensors and Actuators B: Chemical, vol. No. 54, Issue No. 1-2, pp. 3-15, Jan. 25, 1999.

Jaworski et al., "A Capacitance Probe for Interface Detection in Oil and Gas Extraction Plant", Measurement of Science and Technology, vol. No. 10, Issue No. 3, pp. L15-L20, Jan. 1999.

Amrani et al., "Multi-Frequency Interrogation Technique Applied to Conducting Polymer Gas and Odour Sensors", vol. 146, pp. 95-101, Mar. 1999.

Schuller et al., "Advanced Profile Gauge for Multiphase Systems", 1st World Congress on Industrial Process Tomography, Buxton, Greater Manchester, Apr. 14-17, 1999.

Asskildit et al., "New Measuring Sensor for Level Detection in Subsea Separators", ABB Review, pp. 11-17, Apr. 1999.

Ishida et al., "Effects of pH on Dielectric Relaxation of Montmorillonite, Allophane, and Imogolite Suspensions, Colloid and Interface Science", ScienceDirect, vol. No. 212, Issue No. 1, pp. 152-161, Apr. 1999.

Legin et al., "The Features of the Electronic Tongue in Comparison with the Characterstics of the Discrete Ion Selective Sensor", Sensors and Actuators B: Chemical, vol. No. 58, Issue No. 1-3, pp. 464-468, Sep. 21, 1999.

Artmann, "Electronic Identification Systems: State of the Art and their Further Development", Computers and Electronics in Agriculture, vol. No. 24, Issue No. 1-2, pp. 5-26, Nov. 1999.

Jurs et al., "Computational Methods for the Analysis of Chemical Sensor Array Data from Volatile Analytes", Chemical Reviews, vol. No. 100, Issue No. 7, pp. 2649-2678, 2000.

McQuade et al., "Conjugated Polymer-Based Chemical Sensors", Chem. Rev, vol. No. 100, Issue No. 7, pp. 2537-2574, 2000.

Vlasov et al., "Electronic Tongue—New Analytical Tool for Liquid Analysis on the basis of Non-Specific Sensors and Methods of

(56) References Cited

OTHER PUBLICATIONS

Pattern Recognition", Sensors and Actuators B: Chemical, vol. No. 65, Issue No. 1-3, pp. 235-236, Jun. 30, 2000.
Rakow et al., "A Colorimetric Sensor Array for Odour Visualization", Nature, vol. No. 406, pp. 710-713, Aug. 17, 2000.
Taton et al., "Scanometric DNA Array Detection with Nanoparticle Probes", Science, vol. No. 289, Issue No. 5485, pp. 1757-1760, Sep. 8, 2000.
Shirakawa, "The Discovery of Polyacetylene Film: The Dawning of an Era of Conducting Polymers", Angewandte Chemie International Edition, vol. No. 40, Issue No. 14, pp. 2574-2580, Jul. 16, 2001.
Ong et al., "Design and Application of a Wireless, Passive, Resonant-Circuit Environmental Monitoring Sensor", Sensors and Actuators A: Physical, vol. No. 93, Issue No. 1, pp. 33-43, Aug. 25, 2001.
Kaya, "A Electrical Spectroscopy of Kaolin and Bentonite Slurries", Turkish Journal of Engineering and Environmental Sciences, vol. No. 25, pp. 345-354, 2001.
Lee, "Increase Oil Production and Reduce Chemical Usage through Separator Level Measurement by Density Profiling", ISA Tech/Expo Technology Update Conference Proceedings, vol. No. 416, pp. 321-328, 2001.
Bauerle, "Study of Solid Electrolyte Polarization by a Complex Admittance Method", Journal of Physics and Chemistry of Solids, vol. No. 30, Issue No. 12, pp. 2657-2670, Dec. 1969.
Matsui, "Complex-Impedance Analysis for the Development of Zirconia Oxygen Sensors", Solid State Ionics, vol. No. 3-4, pp. 525-529, Aug. 1981.
Gutierrez et al., "Use of Complex Impedance Spectroscopy in Chemical Sensor Characterization", Sensors and Actuators B: Chemical, vol. No. 4, Issue No. 3-4, pp. 359-363, Jun. 1991.
Ghiotti et al., "Moisture Effects on Pure and Pd-Doped SnO2 Thick Films Analysed by FTIR Spectroscopy and Conductance Measurements", Sensors and Actuators B: Chemical, vol. No. 25, Issue No. 1-3, pp. 520-524, Apr. 1995.
Wang et al., "The Application of A.C. Impedance Technique for Detecting Glycol Contamination in Engine Oil", Sensors and Actuators B: Chemical, vol. No. 40, Issue No. 2-3, pp. 193-197, May 15, 1997.
Amrani et al., "An Intelligent Gas Sensing System", Sensors and Actuators B: Chemical, vol. No. 44, Issue No. 1-3, pp. 512-516, Oct. 1997.
Basu et al., ""Smart Sensing" of Oil Degradation and Oil Level Measurements in Gasoline Engines", SAE 2000 World Congress, Detroit, Michigan, 2000-1-1366, pp. 1-7, Mar. 6-9, 2000.
Foster et al., "Detection of Trace Levels of Water in Oil by Photoacoustic Spectroscopy", Sensors and Actuators B: Chemical, vol. No. 77, Issue No. 3, pp. 620-624, Jul. 10, 2001.
Foster-Mills et al., "Photoacoustic Spectroscopy Detects Water in Oil", Sensors Online, pp. 1-5, Oct. 2001, Retrieved from http://archives.sensorsmag.com/articles/1001/12/pf_main.shtml on Apr. 11, 2016.
Smiechowski et al., "Electrochemical Monitoring of Water-Surfactant Interactions in Industrial Lubricants", Journal of Electroanalytical Chemistry, vol. No. 534, Issue No. 2, pp. 171-180, Oct. 18, 2002.
Finkenzeller, "RFID Handbook: Fundamentals and Applications in Contactless Smart Cards and Identification", John Wiley & Sons, Ltd, Second Edition, pp. 1-427, Jul. 21, 2003.
Wang et al., "A New Technique for Detecting Antifreeze in Engine Oil During Early Stage of Leakage", Sensors and Actuators B: Chemical, vol. No. 96, Issue No. 1-2, pp. 157-164, Nov. 15, 2003.
Barsoukov et al., "Impedance Spectroscopy: Theory, Experiment, and Applications", Second Edition, pp. 205-264, 2005.
Lvovich et al., "Impedance Characterization of Industrial Lubricants", Electrochimica Acta, vol. No. 51, Issue No. 3-9, pp. 1487-1496, Jan. 20, 2006.
Qing et al., "RFID Tag Antennas", Antennas for Portable Devices, John Wiley & Sons, Ltd, pp. 59-61; 65-69, Mar. 2007.
Ulrich et al., "Simultaneous Estimation of Soot and Diesel Contamination in Engine Oil Using Electrochemical Impedance Spectroscopy", Sensors and Actuators B: Chemical, vol. No. 127, Issue No. 2, pp. 613-618, Nov. 15, 2007.
Surman et al., "Quantitation of Toxic Vapors in Variable Humidity Atmosphere Using Individual Passive Radio Frequency Identification (RFID) Sensors", 12th International Meeting on Chemical Sensors, Columbus, pp. 1-2, 2008.
Agoston et al., "A Concept of an Infrared Sensor System for Oil Condition Monitoring", Elektrotechnik & Informationstechnik, vol. No. 125, Issue No. 3, pp. 71-75, Mar. 2008.
Wudy et al., "Rapid Impedance Scanning QCM for Electrochemical Applications Based on Miniaturized Hardware and High-Performance Curve Fitting", Electrochimica Acta, vol. No. 53, Issue No. 22, pp. 6568-6574, Sep. 20, 2008.
Sacristan-Riquelme et al., "Low Power Impedance Measurement Integrated Circuit for Sensor Applications", Microelectronics Journal, vol. No. 40, Issue No. 1, pp. 177-184, Jan. 2009.
Niedermayer et al., "Yet Another Precision Impedance Analyzer (YAPIA)—Readout Electronics for Resonating Sensors", Sensors and Actuators A: Physical, vol. No. 156, Issue No. 1, pp. 245-250, Nov. 2009.
Mortier et al., "Chemistry and Technology of Lubricants", Third Edition, Springer, pp. 1-560, 2010.
Potyrailo et al., "Multivariable MHz and GHz Wireless Chem/Bio Sensors for Environmental, Industrial, and Security Applications", The 14th International Meeting on Chemical Sensors, Nuremberg, Germany, pp. 399-402, May 20-23, 2012.
Agilent Impedance Measurement Handbook, "A Guide to Measurement Technology and Techniques", 4th Edition, Agilent Technologies, pp. 1-140, Sep. 10, 2013.
Elzagzoug et al., "Condition Monitoring of High Voltage Transformer Oils Using Optical Chromaticity", Measurement Science and Technology, vol. No. 25, Issue No. 6, pp. 1-9, Jun. 2014.
Hoja et al., "Miniaturized Impedance Analyzer Using AD5933", Lecture Notes on Impedance Spectroscopy, vol. No. 5, pp. 93-100, Feb. 17, 2015.
Chabowski et al., "Simple Wide Frequency Range Impedance Meter Based on AD5933 Integrated Circuit", Metrology and Measurement Systems, vol. No. 22, Issue No. 1, pp. 13-24, Mar. 15, 2015.
Simic, "Complex Impedance Measurement System for the Frequency Range from 5 kHz to 100 kHz", Key Engineering Materials, vol. No. 644, pp. 133-136, May 11, 2015.
Chen et al., "Novel Undercoupled Radio-Frequency (RF) Resonant Sensor for Gaseous Ethanol and Interferents Detection", Sensors and Actuators A: Physical, vol. No. 230, pp. 63-73, Jul. 1, 2015.
Ghaffari et al., "A Wireless Multi-Sensor Dielectric Impedance Spectroscopy Platform", Sensors, vol. No. 15, Issue No. 9, pp. 23572-23588, Sep. 17, 2015.
Wang et al., "Probe Improvement of Inductive Sensor for Online Health Monitoring of Mechanical Transmission Systems", IEEE Transactions on Magnetics, vol. No. 51, Issue No. 11, pp. 1-4, Nov. 2015.
Poseidon Systems, "Oil Quality Products", Trident QM1100; Trident QM2100; Trident WM800, pp. 1-3, Retrieved from http://www.poseidonsys.com/products/oil-quality on Dec. 24, 2015.
Tandelta Systems, "Oil Quality Sensor", Tandelta Oil Condition Monitoring, pp. 1-5, Retrieved from http://www.tandeltasystems.com/products/oil-quality-sensor-2/ on Dec. 24, 2015.
A Chinese Office Action issued in connection with related CN Application No. 201380050788.0 dated Jan. 20, 2016.
AU Examination Report issued in connection with related AU Application No. 2013305814 dated Jun. 10, 2016.
Eurasian Search Report issued in connection with Corresponding EA Application No. 201592216 dated Aug. 4, 2016.
Yang et al., "Chemical Identification Using an Impedance Sensor Based on Dispersive Charge Transport", Applied Physics Letters, vol. No. 88, pp. 1-3, 2006.
Benini et al., "Wireless Sensor Networks: Enabling Technology for Ambient Intelligence", Microelectronics Journal, vol. No. 37, Issue No. 12, pp. 1639-1649, Dec. 2006.
Bai et al., "Gas Sensors Based on Conducting Polymers", Sensors (Basel), vol. No. 7, Issue No. 3, pp. 267-307, Mar. 2007.

(56) References Cited

OTHER PUBLICATIONS

Casanella et al., "Continuous Liquid Level Measurement Using a Linear Electrode Array", Measurement Science and Technology, vol. No. 18, Issue No. 7, pp. 178-184, May 9, 2007.

Lu et al., "MEMS-Based Inductively Coupled RFID Transponder for Implantable Wireless Sensor Applications", IEEE Transactions on Magnetics, vol. No. 43, Issue No. 6, pp. 2412-2414, 2007.

Potyrailo et al., "Multianalyte Chemical Identification and Quantitation Using a Single Radio Frequency Identification Sensor", Analytical Chemistry, vol. No. 79, Issue No. 1, pp. 45-51, 2007.

Potyrailo et al., "Wireless Resonant Sensor Array for High-Throughput Screening of Materials", Review of Scientific Instruments, vol. No. 78, 2007.

Sugiyasu et al., "Conducting-Polymer-Based Chemical Sensors: Transduction Mechanisms", Bulletin of the Chemical Society of Japan, vol. No. 80, pp. 2074-2083, 2007.

Tan et al., "A Wireless, Passive Sensor for Quantifying Packaged Food Quality", Sensors, vol. No. 7, Issue No. 9, pp. 1747-1756, 2007.

Gutzeit, "Controlling Crude Unit Overhead Corrosion—Rules of Thumb for Better Crude Desalting", NACE International Corrosion Conference Series, pp. 075671-0756721, 2007.

Hua et al., "Gas sensor based conducting polymers", Sensors, vol. No. 7, pp. 267-307, 2007.

Hwang et al., "Photoelectron Spectroscopic Study of the Electronic Band Structure of Polyfluorene and Fluorene-Arylamine Copolymers at Interfaces", The Journal of Physical Chemistry C, vol. No. 111, Issue No. 3, pp. 1378-1384, 2007.

Armani et al., "Single-Molecule Detection with Optical Microcavities", Science, vol. No. 317, Issue No. 5839, pp. 783-787, Aug. 10, 2007.

Li et al., "Chemosensory Performance of Molecularly Imprinted Fluorescent Conjugated Polymer Materials", Journal of the American Chemical Society, vol. No. 129, Issue No. 51, pp. 15911-15918, 2007.

Li et al., "Inkjet Printed Chemical Sensor Array Based on Polythiophene Conductive Polymers", Sensors and Actuators B, vol. No. 123, pp. 651-660, 2007.

Wang et al., "Array of Molecularly Mediated Thin Film Assemblies of Nanoparticles: Correlation of Vapor Sensing with Interparticle Spatial Properties", Journal of the American Chemical Society, vol. No. 129, Issue No. 7, pp. 2161-2170, 2007.

Wei et al., "Simple and Sensitive Aptamer-Based Colorimetric Sensing of Protein using Unmodified Gold Nanoparticle Probes", Chemical Communications, pp. 3735-3737, 2007.

Metzger et al., "Low-cost Weight-sensitive Foam to Monitor Product Availability on Retail Shelves", International Conference on Pervasive Computing (Pervasive2007), pp. 268-279, 2007.

Hewitt, "Oil/Water Interface Control for Desalters", Petroleum Technology Quarterly 2007, vol. No. 12, Issue No. 5, pp. 75-78, 2007.

Hwili et al., "Multi-Modality Multi-Interface Level Measurement", Physics: Conference Series, vol. No. 76, Issue No. 1, pp. 1-6, 2007.

Wang et al., "A Gold Nanoparticle-Based Aptamer Target Binding Readout for ATP Assay", Advanced Materials, vol. No. 19, Issue No. 22, pp. 3943-3946, Nov. 2007.

Tanaka et al., "Quartz Crystal Capacitive Sensor with Inductance-Capacitance Resonance Circuit for Vapor Sensing", Japanese Journal of Applied Physics, vol. No. 46, Issue No. 11, pp. 7509-7511, Nov. 2007.

Wang et al., "Aptamer Biosensor for Protein Detection using Gold Nanoparticles", Analytical Biochemistry, vol. No. 373, Issue No. 2, pp. 213-219, Feb. 15, 2008.

Wang et al., "Electrochemical Sensors for Clinic Analysis", Sensors (Basel), vol. No. 8, Issue No. 4, pp. 2043-2081, Apr. 2008.

Potyrailo et al., "Position-Independent Chemical Quantitation with Passive 13.56-Mhz Radio Frequency Identification (RFID) Sensors", Talanta, vol. No. 75, Issue No. 3, pp. 624-628, May 15, 2008.

Röck et al., "Electronic Nose: Current Status and Future Trends", Chemical Reviews, vol. No. 108, pp. 705-725, 2008.

Jimenez et al., "Surface Characterization of Clay Particles via Dielectric Spectroscopy", Annales Umcs, Chemistry, vol. No. 63, Issue No. 1, pp. 73-86, Jan. 2008.

Xiang-Hong et al., "Sensors and Biosensors for the Determination of Small Molecule Biological Toxins", Sensors, vol. No. 8, Issue No. 9, pp. 6045-6054, 2008.

Metzger et al., "Flexible-Foam-Based Capacitive Sensor Arrays for Object Detection at Low Cost", Applied Physics Letters, vol. No. 92, Issue No. 1, 2008.

Zheng et al., "Resonance Impedance Sensing of Human Blood Cells", Sensors and Actuators A: Physical, vol. No. 145-146, pp. 29-36, 2008.

Potyrailo et al., "Modeling of Selectivity of Multi-Analyte Response of Passive Radio Frequency Identification (RFID) Sensors", 12th International Meeting on Chemical Sensors, Columbus, 2008.

Potyrailo et al., "RFID Sensors based on Ubiquitous Passive 13.56-MHz RFID Tags and Complex Impedance Detection", Wireless Communications and Mobile Computing, pp. 1-13, 2008.

UID, "Ultrasonic Interface Level Detector", Christian Michelsen Research, 2008.

Diamond et al., "Wireless Sensor Networks and Chemo-/Biosensing", Chemical Reviews, vol. No. 108, Issue No. 2, pp. 652-679, 2008.

Hatchett et al., "Composites of Intrinsically Conducting Polymers as Sensing Nanomaterials", Chemical Reviews, vol. No. 108, Issue No. 2, pp. 746-769, 2008.

Joo et al., "Chemical Sensors with Integrated Electronics", Chemical Reviews, vol. No. 108, Issue No. 2, pp. 638-651, 2008.

<Kauffman et al., "Carbon Nanotube Gas and Vapor Sensors", Angewandte Chemie International Edition, vol. No. 47, pp. 6550-6570, 2008.

Li et al., "Chemical Sensing Using Nanostructured Polythiophene Transistors", Nano Letters, vol. No. 8, Issue No. 11, pp. 3563-3567, 2008.

Palacios et al., "Rational Design of a Minimal Size Sensor Array for Metal Ion Detection", Journal of the American Chemical Society, vol. No. 130, Issue No. 31, pp. 10307-10314, 2008.

Hwili et al., "A Single Rod Multi-Modality Multi-Interface Level Sensor using an AC Current Source", IEEE International Workshop on Imaging Systems and Techniques, Sep. 10-12, 2008.

Saltas et al., "Dielectric Properties of Non-Swelling Bentonite: The Effect of Temperature and Water Saturation", Journal of Non-Crystalline Solids, vol. No. 354, Issue No. 52-54, pp. 5533-5541, Dec. 15, 2008.

Misra, "Guide to Wireless Sensor Networks", Computer Communications and Networks, Jan. 1, 2009 (Summary).

Ertl et al., "Interdigitated Impedance Sensors for Analysis of Biological Cells in Microfluidic Biochips", E & I Elektrotechnik and Informationstechnik, vol. No. 126, Issue No. 1, pp. 47-50, Feb. 2009.

Potyrailo et al., "Selective Detection of Chemical Species in Liquids and Gases using Passive Radio-Frequency dentification (RFID) Sensors", Proc. Transducers, pp. 1650-1653, 2009.

A Sweden Office Action issued in connection with related SE Application No. 0702495-3 dated Jan. 26, 2009.

Potyrailo et al., "Development of Radio-Frequency Identification Sensors Based on Organic Electronic Sensing Materials for Selective Detection of Toxic Vapors", Journal of Applied Physics, vol. No. 106, Issue No. 12, pp. 124902-1 to124902-6, 2009.

Jaworski et al., "On-line Measurement of Separation Dynamics in Primary Gas/Oil/Water Separators: Challenges and Technical Solutions—A review", Petroleum Science and Engineering, vol. No. 68, pp. 47-59, 2009.

Potyrailo et al., "Combinatorial Screening of Polymeric Sensing Materials Using RFID Sensors",Journal of Combinatorial Chemistry, vol. No. 11, Issue No. 4, pp. 598-603, 2009.

Westafer et al., "Functionalization of High Frequency SAW RFID Devices for Ozone Dosimetry", IEEE Sensors, pp. 1747-1752, Oct. 25-28, 2009.

A Sweden Office Action issued in connection with related SE Application No. 0702495-3 dated Sep. 29, 2009.

(56) References Cited

OTHER PUBLICATIONS

A PCT Search Report and Written Opinion issued in connection with related PCT Application No. PCT/SE2009/051346 dated Mar. 15, 2010.
A US Non-Final Rejection issued in connection with related U.S. Appl. No. 11/560,476 dated Apr. 5, 2010.
Potyrailo et al. "Integration of Passive Multivariable RFID Sensors into Single-Use Biopharmaceutical Manufacturing Components", RFID, 2010 IEEE International, pp. 1-7, Apr. 2010.
Potyrailo et al., "Selective Quantitation of Vapors and their Mixtures using Individual Passive Multivariable RFID Sensors", RFID, 2010 IEEE International, pp. 22-28, Apr. 2010.
Becher et al., "The Detection of Evaporating Hazardous Material Released from Moving Sources Using a Gas Sensor Network", Sensors and Actuators B: Chemical, vol. No. 146, Issue No. 2, pp. 513-520, Apr. 29, 2010.
Potyrailo et al., "Passive Radio Frequency Identification (RFID) Chemical Sensors for Homeland Security Applications", In Wiley Handbook of Science and Technology for Homeland Security, vol. No. 1, pp. 523-544, 2010.
Wang et al., "Flexible Chemiresistor Sensors: Thin film Assemblies of Nanoparticles on a Polyethylene Terephthalate Substrate", Journal of Materials Chemistry, vol. No. 20, pp. 907-915, 2010.
Alexander et al., "Optimization of Interdigitated Electrode (IDE) Arrays for Impedance Based Evaluation of Hs 578T Cancer Cells", Journal of Physics: Conference Series, vol. No. 24, Issue No. 1, pp. 1-4, 2010.
Bobrov et al., "The Effect of Clay and Organic Matter Content on the Dielectric Permittivity of Soils and Grounds at the Frequency Range from 10 MHz to 1 GHz", International Geoscience and Remote Sensing Symposium (IGARSS), pp. 4433-4435, Jul. 25-30, 2010.
Chen et al., "Based on ZigBee Wireless Sensor Network the Monitoring System Design for Production Process Toxic and Harmful Gas", International Conference on Computer, Mechatronics, Control and Electronic Engineering, vol. No. 4, pp. 425-428, 2010.
De Vito et al., "Wireless Sensor Networks for Distributed Chemical Sensing: Addressing Power Consumption Limits with On-Board Intelligence", IEEE Sensors Journal, vol. No. 11, Issue No. 14, pp. 947-955, 2010.
Bianchi et al., "Model of an Interdigitated Microsensor to Detect and Quantify Cells Flowing in a Test Chamber", 6th annual COMSOL Conference Paris, pp. 1-5, Nov. 2010.
Suresh et al., "Piezoelectric Based Resonant Mass Sensor using Phase Measurement", Measurement, vol. No. 14, Issue No. 2, pp. 320-325, Feb. 2011.
Potyrailo et al. "RFID Sensors as the Common Sensing Platform for Single-Use Biopharmaceutical Manufacturing", Measurement Science and Technology, vol. No. 22, 2011.
Potyrailo et al., "Passive Multivariable Temperature and Conductivity RFID Sensors for Single-Use Biopharmaceutical Manufacturing Components", Biotechnology Progress, vol. No. 27, Issue No. 3, pp. 875-884, May 2011.
Owenier et al., "Dielectric Permittivity of Geologic Materials at Different Water Contents—Measurements with an Impedance Analyzer", 6th International Workshop on Advanced Ground Penetrating Radar (IWAGPR), pp. 1-5, Jun. 22-24, 2011.
Potyrailo et al., "Multivariable Passive RFID Vapor Sensors: Pilot-Scale Manufacturing and Laboratory Evaluation", IEEE International Conference on RFID, Poster 52, 2011.
A US Non-Final Rejection issued in connection with related U.S. Appl. No. 12/424,016 dated Jul. 12, 2011.
A PCT Search Report and Written Opinion issued in connection with related PCT Application No. PCT/SE2011/050748 dated Oct. 5, 2011.
A PCT Search Report and Written Opinion issued in connection with related PCT Application No. PCT/SE2011/050818 dated Oct. 24, 2011.
Potyrailo et al., "Materials and Transducers Toward Selective Wireless Gas Sensing", Chemical Reviews, vol. No. 111, Issue No. 11, pp. 7315-7354, Nov. 9, 2011.
Datla et al., "Wireless Distributed Computing: A Survey of Research Challenges", IEEE Communications Magazine, vol. No. 50, Issue No. 1, pp. 144-152, Jan. 2012.
A Combined GB Search and Examination Report issued in connection with related GB Application No. GB1121548.0 dated Mar. 28, 2012.
Vasilyeva et al., "Differences in Behaviour of Adsorbed Water in Kaolinites and Montmorillonites in Temperature Range from −90° C. to +140° C. by Dielectric Spectroscopy", Physics: Conference Series, vol. No. 394, Issue No. 1, pp. 1-6, 2012.
A US Non-Final Rejection issued in connection with related U.S. Appl. No. 12/824,436 dated Aug. 8, 2012.
US Non-Final Rejection issued in connection with related U.S. Appl. No. 11/560,476 dated Jul. 5, 2012.
Datla et al., "Wireless Distributed Computing in Cognitive Radio Networks", Ad Hoc Networks, vol. No. 10, Issue No. 05, pp. 845-857, Jul. 2012.
Unofficial English Translation of Japanese Office Action issued in connection with related JP Application No. 2007291481 dated Aug. 7, 2012.
A US Non-Final Rejection issued in connection with related U.S. Appl. No. 13/331,003 dated Sep. 10, 2012.
A US Notice of Allowance issued in connection with related U.S. Appl. No. 12/424,016 dated Sep. 28, 2012.
A Chinese Office Action issued in connection with related CN Application No. 200980149087.6 dated Sep. 13, 2012.
A US Non-Final Rejection issued in connection with related U.S. Appl. No. 12/325,653 dated Nov. 16, 2012.
A US Final Rejection issued in connection with related U.S. Appl. No. 12/824,436 dated Feb. 6, 2013.
A US Non-Final Rejection issued in connection with related U.S. Appl. No. 12/942,732 dated Feb. 7, 2013.
Swiech et al., "Dielectric Properties of Synthetic Oil Sands", Society of Petroleum Engineers—SPE Heavy Oil Conference Canada, vol. No. 1, pp. 238-248, 2013.
Zhu et al., "Survey of Lubrication Oil Condition Monitoring, Diagnostics, and Prognostics Techniques and Systems", Journal of Chemical Science and Technology, vol. No. 2, Issue No. 3, pp. 100-115, Jul. 2013.
A US Final Rejection issued in connection with related U.S. Appl. No. 12/325,653 dated Aug. 8, 2013.
Unofficial English Translation of Japanese Office Action issued in connection with related JP Application No. 2011-538590 dated Oct. 8, 2013.
A PCT Search Report and Written Opinion issued in connection with related PCT Application No. PCT/SE2013/050671 dated Nov. 18, 2013.
A PCT Search Report and Written Opinion issued in connection with related PCT Application No. PCT/US2013/058932 dated Dec. 12, 2013.
A PCT Search Report and Written Opinion issued in connection with related PCT Application No. PCT/US2013/058898 dated Dec. 18, 2013.
Unofficial English Translation of Chinese Office Action issued in connection with related CN Application No. 201180031959.6 dated Dec. 26, 2013.
A US Non-Final Rejection issued in connection with related U.S. Appl. No. 12/977,568 dated Jan. 16, 2014.
A PCT Search Report and Written Opinion issued in connection with related PCT Application No. PCT/US2013/055983 dated Jan. 27, 2014.
A US Non-Final Rejection issued in connection with related U.S. Appl. No. 12/827,623 dated Jan. 30, 2014.
A European Search Report and Opinion issued in connection with related EP Application No. 11801238.4 dated Mar. 5, 2014.
A US Non-Final Rejection issued in connection with related U.S. Appl. No. 12/325,653 dated Mar. 17, 2014.
A PCT Search Report and Written Opinion issued in connection with related PCT Application No. PCT/SE2013/051590 dated May 6, 2014.

(56) References Cited

OTHER PUBLICATIONS

A PCT Search Report and Written Opinion issued in connection with related PCT Application No. PCT/SE2013/051589 dated May 6, 2014.
A US Non-Final Rejection issued in connection with related U.S. Appl. No. 13/630,939 dated Aug. 11, 2014.
A US Non-Final Rejection issued in connection with related U.S. Appl. No. 14/031,965 dated Aug. 26, 2014.
Soleimani et al., "Base Oil Oxidation Detection using Novel Chemical Sensors and Impedance Spectroscopy Measurements", Sensors and Actuators B: Chemical, vol. No. 199, pp. 247-258, Aug. 2014.
A US Non-Final Rejection issued in connection with related U.S. Appl. No. 14/031,951 dated Sep. 2, 2014.
A US Final Rejection issued in connection with related U.S. Appl. No. 12/325,653 dated Sep. 12, 2014.
Toledo et al., "Application of Quartz Tuning Forks and Extensional Microresonators for Viscosity and Densit Measurements in Oil/Fuel Mixtures", Microsystem Technologies, vol. No. 20, Issue No. 4, pp. 945-953, 2014.
A US Non-Final Rejection issued in connection with related U.S. Appl. No. 13/484,674 dated Nov. 3, 2014.
A US Non-Final Rejection issued in connection with related U.S. Appl. No. 13/558,499 dated Dec. 4, 2014.
A US Non-Final Rejection issued in connection with related UU.S. Appl. No. 13/630,954 dated Dec. 15, 2014.
A US Non-Final Rejection issued in connection with related U.S. Appl. No. 13/729,800 dated Dec. 19, 2014.
A US Final Rejection issued in connection with related U.S. Appl. No. 13/630,939 dated Jan. 28, 2015.
A US Non-Final Rejection issued in connection with related U.S. Appl. No. 13/630,739 dated Feb. 25, 2015.
Unofficial English Translation of Chinese Office Action issued in connection with related CN Application No. 201180032850.4 dated Mar. 2, 2015.
Unofficial English Translation of Japanese Office Action issued in connection with related JP Application No. 2013518325 dated Mar. 24, 2015.
Zhu et al.,"An Integrated Lubricant Oil Conditioning Sensor Using Signal Multiplexing", Journal of Micromechanics and Micro engineering, vol. No. 25, Issue No. 1, pp. 1-12, 2015.
Unofficial English Translation of Japanese Office Action issued in connection with related JP Application No. 2013-518328 dated Apr. 7, 2015.
A US Non-Final Rejection issued in connection with related U.S. Appl. No. 13/630,587 dated Jun. 2, 2015.
A US Final Rejection issued in connection with related U.S. Appl. No. 13/630,739 dated Jun. 4, 2015.
A US Non-Final Rejection issued in connection with related U.S. Appl. No. 13/838,884 dated Jun. 17, 2015.
A PCT Search Report and Written Opinion issued in connection with related PCT Application No. PCT/US2015/027482 dated Jul. 15, 2015.
Unofficial English Translation of Japanese Notice of Allowance issued in connection with related JP Application No. 2011-258627 dated Aug. 4, 2015.
A Taiwan Office Action issued in connection with related TW Application No. 100146015 dated Aug. 6, 2015.
A US Non-Final Rejection issued in connection with related U.S. Appl. No. 13/630,939 dated Sep. 14, 2015.
Unofficial English Translation of Japanese Grant of Patent issued in connection with related JP Application No. 2013518325 dated Sep. 15, 2015.
A US Non-Final Rejection issued in connection with related U.S. Appl. No. 13/538,570 dated Oct. 22, 2015.
A European Search Report and Opinion issued in connection with related EP Application No. 11801234.3 dated Oct. 28, 2015.
Unofficial English Translation of Chinese Office Action issued in connection with related CN Application No. 201380043615.6 dated Nov. 9, 2015.
A US Non-Final Rejection issued in connection with related U.S. Appl. No. 12/824,436 dated Dec. 2, 2015.
Hammond et al., "An Acoustic Automotive Engine Oil Quality Sensor", Solid State Sensors and Actuators, vol. 2 , Jun. 1997 pp. 1343-1346, Jun. 1997.
Buhrdorf et al., "Multiparameteric Oil Condition Sensor Based on the Tuning Fork Technology for Automotive Applications", In Advanced Microsystems for Automotive Applications, pp. 289-298, 2005
Pejcic et al., "Impedance Spectroscopy: Over 35 Years of Electrochemical Sensor Optimization", Electrochimica Acta, vol. No. 51, Issue No. 28, pp. 6217-6229, 2006.
Hempel et al., "Application of a Portable RF Impedance Spectrum Analyzer for the Investigation of Lateral Field Excited Acoustic Wave Sensors in a Liquid Environment", Ultrasonics Symposium, IEEE, pp. 373-376, Oct. 28-31, 2007.
Wang et al., "A New Method for On-Line Monitoring of Brake Fluid Condition Using an Enclosed Reference Probe", Measurement Science and Technology, vol. No. 18, Issue No. 11, pp. 3625-3635, 2007.
Capone et al., Metal Oxide Gas Sensor Array for the Detection of Diesel Fuel in Engine Oil, Sensors and Actuators B: Chemical, vol. No. 131, Issue No. 01, pp. 125-133, Apr. 2008.
Hempel et al., Lateral Field Excited Quartz Crystal Resonator Sensors for Determination of Acoustic and Electrical Properties of Liquids, IEEE International Frequency Control Symposium, pp. 705-710, 2008.
Guan et al., Engine Lubricating Oil Classification by SAE Grade and Source Based on Dielectric Spectroscopy Data, Analytica Chimica Acta, vol. No. 628, Issue No. 1, pp. 117-120, Oct. 2008.
McCann et al., "Recent Advances in Lateral Field Excited and Monolithic Spiral Coil Acoustic Transduction Bulk Acoustic Wave Sensor Platforms", Measurement Science and Technology, vol. No. 20, Issue No. 12, 2009.
Cho et al., "Capacitive Sensor for Automotive Engine Oil Degradation using Wireless Network", Advanced Packaging Materials: Microtech, IEEE, pp. 88-91, Apr. 2010.
Hong et al., "Development of a Micro Liquid-Level Sensor for Harsh Environments using a Periodic Heating Technique", Measurement Science and Technology, vol. No. 21, Issue No. 10, 2010.
Liu et al., Measurement of Density and Viscosity of Dodecane and Decane with a Piezoelectric Tuning Fork Over 298-448 K and 0.1-137.9 MPa Sensors and Actuators, vol. No. 167, Issue No. 02, pp. 347-353, Mar. 2011.
Sen et al., Evaluation of Sensor Arrays for Engine Oils using Artificial Oil Alteration, Proc. SPIE, vol. No. 8066, May 2011.
Guan et al., "Application of Dielectric Spectroscopy for Engine Lubricating Oil Degradation Monitoring", Sensors and Actuators A: Physical, vol. No. 168, Issue No. 01, pp. 22-29, Jul. 2011.
Wang et al., "Impedance Analysis for Lateral Field Excited Acoustic Wave Sensors", Sensors and Actuators, vol. No. 156, Issue No. 02, pp. 969-975, Aug. 2011.
Latif et al., "Conductometric Sensors for Monitoring Degradation of Automotive Engine Oil", Sensors, vol. No. 11, Issue No. 09, pp. 8611-8625, Sep. 2011.
Pérez et al., "Low-Cost Oil Quality Sensor Based on Changes in Complex Permittivity", Sensors, vol. No. 11, Issue No. 11, pp. 10675-10690, 2011.
Fochtmannet al., "Optimization of the Lateral Field Excited Platform for Liquid Sensing Applications", Sensors and Actuators B: Chemical, vol. No. 170, pp. 95-103, Jul. 2012.
Aghayan, "On-Line Monitoring of Engine Health through the Analysis of Contaminants in Engine Lubricant", The School of Graduate and Postdoctoral Studies The University of Western Ontario London, Ontario, Canada, pp. 1-273, 2012.
De Souza et al., A Close Dielectric Spectroscopic Analysis of Diesel/Biodiesel Blends and Potential Dielectric Approaches for Biodiesel Content Assessment, Fuel, vol. No. 105, pp. 705-710, Mar. 2013.
Unofficial English Translation of Chinese Office Action and Search Report issued from CN Application No. 201110461799.0 dated Mar. 30, 2015.

(56) References Cited

OTHER PUBLICATIONS

Hendrick., "Cellulose Acetate Fibers with Fluorescing Nanoparticles for Anti-Counterfeiting Purposes", Erin Sue Hendrick, pp. 1-36, 2008.
A Australian Examination Report issued in connection with related AU Application No. 2015268746 dated Oct. 21, 2016.
A US Non-Final Office action issued in connection with related U.S. Appl. No. 14/697,086 dated Oct. 31, 2016.
A copy of PCT Search Report and Written Opinion issued in connection with related PCT Application No. PCT/ JS2017/020335 on May 26, 2017.
Unofficial English Translation of Russian Office Action issued in connection with related RU Application No. 2015109381 dated Jun. 22, 2017.
Unofficial English Translation of Russian Office Action issued in connection with related RU Application No. 2015109373 dated Jul. 12, 2017.
Matthaei et al. "A Study of the Properties and Potential Application of Acoustic-Sulwace-Wave Resonators", Electrical Engineering and Computer Science, pp. 284-289,1975.
Davide et al., Dynamic Calibration of QMB Polymer-Coated Sensors by Wiener Kernel Estimation, Sensors and Actuators, vol. No. 27, Issues No. 1-3, pp. 275-285, Jun. 1995.
Wadkins et al. "Calibration of Biosensor Response Using Simultaneous Evanescent Wave Excitation of Cyanine-Labeled Capture Antibodies and Antigens", Analytical Biochemistry, vol. No. 232, Issues No. 1, pp. 73-78, Nov. 1995.
Hartmann et al. "Effects of Polymer Matrices on Calibration Functions of Luminescent Oxygen Sensors Based on Porphyrin Ketone Complexes", Biomedical Research and Development, vol. No. 68, Issues No. 15, pp. 73-78, 2615-2620.
Anicin et al., "Circuit Properties of Coils", IEE Proc-Sei Meas Technol, vol. No. 144, Issue No. 5, pp. 234-239, Sep. 1997.
Berntsson et al., "Multivariate Experimental Methodology Applied to the Calibration of a Clark Type Oxygen Sensor", Analytica Chimica Acta, vol. No. 355, Issue No. 01, pp. 43-53, 1997.
Despagne et al., "Neural Networks in Multivariate Calibration", The Analyst Tutorial Review, pp. 157R-178R, 1998.
Seiter et al., "Redundant Chemical Sensors for Calibration-Impossible Applications", Talanta, vol. No. 54, Issue No. 01 (2001), pp. 99-106, 2001.

Kim et al., "Manipulation of Microenvironment with a Built-In Electrochemical Actuator in Proximity of a Dissolved Oxygen Microsensor", IEEE Sensors Journal, vol. No. 4, Issue No. 5, pp. 568-575, Oct. 2004.
Dorneanu et al., "Computer-controlled System for ISEs Automatic Calibration", Sensors and Actuators, vol. No. 105, pp. 521-531, 2005.
Rivera et al., "Self-Calibration and Optimal Response in Intelligent Sensors Design Based on Artificial Neural Networks", Sensors, vol. No. 07, pp. 1509-1529, 2007.
Loh et al., "Inductively Coupled Nanocomposite Wireless Strain and pH Sensors", Smart Structures and Systems, vol. No. 04, Issue No. 05, pp. 531-548, 2008.
A PCT Search Report and Written Opinion issued in connection with related PCT Application No. PCT/SE2009/050516 dated Jul. 10, 2009.
A US Non-Final Office Action issued in connection with related U.S. Appl. No. 12/118,950 dated Dec. 7, 2010.
A European Search Report and Opinion issued in connection with related EP Application No. 09746862.3 dated Jul. 18, 2011.
Unofficial English Translation of Japanese Office Action issued in connection with related JP Application No. 2011509440 dated Jul. 9, 2013.
Unofficial English Translation of Japanese Office Action issued in connection with related JP Application No. 2011509440 dated Nov. 12, 2013.
Unofficial English Translation of Japanese Office Action issued in connection with related JP Application No. 2011509440 dated Nov. 17, 2015.
Potyrailo, R. A., "Multivariable Sensors for Ubiquitous Monitoring of Gases in the Era of Internet of Things and Industrial Internet", Chemical Reviews, vol. No. 106, pp. 11877-11923, Sep. 7, 2016.
Eurasian Patent Office, Office Action Issued in Eurasian Patent Application No. 201592216/31, dated Oct. 17, 2017, Moscow, Russia, 4 pages.
Zaretsky et al., "Moisture sensing in transformer oil using thin film microdielectrometry," Conference Record of the 1988 IEEE International Symposium on Electrical Insulation, (Jun. 1988) (Abstract).
Machine Translation and First Office Action and Search issued in connection with corresponding CN Application No. 201511015982.2 dated Jan. 19, 2018.
A Chinese language Office Action, with English language translation, dated Apr. 10, 2019 for related CN patent application No. CN 201511015982.2.

* cited by examiner

SENSING METHOD AND SYSTEM

CROSS-REFERENCE TO RELATED APPLICATIONS

This application claims priority to U.S. Provisional Patent Application No. 61/987,853 filed on May 2, 2014. Also, this application is a Continuation-in-Part of the following applications: U.S. patent application Ser. No. 11/560,476 filed on Nov. 16, 2006; U.S. patent application Ser. No. 12/325,653 filed on Dec. 1, 2008; U.S. patent application Ser. No. 12/824,436 filed on Jun. 28, 2010; U.S. patent application Ser. No. 12/827,623 filed on Jun. 30, 2010; U.S. patent application Ser. No. 12/977,568 filed on Dec. 23, 2010; U.S. patent application Ser. No. 13/331,003 filed on Dec. 20, 2011; U.S. patent application Ser. No. 13/484,674 filed on May 31, 2012 (which is a Continuation-in-Part of U.S. patent application Ser. No. 12/424,016 filed on Apr. 15, 2009, now U.S. Pat. No. 8,364,419 issued on Jan. 29, 2013); U.S. patent application Ser. No. 13/538,570 filed on Jun. 29, 2012; U.S. patent application Ser. No. 13/558,499 filed on Jul. 26, 2012; U.S. patent application Ser. Nos. 13/630,939, 13/630,954, 13/630,587, and 13/630,739 all filed on Sep. 28, 2012; U.S. patent application Ser. Nos. 13/729,800 and 13/729,851 both filed on Dec. 28, 2012; U.S. patent application Ser. No. 13/838,884 filed on Mar. 15, 2013; U.S. patent application Ser. Nos. 14/031,951 and 14/031,965 both filed on Sep. 19, 2013; and U.S. patent application Ser. No. 14/532,168 filed on Nov. 4, 2014. All the aforementioned applications are incorporated herein by reference in their entireties.

BACKGROUND

Technical Field

Embodiments are disclosed that relate to sensing methods and systems. The sensors, such as resonant sensors, may include inductor-capacitor-resistor (LCR) sensors that can be used as sensors or transducers for sensing fluids.

Discussion of Related Art

Robust sensing of fluids may be useful in mobile and stationary equipment applications. As an example, if the equipment is a vehicle engine and the fluid is engine oil, then knowledge about oil health may be used to help reduce or prevent unexpected downtime, provide savings from unnecessary oil replacement, and improve service intervals scheduling in vehicles such as locomotives, heavy and light duty trucks; mining, construction, and agriculture vehicles. Other examples of stationary equipment applications may include wind turbines and gensets. Further, knowledge about engine oil health may prevent or reduce the total life cost of passenger cars, improve control of service intervals, and extend the life of engine.

Standard (classic) impedance spectroscopy is a technique that is employed to characterize aspects of material performance. In classic impedance spectroscopy, a material may be positioned between electrodes and probed over a wide frequency range (from a fraction of Hz to tens of GHz) to extract the fundamental information about dielectric properties of the material. However, standard impedance spectroscopy may be limited due to its low sensitivity in reported measurement configurations and prohibitively long acquisition times over the broad frequency range.

It may be desirable to have systems and methods that differ from those systems and methods that are currently available.

BRIEF DESCRIPTION

One embodiment of the disclosure provides a system for analyzing fluid. The system may include a sensor. The sensor may include a resonant inductor-capacitor-resistor (LCR) circuit, a sensing region that includes at least a portion of the LCR circuit, a controller coupled to the sensing region. The sensing region may be placed in operational contact with a fluid of interest. The controller may receive an electrical signal from the sensor. The signal may represent resonant impedance spectra of the sensing region during operational contact with the fluid over a measured spectral frequency range. The signal may be used to analyze the resonant impedance spectra, and to determine one or more properties of the fluid based on the analyzed resonant impedance spectra.

In one embodiment, a method includes exciting a sensor in contact with a fluid. The sensor may include an LCR resonant circuit to operate at one or more frequencies in a frequency range of analysis. A signal may be received from the sensor across the frequency range of analysis. The signal includes information about a sensor in contact with the fluid. One or more properties of the fluid may be determined based at least in part on the resonant impedance spectra.

A system is provided in one embodiment that includes a resonant sensor and a controller. The sensor can sense a complex permittivity of a fluid. The controller may be coupled to the sensor can receive an electrical signal from the sensor. The signal may represent a resonant impedance spectra of the fluid over a measured spectral frequency range. The controller may determine a complex permittivity of the fluid based at least in part on the resonant impedance spectra.

BRIEF DESCRIPTION OF THE DRAWINGS

These and other features may be understood when the following detailed description is read with reference to the accompanying drawings in which like characters represent like parts throughout the drawings, wherein.

DETAILED DESCRIPTION

Figure 1:
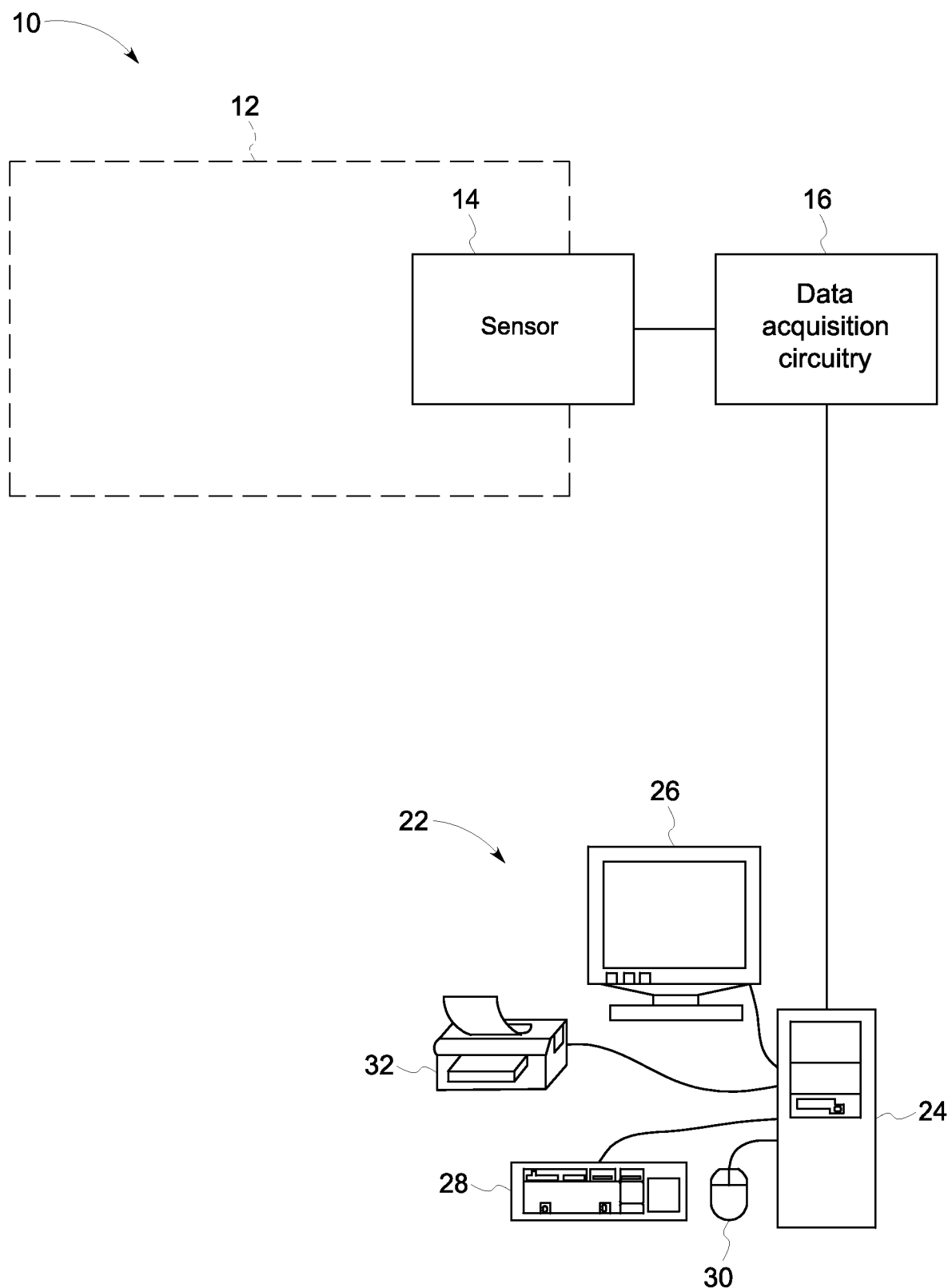
FIG. 1 is a block diagram of a system for assessing fluid according to an embodiment of the disclosure.

Embodiments are disclosed that relate to sensing methods and systems. The sensors, such as resonant sensors, may include inductor-capacitor-resistor (LCR) sensors that can be used as sensors or transducers for sensing fluids. Provided herein are sensors having a part that is a resonant structure that exhibits resolvable changes in the presence of a fluid and various components or contaminants in the fluid.

In one embodiment, the sensor may include an inductor-capacitor-resistor (LCR) resonator circuit with a resonance frequency response provided by the resonant impedance (Z) of this circuit. The sensors as provided herein may be capable of sensing properties of interest in the presence of variable noise sources and operating over the variable temperature conditions to provide stable sensor performance over time. Disclosed herein are sensors that include inductor-capacitor-resistor (LCR) resonators, which may function as a sensor or as a transducer. The resonant impedance spectrum of the sensor may be measured either via inductive coupling between pick up coil and sensor or directly by connecting to a sensor reader. The electrical response of the sensor may be translated into the resonant impedance changes of the sensor.

Non-limiting examples of signal changes of an individual sensor may include combined and simultaneous resonant impedance change, inductance change, resistance change, and capacitance change. Suitable sensors and systems disclosed herein may enhance the ability to measure changes in a fluid, such as engine oil or fuel, by contacting it with the sensor between the electrodes that constitute a resonant circuit of the sensor. The resonant circuit of the sensor may be an electrical resonant circuit. Other resonant circuits may include a mechanical resonator, where a change of viscosity and/or density of the fluid affects a response of the mechanical resonators.

Suitable mechanical resonators may include tuning fork resonators, thickness shear mode resonators, quartz crystal microbalance resonators, surface acoustic wave resonators, bulk acoustic wave resonators, and others. Unlike these and other mechanical resonators, the electrical resonators may be not predictably affected by the changes change of viscosity and/or density of the fluid. Instead, they may be predictably affected by the changes in the complex permittivity of the fluid. Electrical resonators may be very complicated in their design, for example marginal oscillators require complicated multi-component circuits.

The degradation of at least some oils and lubricants may generate molecules and/or other moieties that may be relatively more polar than the oil and lubricant from which they were formed. The base oil or lubricant may include long chain hydrocarbon molecules that are weakly polar. Thus, the presence of polar contaminants may increase of one or more parts of the oil's complex permittivity.

According to one aspect, the resonant transducers operate as re-configurable resonant structures and operate at multiple frequencies for monitoring of a status of fluids (and, further, for example, the health of equipment in contact with such fluids) and to probe more accurately dielectric properties of any samples in the presence of uncontrolled ambient environmental noise contributions. Monitoring the health of fluids involves a determination of composition or a determination of contamination of such fluid.

Non-limiting examples of interferents and ambient environmental noise contributions include temperature and presence of interferences in a sample. The term "interference" includes any undesired environmental parameter that undesirably affects the accuracy and precision of measurements of the sensor. The term "interferent" refers to a material or environmental condition that potentially may produce an erroneous response by the sensor. Filters (physical, chemical, and/or electronic) may be employed, based on the application specific parameters, to reduce, eliminate, or account for the presence and/or concentration of such interferents.

With reference to FIG. 1, a system 10 is shown that may be useful for assessing a fluid in contact therewith. For purposes of illustration, a representative fluid may be engine oil. The system may include a fluid reservoir 12 for a fluid and a sensor 14. Alternatively, the sensor may be set in a flow path of the fluid. The sensor may be a resonant sensor that is disposed in, or on, the reservoir, or may be coupled to in-line connectors in fluid communication with the fluid reservoir that define a flow path. In one embodiment, the sensor may provide continuous monitoring of the fluid within the reservoir or flow path.

Suitable fluids may include hydrocarbon fuels and lubricants. Suitable lubricants may include engine oil, gear oil, hydraulic fluid, lubricating oils, synthetic based lubricants, lubricating fluids, greases, silicones, and the like. Suitable fuels may include gasoline, diesel fuel, jet fuel or kerosene, bio-fuels, petrodiesel-biodiesel fuel blends, natural gas (liquid or compressed), and fuel oils. Still other fluids may be insulating oils in transformers, solvents, or mixtures of solvents. Still other fluids may be included with correspondingly appropriate sensor parameters, such as water, air, engine exhaust, biologic fluids, and organic and/or vegetable oils. The fluid may be a liquid, or may in in a gaseous phase. Further contemplated are multiphase compositions.

Non-limiting examples of various fluid components include unintended leaks from proximate systems (e.g., radiator fluid into engine oil, or water condensation in diesel fuel or transformer oil). Other detectable fluid components may include degradation products of the fluid caused due to elevated temperature of operation, or due to contact with oxidants (air, others). System operation may introduce fluid components such as dirt, salt, soot or carbon, wear metal particles, wear products, and others. In some environments, fouling due to bacteria or the like may be the fluid component. And in all instances, indirect measurement may be useful, such as a pH rise that indicates the presence of an acidic component.

The sensor may detect characteristics of the fluid via a resonant impedance spectral response. One or more of the LCR resonators may measure the resonant impedance spectral response. As opposed to simple resonant impedance measurements, the disclosed embodiments probe the sample with at least one resonant electrical circuit. The resonant impedance spectrum of the sensor in proximity to the sample (the sensor in operational contact with the fluid) varies based on sample composition and/or components and/or temperature. The measured resonant impedance values Z' (which may be the real part of resonant impedance, Zre) and Z" (which may be the imaginary part of resonant impedance, Zim) reflect the response of the fluid (for example, the portion of the fluid in proximity to the sensor) to a stimulus of the electric field of the resonant electrical circuit.

The electrical field may be applied by the sensor via electrodes. The electrodes may be in direct or indirect electrical contact with the sample. For example, a sensor may be a combination of a sensing region and associated circuits. The sensing region may be either bare or coated with a protective dielectric layer. In both cases, the sensing region may be considered to be in operational contact with a fluid. In such embodiments, the tuning circuits may not contact the fluid directly. An example of indirect electrical contact with the sample may be when a sensing electrode structure is coated with a dielectric protective coating and when the electric field that may be generated between the electrodes interacts with the fluid after penetrating through the dielectric protective coating. A suitable dielectric protective coating may be conformally applied to the electrode.

Suitable sensors may include single use or multi-use sensors. A suitable multi-use resonant sensor may be a re-usable sensor that may be used during the lifetime of a system in which it may be incorporated into. In one embodiment, the resonant sensor may be a single use sensor that may be used during all or part of a reaction or process. For example, the resonant sensor may include one or more pairs of electrodes and one or more tuning elements, e.g., a resistor, a capacitor, an inductor, a resonator, impedance transformer, or combinations of two or more thereof to form an inductor-capacitor-resistor (LCR) resonant circuit operated at least one resonant frequency. In certain embodiments, different resonant circuits of a plurality of resonant circuits of a resonant sensor may be configured to resonate at different frequencies. Different frequencies may be selected to be across the dispersion profile of the measured fluid composition. The dispersion profile may be a dependence of the dielectric properties of the fluid composition on the probing frequency. Various components of the fluid have different dispersion profiles. When measured at multiple resonance frequencies, concentrations of different components of the fluid may be determined.

Figure 2:
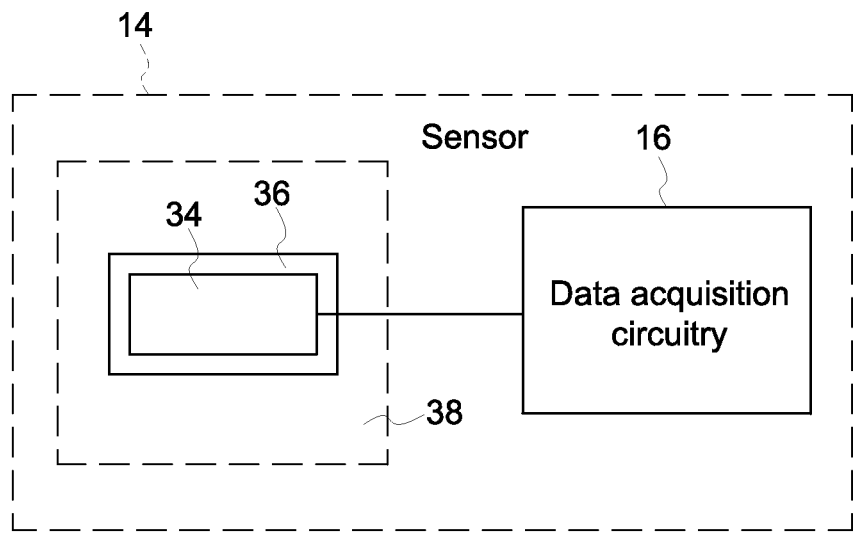
FIG. 2 is a schematic view of a resonant sensor according to an embodiment of the disclosure.

Data from the resonant sensor may be acquired via data acquisition circuitry 16, which may be associated with the sensor or which may be associated with a control system, such as a controller or workstation 22 including data processing circuitry, where additional processing and analysis may be performed. The controller or workstation may include one or more wireless or wired components, and may also communicate with the other components of the system. Suitable communication models include wireless or wired. At least one suitable wireless model includes radio frequency devices, such as RFID wireless communications. Other wireless communication modalities may be used based on application specific parameters. For example, where there may be EMF interference certain modalities may work where others may not. The data acquisition circuitry can be disposed within the fluid reservoir as shown in FIG. 2. Other suitable locations may include disposition being within the workstation. Further, the workstation can be replaced with a control system of the whole process where the resonant sensor and its data acquisition circuitry may be connected to the control system of process.

During operation, the monitoring process may couple to, among other things, operation of an internal combustion engine, an oil-filled transformer, a chemical reaction process, a biological reaction process, purification and/or separation process, a catalytic process, a general combustion process, production of raw oil, production of raw gas, material extraction, and other industrial processes. The data acquisition circuitry may be in the form of a sensor reader, which may be configured to communicate wirelessly or wired with the fluid reservoir and/or the workstation. For example, the sensor reader may be a battery-operated device and/or may be powered using energy available from the main control system or by using harvesting of energy from ambient sources (light, vibration, heat, or electromagnetic energy).

In addition, the data acquisition circuitry may receive data from one or more resonant sensor 14 (e.g., multiple sensors formed in an array or multiple sensors positioned at different locations in or around the fluid reservoir). The data may be stored in short or long term memory storage devices, such as archiving communication systems, which may be located within or remote from the system and/or reconstructed and displayed for an operator, such as at the operator workstation. Non-limiting examples of positioning and installations of sensors and sensor systems of the present techniques include fuel or fluid reservoirs, associated piping components, connectors, flow-through components, and any other relevant process components.

In addition to displaying the data, the operator workstation may control the above-described operations and functions of the system. The operator workstation may include one or more processor-based components, such as general purpose or application specific computers 24. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation or by associated components of the system. Alternatively, the programs and routines may be stored on a computer accessible storage and/or memory remote from the operator workstation but accessible by network and/or communication interfaces present on the computer. The computer may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

The sensor may include a plurality of resonant circuits that may be configured to probe the fluid in the fluid reservoir with a plurality of frequencies. The fluid reservoir may be a reservoir bound by the engineered fluid-impermeable walls or by naturally formed fluid-impermeable walls or by the distance of the electromagnetic energy emitted from the sensor region to probe the fluid. Further, the different frequencies may be used to probe a fluid sample at different depths. In certain embodiments, an integrated circuit memory chip may be galvanically coupled to the resonant sensor. The integrated circuit memory chip may contain different types of information. Non-limiting examples of such information in the memory of the integrated circuit chip include calibration coefficients for the sensor, sensor lot number, production date, end-user information. In another embodiment, the resonant sensor may be an interdigital structure that may be a part of the resonator and has a sensing region.

In certain embodiments, when an integrated circuit memory chip may be galvanically coupled to the resonant sensor, readings of the sensor response may be performed with a sensor reader that contains circuitry operable to read the analog portion of the sensor. The analog portion of the sensor may include resonant impedance. The digital portion of the sensor may include information from the integrated circuit memory chip.

FIG. 2 illustrates a non-limiting example of a design of the resonant sensor. A sensing electrode structure 34 of the sensor may be connected to the tuning circuits and the data acquisition circuitry. A sensing electrode structure 34 can be bare and in direct contact with the fluid. Alternatively, the sensing electrode structure can be coated with a protective coating 36. The sensing electrode structure, without or with the protective coating, forms a sensing region 38. The coating may be applied conformally, and may be a dielectric material. The sensing electrode structure, without or with the protective coating that forms the sensing region, may operationally contact a fluid. The fluid contains the analyte or contaminant(s). The sensing electrode structure may be either without (bare) or with a protective coating. A bare sensing electrode structure may generate an electric field between the electrodes that interacts directly with the fluid. A dielectric protective coated sensing electrode structure may generate an electric field that is between the electrodes that interacts with the fluid after penetrating through the dielectric protective coating. In one embodiment, the coating may be applied onto electrodes to form a conformal protective layer having the same thickness over all electrode surfaces and between electrodes on the substrate. Where a coating has been applied onto electrodes to form a protective layer, it may have a generally constant or variable final thickness over the substrate and sensor electrodes on the substrate. In another embodiment, a substrate simultaneously serves as a protective layer when the electrodes are separated from the fluid by the substrate. In this scenario, a substrate has electrodes on one side that may be not directly contact the fluid such that the other side of the substrate does not have electrodes that face the fluid. Detection of the fluid may be performed when the electric field from the electrodes penetrates the substrate and into the fluid. Suitable examples of such substrate materials may include ceramic, aluminum oxide, zirconium oxide, and others.

Figure 3:
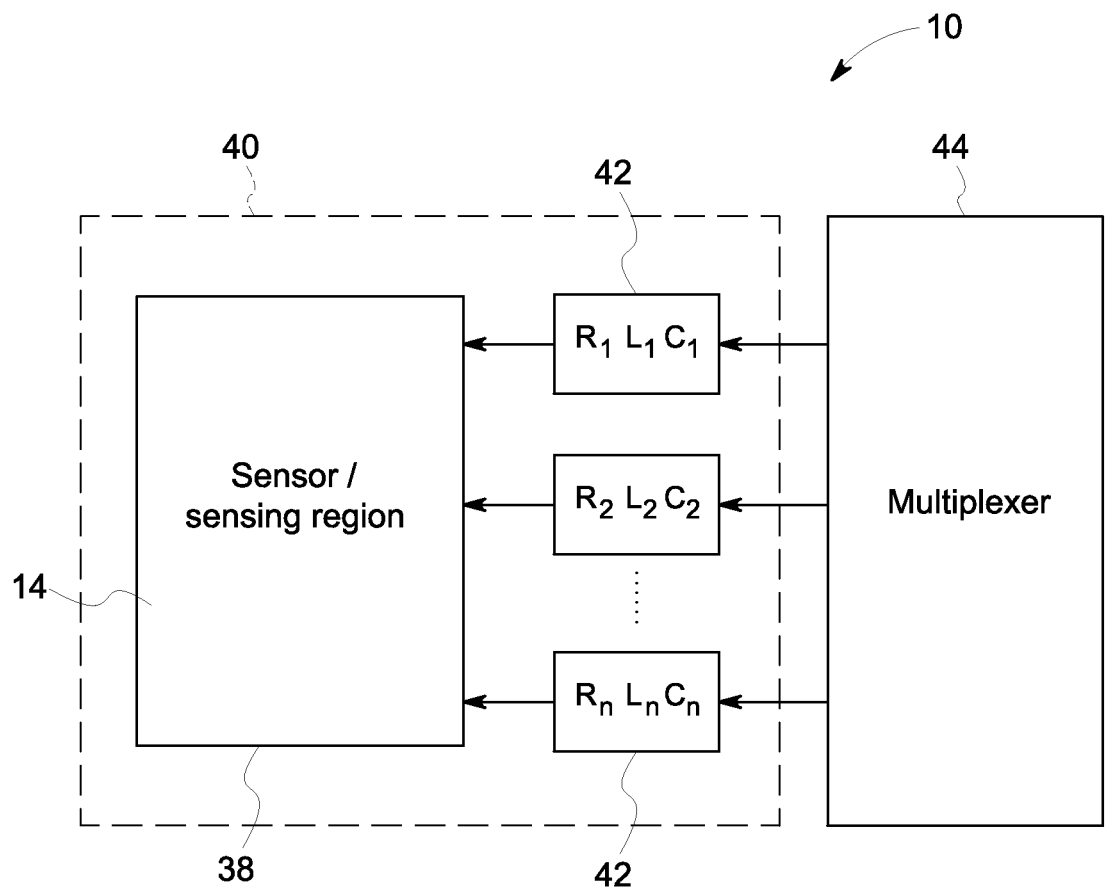
FIG. 3 is a schematic view of a portion of an example sensor system employing a sensor assembly configured for sensing of an fluid using a plurality of frequencies, in accordance with embodiments of the present disclosure.

FIG. 3 illustrates a portion of a resonant sensor system having a single sensing region 38, and employed in a sensor assembly 40 useful to probe a fluid sample using a plurality of frequencies. The sensing region may be disposed on a substrate and may include a suitable sensing material. In some embodiments, the substrate of the sensor may be a dielectric substrate. In some embodiments, the sensor assembly may include a plurality of tuning elements 42. The plurality of tuning elements may be operatively coupled to the single sensing region to define a plurality of resonant circuits. The tuning elements along with the single sensing region may define a plurality of resonant circuits. Each resonant circuit of the plurality of resonant circuits may include one or more tuning elements of the plurality of tuning elements. Not shown is a semi-permeable film, semi-permeable membrane, or semi-permeable inorganic barrier (collectively a "selective barrier") that allows (or prevents) selective analytes or contaminants through the selective barrier and into the sensing region.

Suitable interdigital electrode structures include two- and four-electrode structures. Suitable materials for electrodes include stainless steel, platinum, gold, noble metals, and others. Suitable materials of a substrate and/or a dielectric protective layer may include silicon dioxide, silicon nitride, parylene, silicone, fluorinated polymers, alumina, ceramics, and others. Suitable electrodes may be formed using metal etching, screen-printing, ink-jet-printing, and mask-based metal deposition techniques. The thickness of fabricated electrodes on the substrates may be in a range of from about 10 nanometers to about 1000 micrometers. The materials for the interdigital electrode structures, substrate, dielectric protective layer, and electrode formation methods may be selected based at least in part on the application specific parameters.

As shown in the illustrated embodiment, the plurality of tuning elements may be disposed external to the sensor. However, in one embodiment, the tuning elements may be disposed on the substrate of the sensor. In another embodiment, some of the plurality of tuning elements may be external to the sensor substrate, while other tuning elements may be disposed on the substrate. The tuning elements may comprise a resistor, a capacitor, an inductor, a resonator, impedance transformer, or combinations thereof.

The sensor assembly 10 may include a controller that has a multiplexer 44. The multiplexer may facilitate electronic switching between the plurality of tuning elements. The multiplexer may select one or more signals associated with the probing frequencies and forward the selected signal to an output device or a reader. In one embodiment, the multiplexer may selectively send signals to an output device or a reader. The multiplexer may send a plurality of signals simultaneously to a sensor reader. The multiplexer may facilitate electronic switching between the plurality of sensing regions.

During operation, each resonant circuit may resonate at a defined frequency. At least one resonant circuit may resonate at a frequency that may be different from the resonating frequency of the other resonant circuits. By way of example, if the sensing region includes a pair of electrodes, the tuning elements may be a resistor, a capacitor, and an inductor to form an inductor-capacitor-resistor (LCR) resonant circuit. The tuning elements may be electrically coupled to the sensing region. In one embodiment, the tuning elements may be in parallel connection to the sensing region. In certain embodiments, the different resonant circuits of the plurality of resonant circuits may be configured to resonate at different frequencies. The different resonant circuits may be configured to probe the fluid sample with a plurality of resonant frequencies. The different resonant frequencies may be used to probe a fluid sample over the frequency range of spectral dispersions. The spectral dispersions that may be monitored with the sensors of the present disclosure may be over a frequency range of from about 0.1 Hz to about 100 GHz and include alpha, beta, gamma, delta, and other types of spectral dispersions as constrained by application specific parameters.

Figure 4:
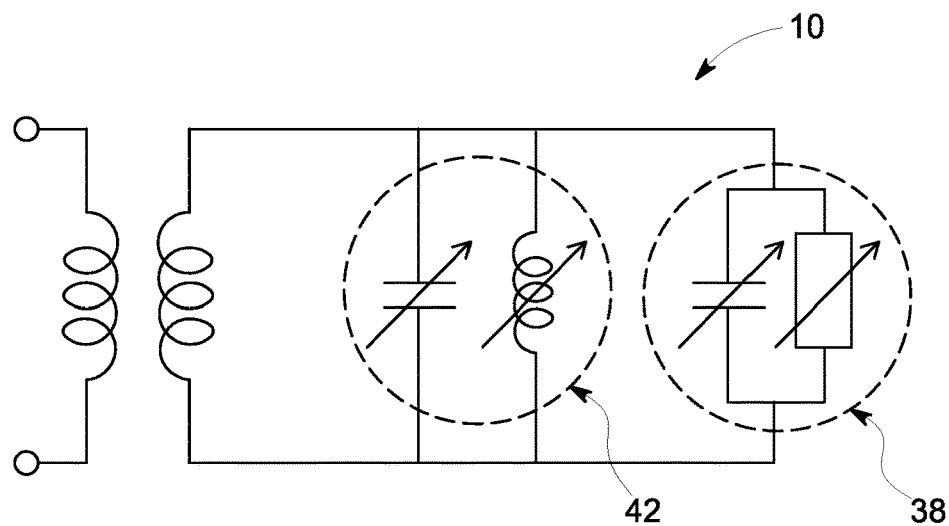
FIG. 4 is an example of an equivalent circuit of the resonant sensor according to an embodiment of the disclosure.

FIG. 4 illustrates another sensor circuit 10. The sensing region 38 (shown with variable resistor and capacitor) is combined with tuning components 42 (shown with variable inductance and capacitance). To realize sensor response at different frequency range, additional circuit elements may be utilized to tune the frequency range. Therefore, a sensor can be operating at multiple frequency ranges by using a defined or selected combination of extra circuit components—such as inductors, capacitors, and impedance transformers. These components may be connected in parallel or in series, as needed, to the sensor to vary the operating frequency range. The controller may control the impedance transformer ratio to affect the sensitivity. A sensor's frequency response and its magnitude may be based at least in part on the overall input resonant impedance changes due to the sensor's response to the cell's status, its behavior, and the like. Thus, the sensor's sensitivity may be controlled through the dynamic tunability of the transformer ratio. Tuning the response of each channel may be achieved, for example, by using one or more inductors. In one embodiment, wireless readout from the electrodes may provide an improvement in response selectivity and sensitivity. In one embodiment, transformer based coupling may reject parasitic LCR components from instrumentation (analyzer, cables, amongst others). The LCR resonator in FIG. 4 has a relatively simple design as compared to other resonators, for example as compared to marginal oscillators that require complicated multi-component circuits for their operation that include a current feedback amplifier and other components.

Figure 5A:
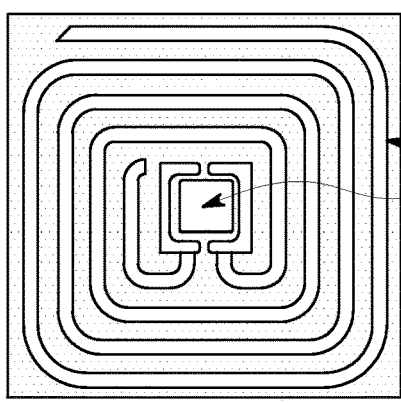
FIG. 5A is an example of an adapted RFID tag for resonant sensing in which the sensing region constitutes a whole or a portion of the resonant antenna according to an embodiment of the disclosure.
Figure 5B:
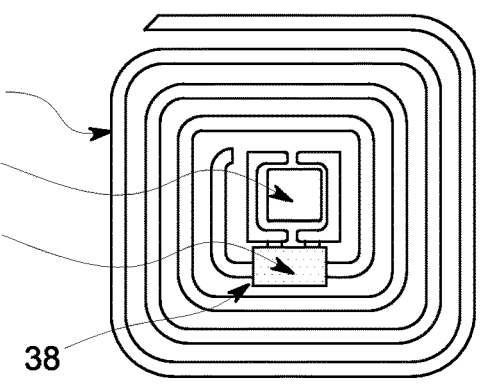
FIG. 5B is an example of an adapted RFID tag for resonant sensing in which the sensing region is in galvanic contact with the antenna and memory chip according to an embodiment of the disclosure.

As noted herein, a suitable wireless sensor may be radio-frequency identification (RFID) sensor where a passive RFID tag may be adapted to perform a sensing function. With reference to FIGS. 5A and 5B, an embodiment is shown in which the resonant sensor may be an adapted RFID tag. In FIG. 5A a resonant antenna 50 and memory chip 52 may be coated with a protective material or sensing material 56. The sensing material may be a sensing region of the RFID tag. In FIG. 5B, the sensing region (that can optionally include the protective or sensing material) may be attached across an antenna. In both cases (FIGS. 5A and 5B), the electrical response of the sensing region may be translated into changes in the resonant impedance response of the sensor. An RFID sensor having a memory chip may operate with a frequency determined at least in part by the operating frequency used the memory chip. That is, some operating frequencies (of the sensor and the chip) may interfere with each other and may be less desirable to have disruptive harmonics or destructive waveforms. And, the sensor can have a circular, square, cylindrical, rectangular, or other appropriately-shaped sensing region and/or antenna.

The resonant frequency of an antenna circuit may be set to a higher frequency than a resonant frequency of the sensor circuit. The frequency differential may be in a range of from, for example, as much as about 4 times to about 1000 times higher. In one embodiment, the sensor circuit may have a resonant frequency that may respond to a determined sensed environmental condition. The two resonant circuits may be connected so that when alternating current (AC) energy is received by the antenna resonant circuit, it may apply direct current energy to the sensor resonant circuit. The AC energy may be supplied through the use of a diode and a capacitor, and the AC energy may be transmitted to the sensor resonant circuit through an LC tank circuit through either a tap within the L of the LC tank circuit or a tap within the C of the LC tank circuit. Further, the two resonant circuits may be coupled such that voltage from the sensor resonant circuit may change the impedance of the antenna resonant circuit. The modulation of the impedance of the antenna circuit may be accomplished through the use of a transistor, for example a FET (field-effect transistor).

The RFID sensor's memory chip may be optional. The RFID sensor without a memory chip can be a resonant LCR sensor and can operate at different frequency ranges from a kilohertz to a gigahertz. That is, the memory chip's absence may widen the available frequency range.

Suitable sensing materials and sensing films as disclosed herein may include materials deposited onto the sensor to perform a function of predictably and reproducibly affecting the resonant impedance sensor response upon interaction with the environment. For example, a conducting polymer, such as polyaniline, changes its conductivity upon exposure to solutions of different pH. That is, the resonant impedance sensor response changes as a function of pH when such a conducting polymer film is deposited onto the RFID sensor surface. Thus, such an RFID sensor works as a pH sensor.

As an example of gaseous fluid detection, when such a polyaniline film is deposited onto the RFID sensor for detection in gas phase, the complex resonant impedance sensor response also changes upon exposure to basic (for example, $NH_3$) or acidic (for example, HCl) gases. Suitable sensor films include polymer, organic, inorganic, biological, composite, and nano-composite films that change their electrical and or dielectric property based on the environment in which they may be placed. Other examples of sensor films may be a sulfonated polymer such as commercially available Nafion, an adhesive polymer such as silicone adhesive, an inorganic film such as sol-gel film, a composite film such as carbon black-polyisobutylene film, a nano-composite film such as carbon nanotube-Nafion film, gold nanoparticle-polymer film, metal nanoparticle-polymer film, zeolites, metal-organic frameworks, cage compounds, clathrates, inclusion compounds, electrospun polymer nanofibers, electrospun inorganic nanofibers, electrospun composite nanofibers, and other sensor materials selected based on application specific parameters. To reduce or prevent the material in the sensor film from leaking into the liquid environment, the sensor materials may be attached to the sensor surface using standard techniques, such as covalent bonding, electrostatic bonding and other techniques.

In one embodiment, the system may measure a resonant impedance (f) (represented by Eq. (1)) of the sensor.

$$\check{Z}(f)=Z_{re}(f)+jZ_{im}(f) \quad \text{Eq. (1)}$$

where $Z_{re}(f)$ may be the real part of the resonant impedance and $Z_{im}(f)$ may be an imaginary part of the resonant impedance. In one embodiment, the resonant impedance response of the sensor may be a multivariable response as more than one frequency may be utilized to measure sensor response across the resonance of the sensor. In some embodiments, the resonant impedance response of the sensor may be a multivariable response because more than one frequency may be utilized to measure sensor response outside the resonance peak of the sensor. In some embodiments, the sensor response may be measured at multiple frequencies across the resonance of the sensor. For example, if the sensor resonates at about 1 MHz, the measured frequencies and associated sensor responses may be measured from about 0.25 MHz to about 2 MHz. This multivariable response may be analyzed by multivariate analysis. The multivariable response of the sensor includes the sensor's full resonant impedance spectra and/or several individually measured properties, such as but not limited to $F_p$, $Z_p$, $F_z$, $F_1$, $F_2$, $Z_1$, and $Z_2$.

Figure 6:
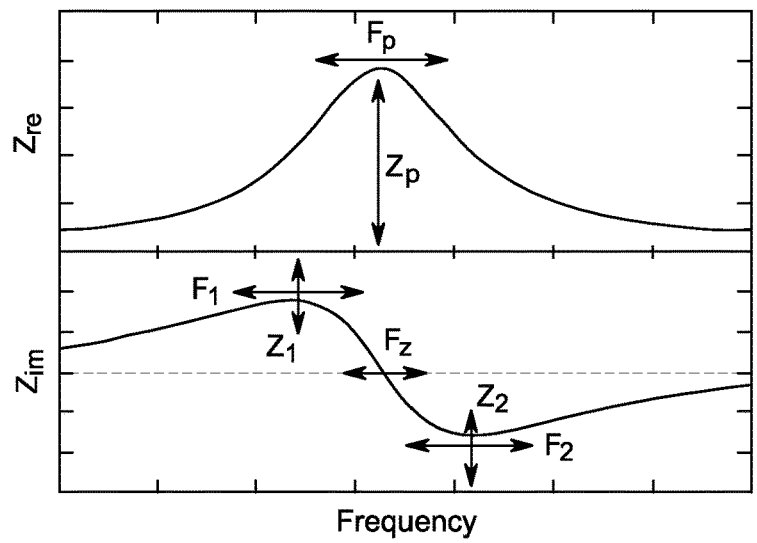
FIG. 6 is a graph of measured resonant impedance parameters of an embodiment of the resonant sensor, in accordance with embodiments of the present technique.

FIG. 6 depicts a graph of measured resonant impedance parameters of an embodiment of the resonant sensor, in accordance with embodiments of the present technique. These and other measured properties may be "spectral parameters." These properties include the frequency of the maximum of the real part of the resonant impedance ($F_p$, resonance peak position), magnitude of the real part of the resonant impedance ($Z_p$, peak height), zero-reactance frequency ($F_z$, frequency at which the imaginary portion of resonant impedance may be zero), resonant frequency of the imaginary part of the resonant impedance ($F_1$), and anti-resonant frequency of the imaginary part of the resonant impedance ($F_2$), signal magnitude ($Z_1$) at the resonant frequency of the imaginary part of the resonant impedance ($F_1$), and signal magnitude ($Z_2$) at the anti-resonant frequency of the imaginary part of the resonant impedance ($F_2$). Other parameters may be measured using the entire resonant impedance spectra, for example, quality factor of resonance, phase angle, and magnitude of resonant impedance.

Figure 7A:
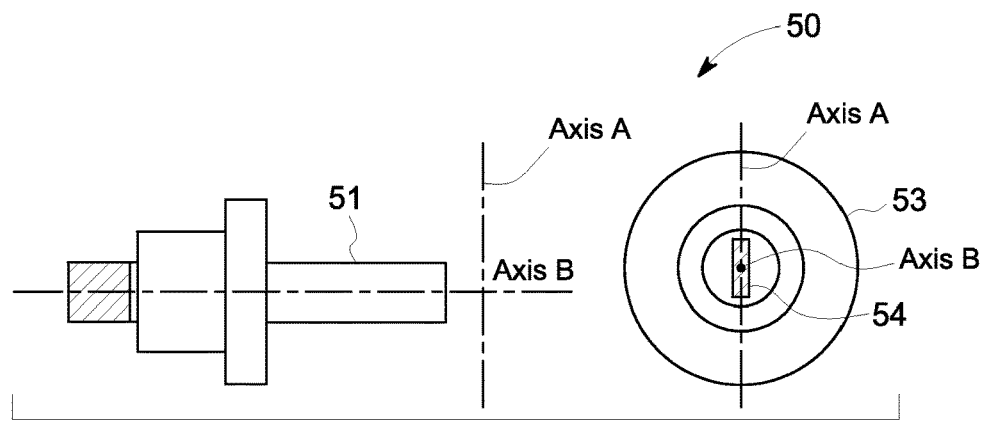
FIG. 7A is an example of a resonant sensor in which the sensing region is arranged parallel to the sensor axis insertion into the measured fluid, and therefore, perpendicular to the insertion port of the sensor according to an embodiment of the disclosure.
Figure 7B:
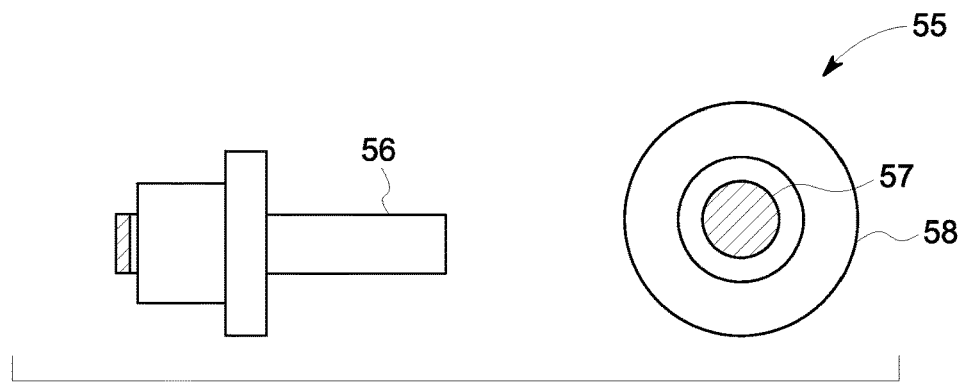
FIG. 7B is an example of a resonant sensor in which the sensing region is arranged perpendicular to the sensor axis insertion into the measured fluid, and therefore, parallel to the insertion port of the sensor according to an embodiment of the disclosure.

For measurements of fluid properties in fluid reservoirs, sensors with their sensing regions can be designed to fit standard ports or specially made ports in the reservoirs. Suitable design examples are depicted in FIG. 7A and FIG. 7B. An example is provided of a resonant sensor 50 with an aligned sensing region 51. The sensing region defines a first Axis A, which is perpendicular to a transverse axis labeled Axis B. An insertion port structure 53 defines an insertion aperture 54 that is elongated along Axis A. The sensing region, then, is arranged parallel to the port's elongated aperture, translation along Axis B allows for sensor region insertion into the port and to contact a measured fluid. An example of another resonant sensor 55 in which the sensing region 56 is not constrained by its shape relative to an aperture 57 defined by a port structure 58 is depicted in FIG. 7B. Alignment pins, not shown, may be used to align the sensor, and the sensing region, relative to the port aperture, as may be desired.

Figure 8A:
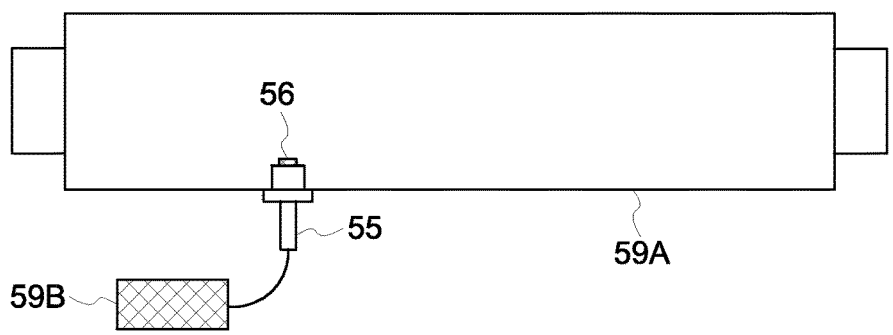
FIG. 8A is an example of sensing of fluid properties with a sensor in a fluid reservoir when the sensor is incorporated into the reservoir with the sensing region of the sensor exposed to the fluid and the sensor reader located near the sensor and connected to the sensor with a cable according to an embodiment of the disclosure.
Figure 8B:
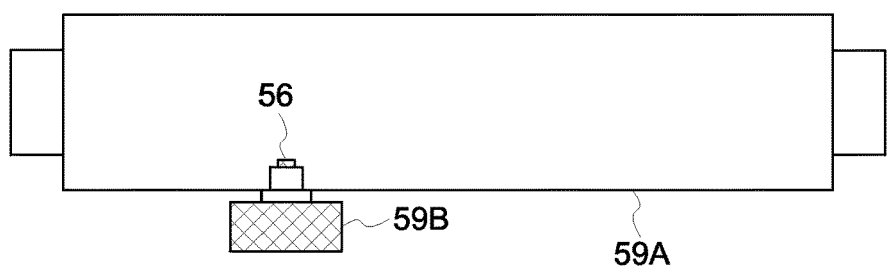
FIG. 8B is an example of sensing of fluid properties with a sensor in a fluid reservoir when the sensor is incorporated into the reservoir with the sensing region of the sensor exposed to the fluid and the sensor reader directly connected to the sensor according to an embodiment of the disclosure.

Measurements of fluid properties in fluid reservoirs may be performed using sensors with their sensing regions exposed to the fluid as shown in FIGS. 8A and 8B. The sensor shown in FIG. 7B is installed in a fluid transfer pipe 59A, and is coupled to a sensor reader 59B. The sensor reader may be coupled by wire or cable, and located proximate to the sensor as shown in FIG. 8A. In another embodiment, the sensor reader may be directly connected to the sensor without a cable—as shown in FIG. 8B. During operation, a fluid flows through the pipe and contacts the sensing region. As the sensing region senses an analyte of interest it signals the sensor reader.

Figure 9:
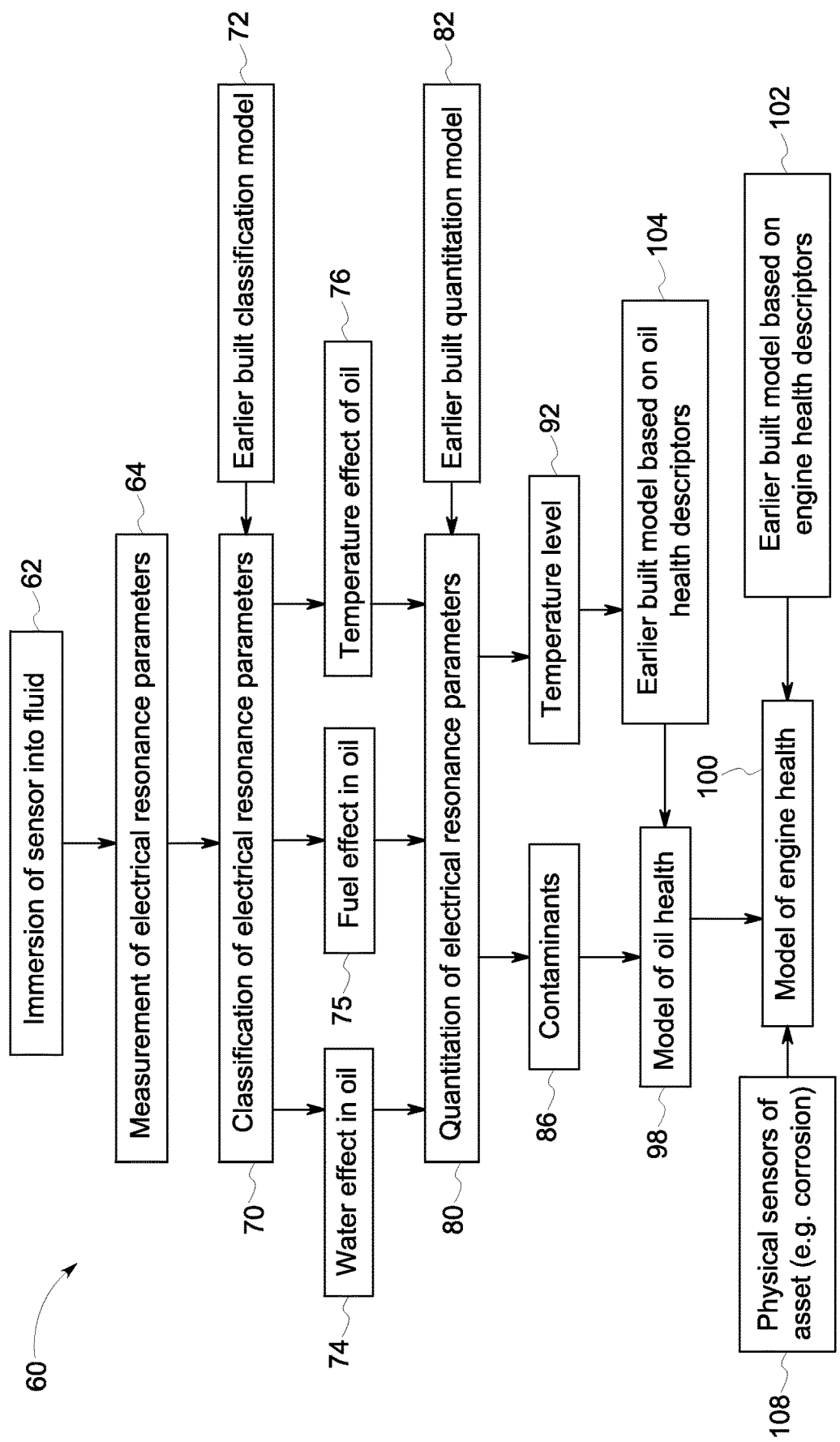
FIG. 9 is a flow diagram of fluid assessment according to an embodiment of the disclosure.

A flow diagram of a method 60 is shown in FIG. 9. In one embodiment, a method for monitoring of oil health includes immersion of the sensor into an fluid, such as oil (step 62) and measurement of the electrical resonance parameters of the resonance spectra (step 64) at several resonances of a single sensor. For quantitation of contamination of engine oil by water, fuel leaks, and soot with a sensor, the sensor may be placed into operational contact with the fluid at step 62. In a specific embodiment, the resonant impedance spectra $(f)=Z_{re}(f)+jZ_{im}(f)$ of a sensor such as a sensor may be determined at step 64. For example, the parameters from the measured (f) spectra such as the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_Z$ of $Z_{im}(f)$, may be calculated.

The method 60 classifies the electrical resonance parameters at step 70. This may be done using a determined classification model 72 to assess, for example, one or more of water effects 74, fuel effects 75, and temperature effects 76. Quantitation of the electrical resonance parameters may be performed at step 80 by using a predetermined, earlier saved quantitation model 82, and determination of components 86 in oil such as water, fuel, soot, and wear metal particles 90 as well as the temperature 92, and prediction of the oil health 98 and the engine health 100. This may be done by using one or more of determined engine health descriptors 102 and oil health descriptors 104 as well as inputs from any additional sensors 108. Suitable additional sensors may include those sensing corrosion, temperature, pressure, system (engine) load, system location (e.g., by GPS signal), equipment age calculator, pH, and the like.

For example, in one embodiment, a sensor system may be an electrical resonator that may be excited with a wired or wireless excitation and where a resonance spectrum may be collected and analyzed to extract at least four parameter that may be further processed upon auto scaling or mean centering of the parameters and to quantitatively predict the concentrations of water and fuel in engine oil and to predict the remaining life of the engine oil and/or the remaining life of the engine. The spectral response of the resonance spectrum such as $F_p$, $Z_p$, $F_z$, $F_1$, $F_2$, $Z_1$, and $Z_2$ or the whole resonance spectrum with a single or multiple resonators can be used for data processing.

The classification model (see model 72 in FIG. 9) may be built using the predicted contributions of the spectral parameters for an uncontaminated fluid and for fluid contamination using previously determined component effects and their corresponding spectral parameters. Such effects may be quantified (e.g., see quantitation model 82 in FIG. 9) to predict if a measured or sensed fluid has any water effects, fuel leak effects, or temperature effects. That is, based in previously or empirically determined effects of components on particular fluid, the resonance parameters, both real and imaginary, may be affected in a quantifiable manner if components of interest are present. Further, based on the measured parameters, a concentration of a particular component may also be predicted, and multi-component models may be generated. The disclosed techniques may be used to sense a suitable fluid and to build a component and environmental effect model.

In one embodiment, measurements of properties of fluids may be performed at two or more temperatures of the fluid. Measurements at different temperatures provide information about species of interest and other species (chemical constituents) in the fluid when measured as the frequency dispersion profiles over the broad frequency range or when measured as frequency responses over the relatively narrow frequency range. Performing analysis of resonant impedance spectra of the sensor collected at different temperatures and determining two or more properties of the fluid per temperature based on the analyzed resonant impedance spectra allows an improvement of the sensor accuracy of determinations of properties of species of interest. This improvement may be due to differences of frequency responses of species of interest and other species in the fluid as a function of temperature caused by the molecular structure of these different species. Measurements at different temperatures may be performed with a resonant sensor that has a thermal element in thermal contact with the sensing region of the resonant sensor. The thermal element produces a local change in temperature of the fluid which may be in proximity to the sensing region. This local temperature change can be above or below the temperature of the bulk of the fluid in the container with the sensor. Non-limiting examples of thermal elements include a Peltier cooler, thin-film heater, and pencil heater. The thermal element can produce a local change in temperature of the fluid in the range from about 1 degree Celsius to about 50 degrees Celsius.

In one embodiment, measurements of properties of fluids may be performed to determine dynamic signatures of the changes of chemical constituents in the fluid. The time scales of these dynamic signatures may vary greatly. Suitable timescale in a range of from about 1 second to about 200 days may be useful to determine different types of leaks of fluids in engines. Such determinations allow the identification of dynamic signatures of the leaks in an engine, relation of the identified signature with the known leak signature from a specific engine component, and determination of the location of the leak based on the signature.

Measurements of properties of fluids may be performed at extreme temperature conditions. Depending on the application, these conditions may range from temperatures down to about −260 degrees Celsius and to temperatures up to about +260 degrees Celsius. Such harsh temperature conditions with negative temperature down to about −260 degrees Celsius may be useful in relation to liquefied natural gas (LNG) and in the storage of biological and other types of samples. Harsh temperature conditions with positive temperature of up to about +260 degrees Celsius may be useful in monitoring equipment where the temperature of operating components of the equipment can reach about +260 degrees Celsius. Examples of such equipment may include downhole equipment in oil and gas production and the operations of an internal combustion engine (diesel, natural gas, hydrogen (direct combustion or fuel cells), gasoline, combinations thereof, and the like) for one or more of the fuel, the lubrication system, and the cooling/radiator system. Another example of such equipment may include an oil-filled transformer.

The applicability of multivariable electrical resonators may be demonstrated by detection of engine oil contamination from water and diesel fuel and determinations of water in model fluid such as dioxane that has the dielectric constant similar to oil. Determination of resolution of the sensor measurements may be performed using hexane and toluene as model systems. Samples of some engine oil were obtained from GE Transportation, while other chemicals may be commercially obtained from Aldrich.

Measurements of the resonant impedance of sensors may be performed with a network analyzer (Agilent) or a precision impedance analyzer (Agilent), under computer control using LabVIEW. Collected resonant impedance data may be analyzed using KaleidaGraph (Synergy Software, Reading, Pa.) and PLS_Toolbox (Eigenvector Research, Inc., Manson, Wash.) operated with Matlab (The Mathworks Inc., Natick, Mass.).

Different amounts of fuel and water leaks into oil may be determined quantitatively and experimentally with a single multivariable resonant sensor. Suitable oil may be railroad internal combustion engine oil. Suitable fuel may be diesel fuel. Binary and ternary mixtures of water and fuel in oil may be produced in different proportions. Concentrations of water may be 0, 0.1% and 0.2% (by volume). Concentrations of fuel may be 0, 3% and 6% (by volume).

Figure 10:
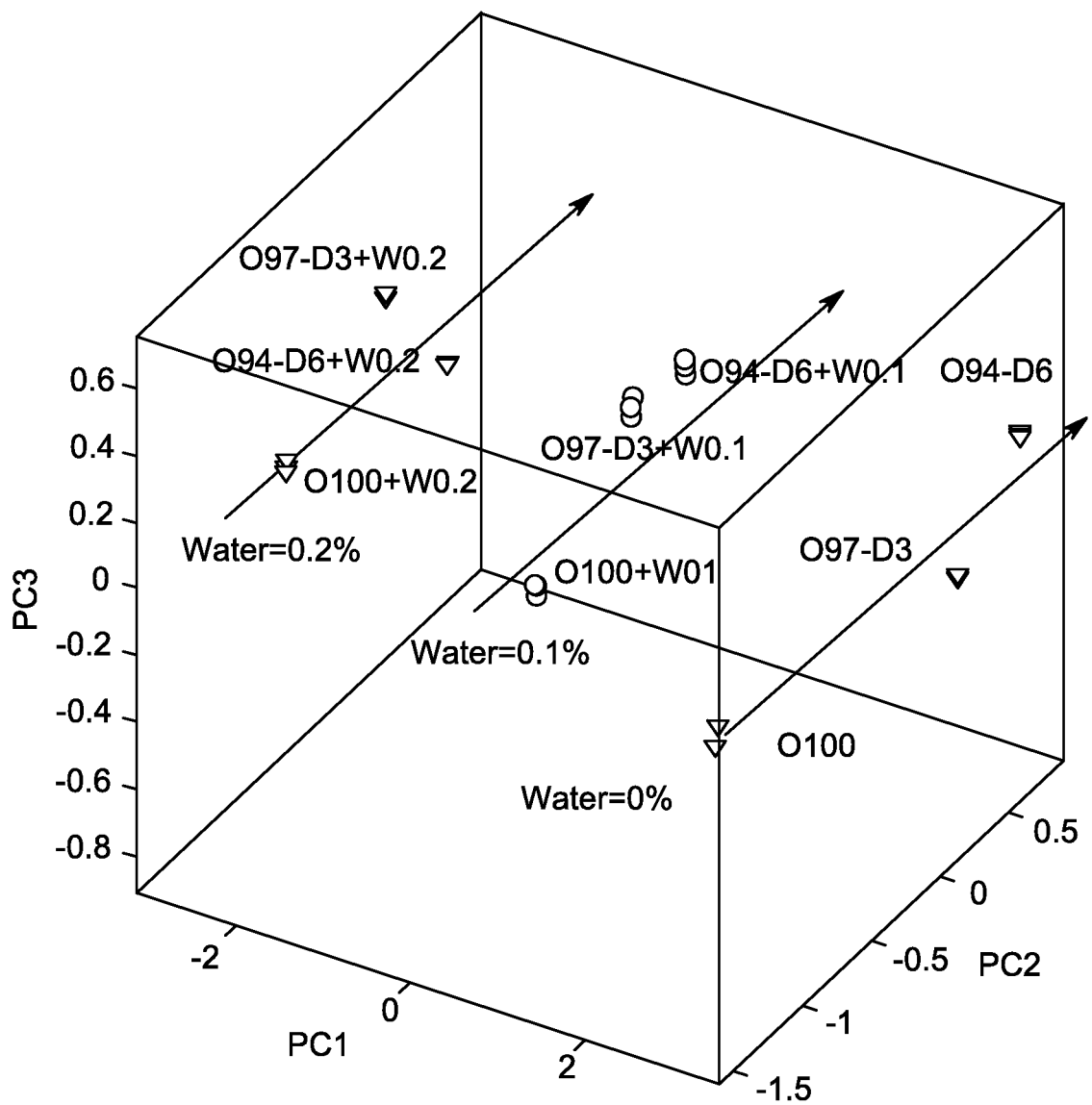
FIG. 10 is a plot of a resonant impedance data for detection of engine oil, water, and fuel with a highlighted water leak.
Figure 11:
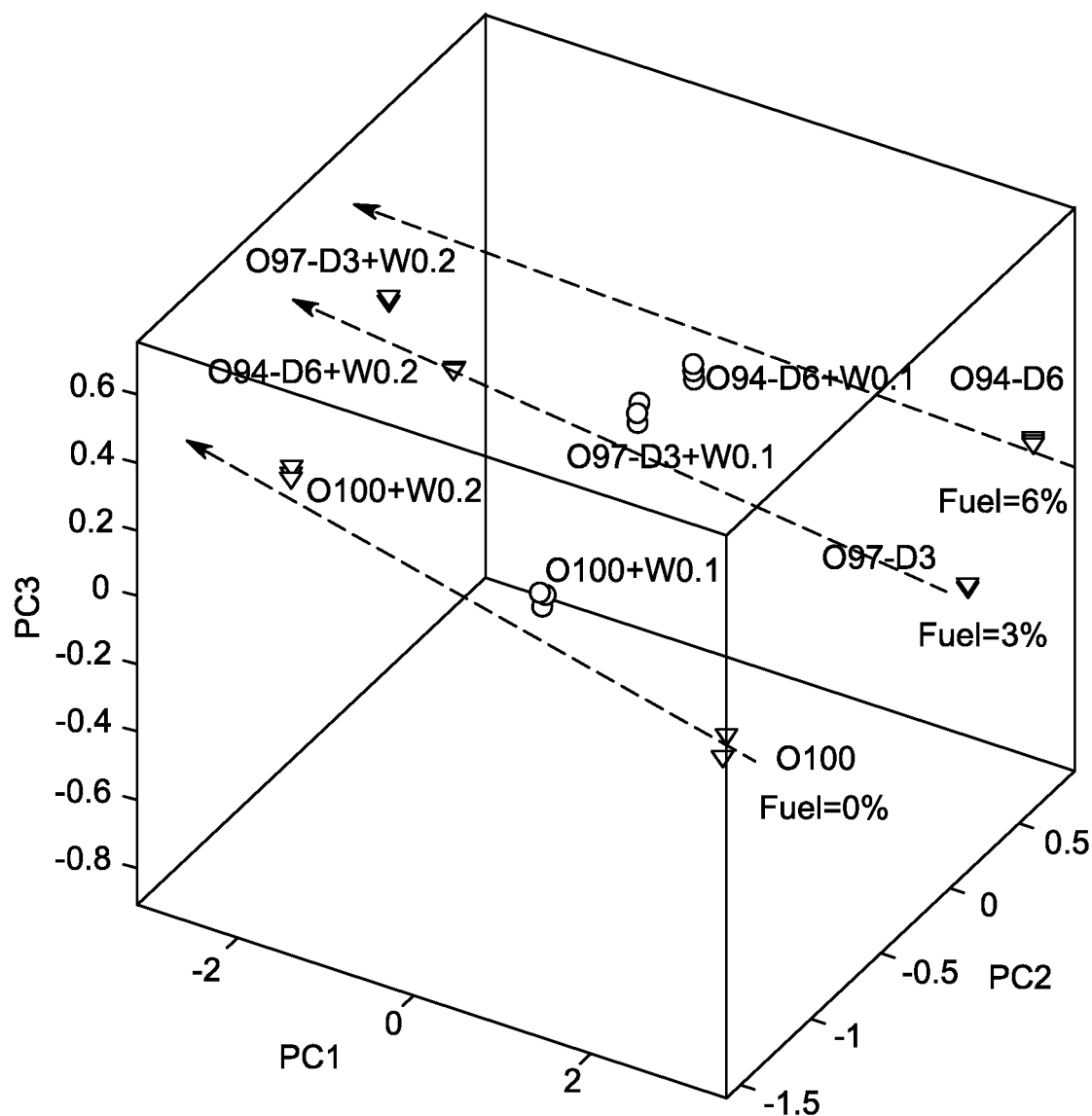
FIG. 11 is a plot of a resonant impedance data for detection of engine oil, water, and fuel with a highlighted fuel leak.

The resonance spectra from measured samples may be processed and the processed data served as inputs to the principal components analysis (PCA) tool. PCA may be a pattern recognition method that explains the variance of the data as the weighted sums of the original variables, known as principal components (PCs). A highlight of detection of water in mixtures of engine oil, water, and fuel may be illustrated in FIG. 10 that depicts a scores plot of a developed PCA model. A highlight of detection of fuel in mixtures of engine oil, water, and fuel may be illustrated in FIG. 11 that depicts a scores plot of a developed PCA model. In FIG. 10 and FIG. 11 concentrations of water of 0.1% and 0.2% are labeled as W0.1 and W0.2, respectively. Concentrations of fuel of 3% and 6% are labeled as D3 and D6, respectively. The multivariable response of the resonant transducers originates from the measured whole resonance spectra of the transducer followed by the processing of these spectra using multivariate analysis tools. For quantitation of contamination of engine oil by water and fuel leaks with a single multivariable sensor, the resonant impedance spectra $(f)=Z_{re}(f)+jZ_{im}(f)$ of the resonant transducer may be measured. Several parameters from the measured (f) spectra may be calculated that included the frequency position $F_p$ and magnitude $Z_p$ of $Z_{re}(f)$ and the resonant $F_1$ and antiresonant $F_2$ frequencies, their magnitudes $Z_1$ and $Z_2$ of $Z_{im}(f)$, and zero-reactance frequency $F_Z$ of $Z_{im}(f)$ as shown in FIG. 6.

Figure 12:
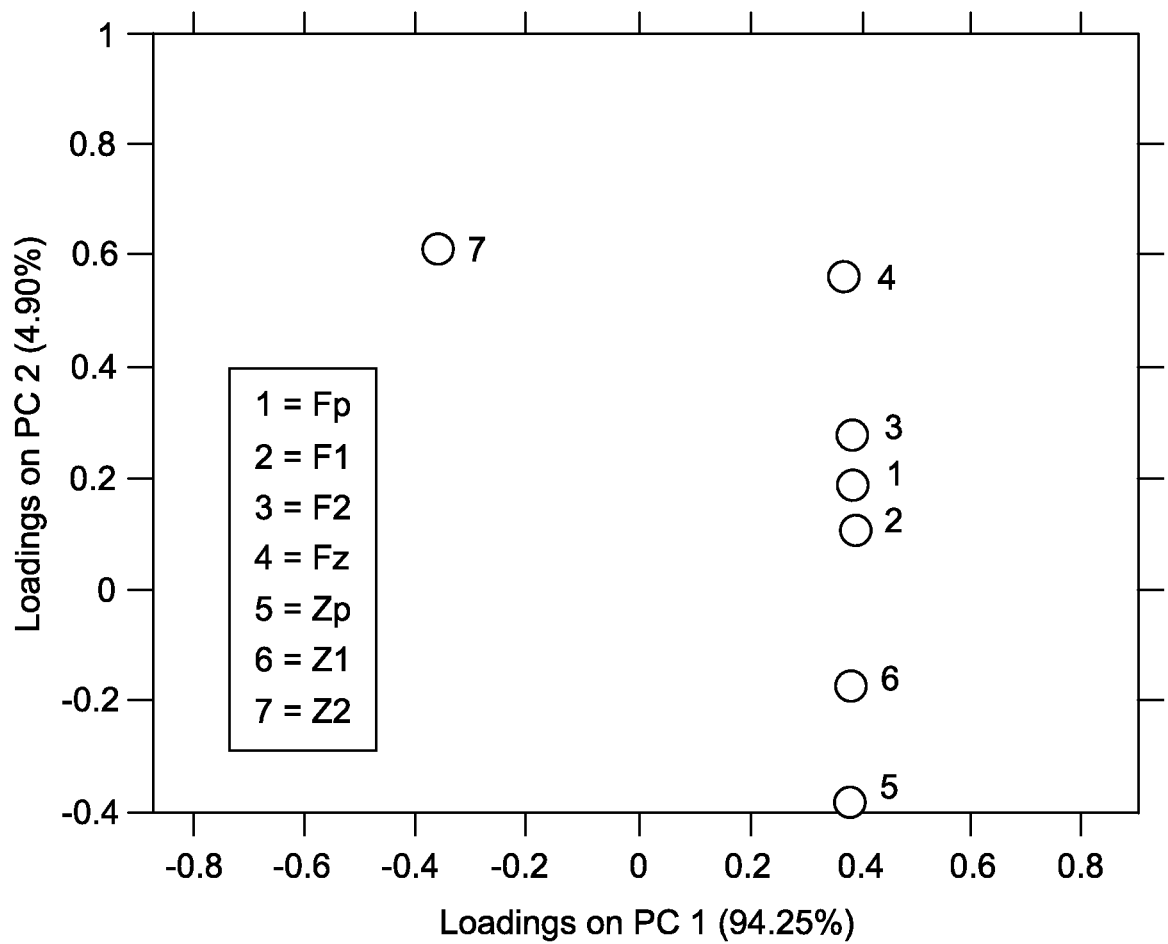
FIG. 12 is a principal components analysis of resonant impedance spectral parameters.

By using multivariate analysis of calculated parameters of (f) spectra, classification of analyte may be performed. Suitable analysis techniques for multivariate analysis of spectral data from the multivariable sensors may include Principal Components Analysis (PCA), Independent Component Analysis (ICA), Linear Discriminant Analysis (LDA), and Flexible Discriminant Analysis (FDA). PCA may be used to discriminate between different vapors using the peptide-based sensing material. A loadings plot of the PCA model in illustrated in FIG. 12. This plot illustrates the contributions of individual components from the resonance spectrum. The plot shows that all components such as Fp, F1, F2, Fz, Zp, Z1, and Z2 had contributions to the sensor response.

Figure 13:
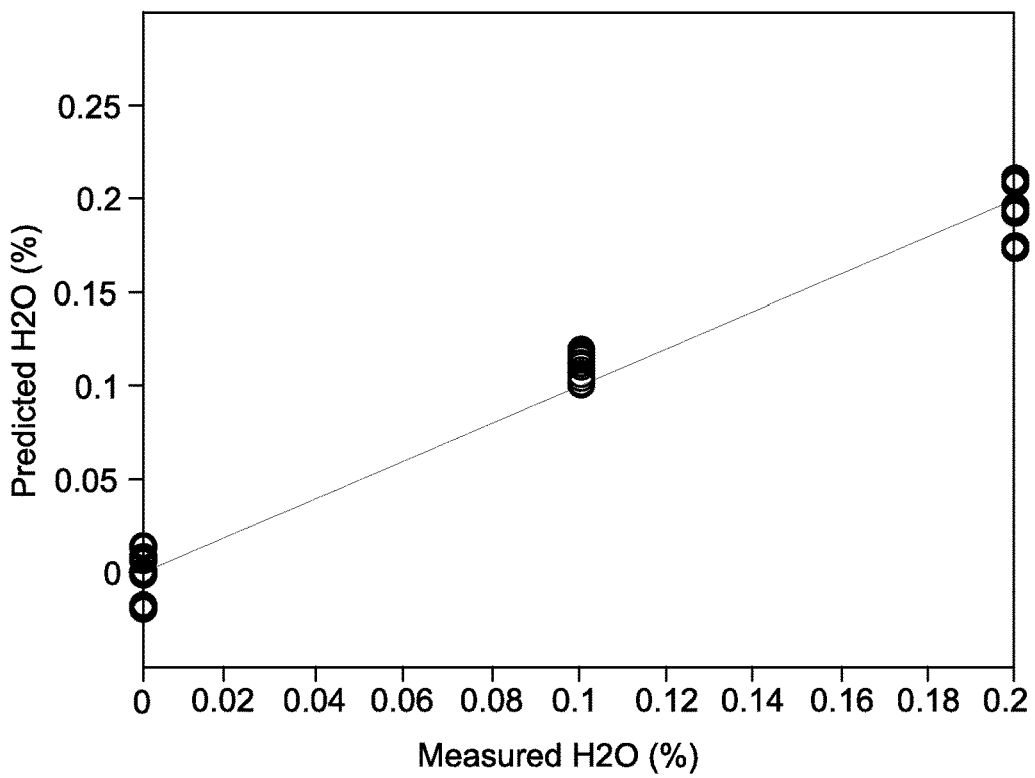
FIG. 13 is a correlation plot between the actual (measured) and predicted concentrations of water in water/fuel/oil mixtures using a single resonant sensor.
Figure 14:
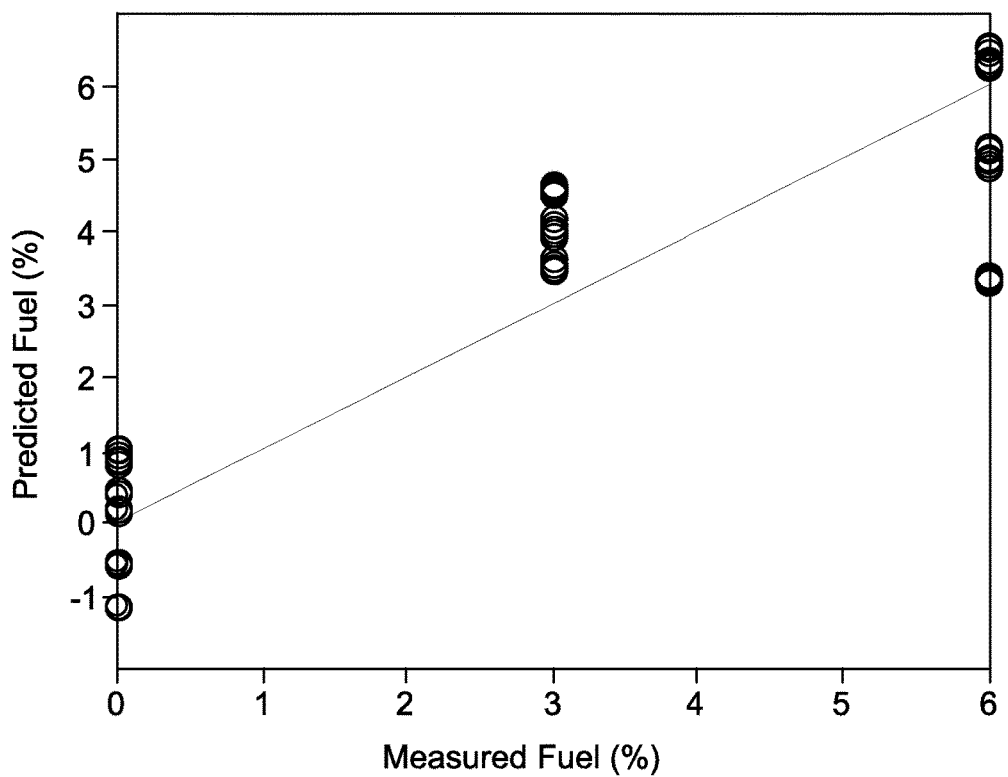
FIG. 14 is a correlation plot between the actual (measured) and predicted concentrations of fuel in water/fuel/oil mixtures using a single resonant sensor.

Quantitation of water and fuel in oil in their binary and ternary mixtures may be further performed with a single multivariable resonant sensor using PLS Toolbox (Eigenvector Research, Inc., Manson, Wash.) operated with Matlab (The Mathworks Inc., Natick, Mass.). FIG. 13 shows a correlation plot between actual (measured) and predicted concentrations of water in water/fuel/oil mixtures using a single resonant sensor. FIG. 14 shows a correlation plot between measured and predicted concentrations of fuel in water/fuel/oil mixtures using a single resonant sensor. Prediction errors of simultaneous quantitation of water and fuel in oil with the single sensor may be 0.02% of water and 1.3% of fuel.

Figure 15A:
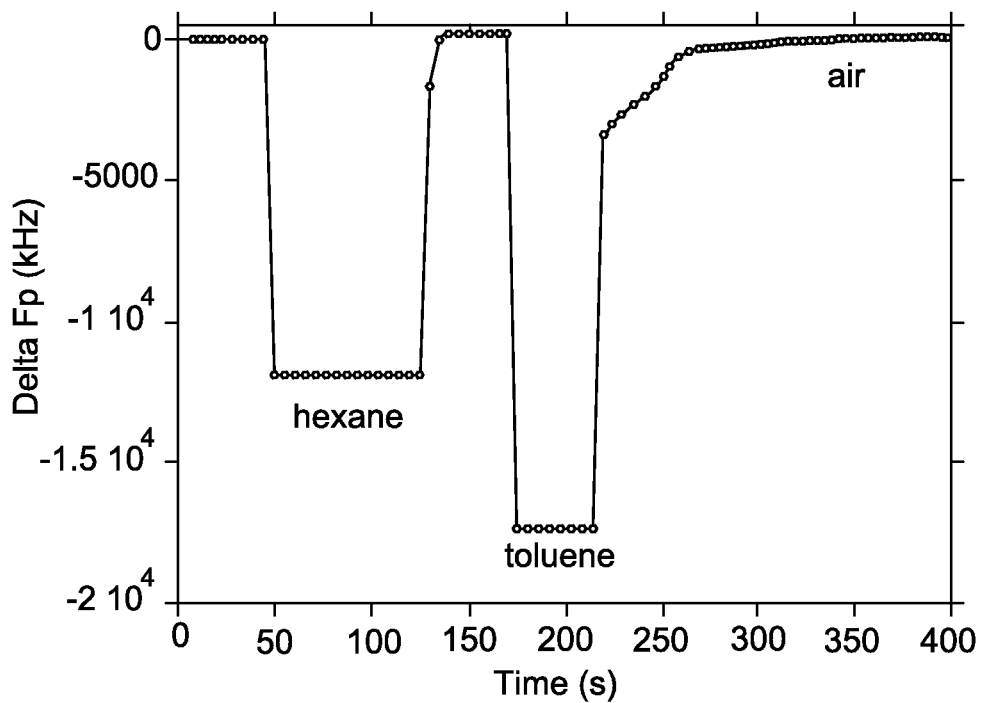
FIG. 15A is a plot of a spectral parameter showing resolution of a resonant sensor to distinguish between hexane and toluene.
Figure 15B:
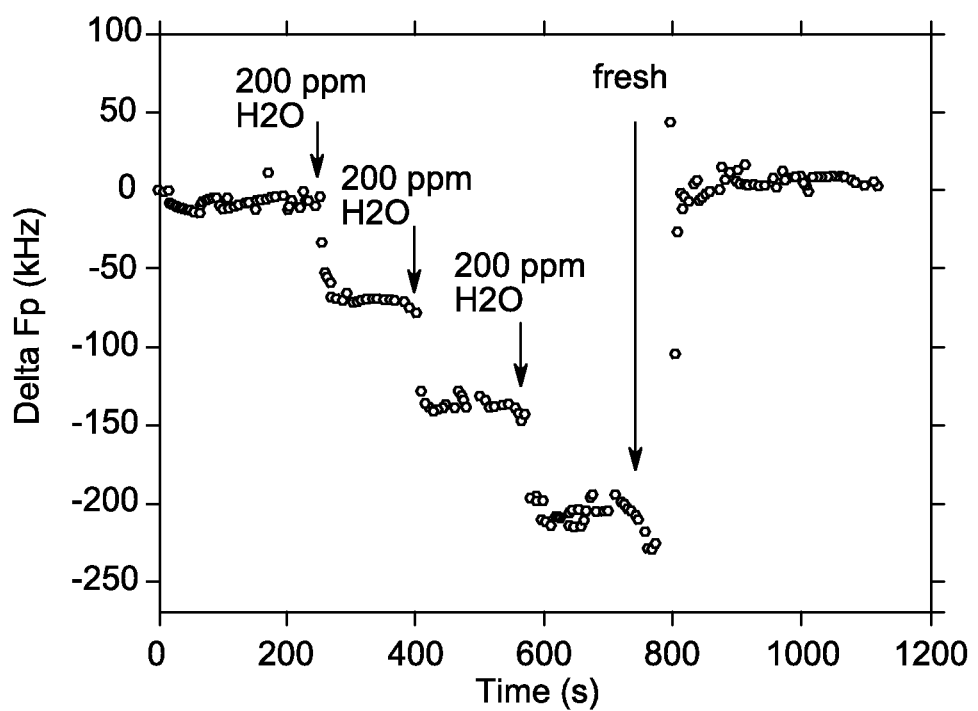
FIG. 15B is a plot of a spectral parameter showing resolution of water addition into dioxane.

In another example, sensor resolution may be determined in multi-part experiments. In a first experiment, hexane and toluene may be used as model chemicals to determine the ability of the sensor to resolve differences in the dielectric constant. Hexane has the dielectric constant of 1.88 while toluene has the dielectric constant of 2.38. A developed sensor may resolve these two liquids with the resolution of the dielectric constant of 0.0004-0.0012. Expected results are shown in FIG. 15A. In the second experiment, 1,4-dioxane may be used as a model chemical for oil because of its the dielectric constant similar to oil and the ability to be easily miscible with water. The sensor may resolve water additions into dioxane down to 7-20 ppm. Expected results are shown in FIG. 15B illustrating that the developed sensor may be able to resolve water additions into dioxane (model system for oil) down to 7-20 ppm with water additions done in increments of 200 ppm.

Figure 16A:
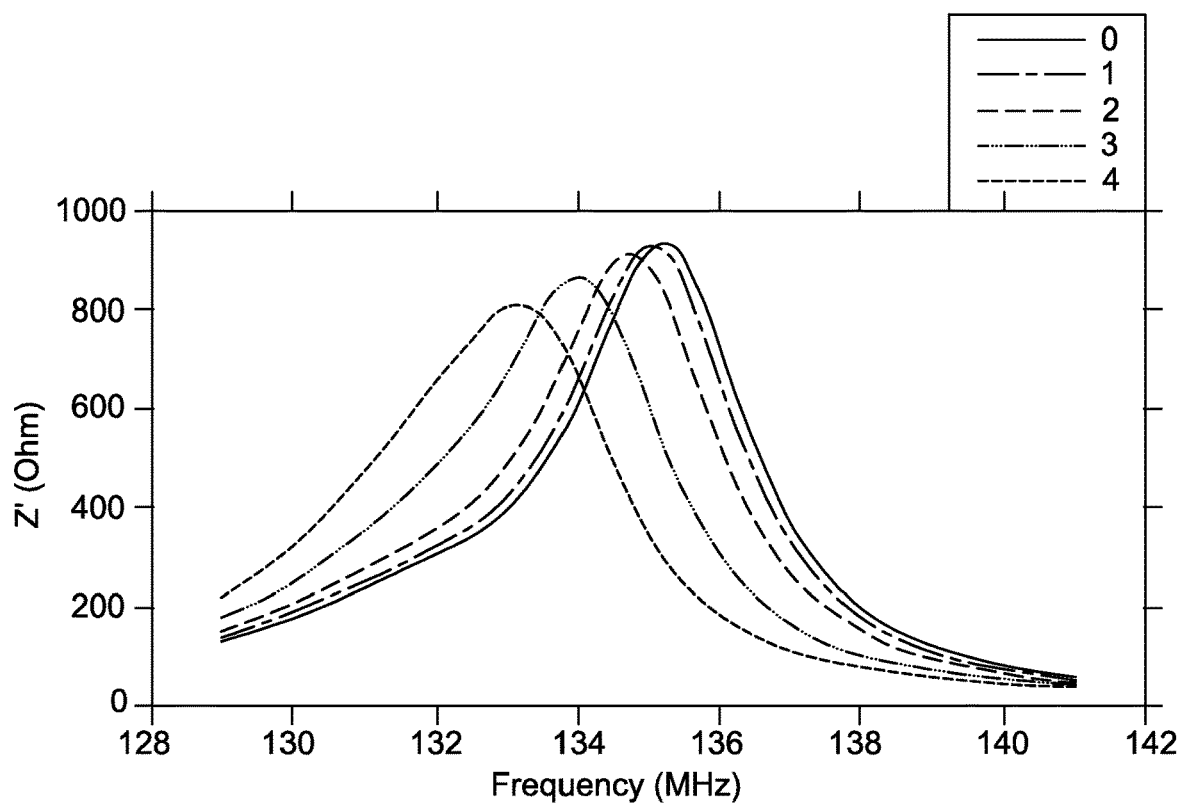
FIG. 16A is a plot of the real part of resonant impedance spectra after soot and water addition.
Figure 16B:
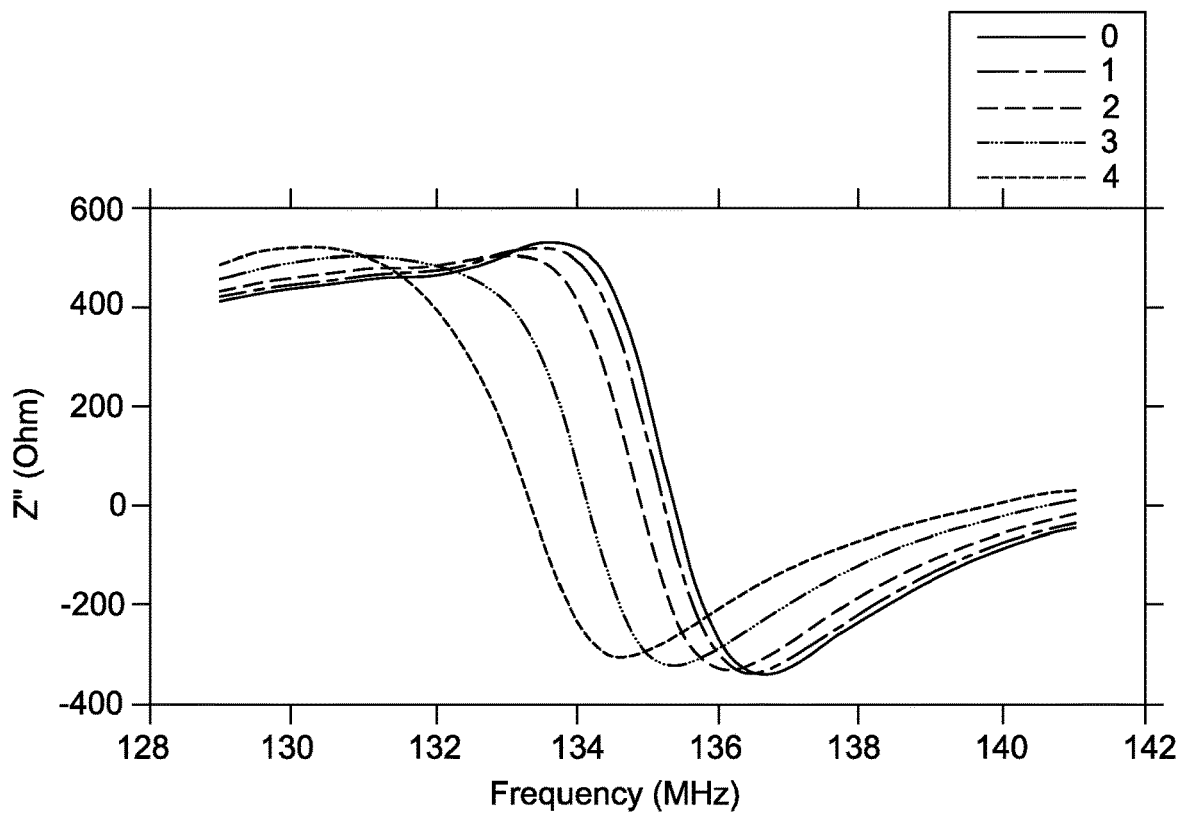
FIG. 16B is a plot of the imaginary part of resonant impedance spectra after soot and water addition.
Figure 17:
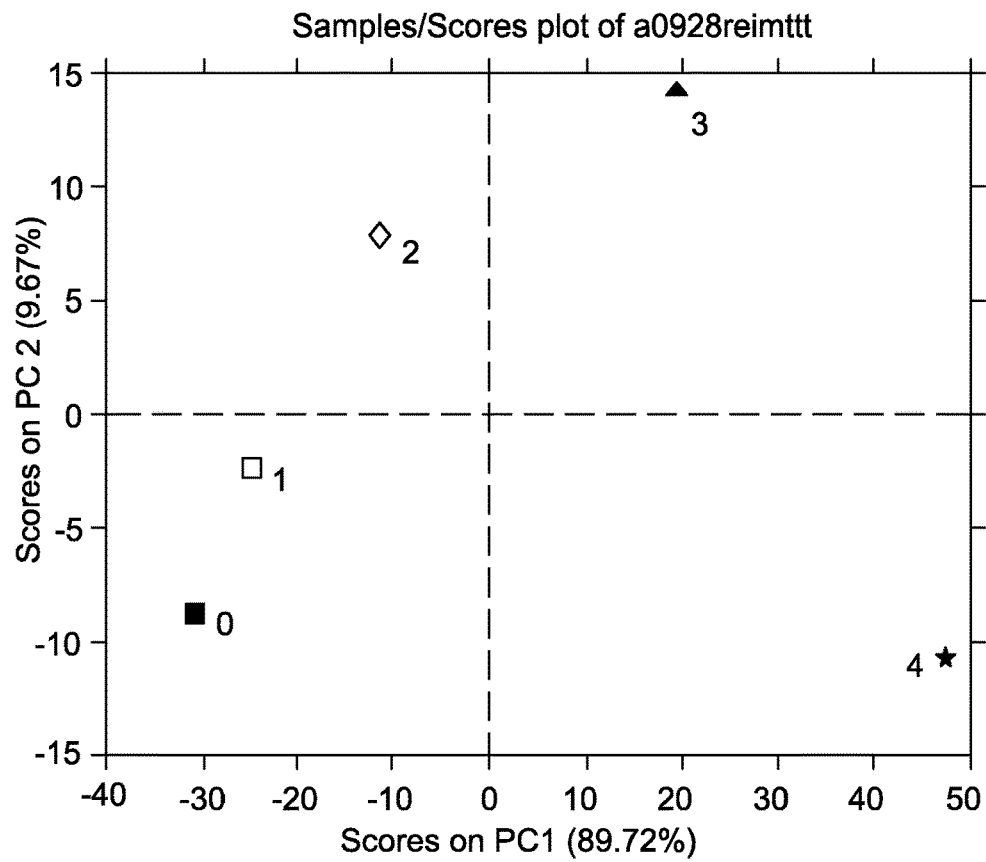
FIG. 17 depicts the PCA scores plot of PC1 vs. PC2 upon exposure of sensor to five solutions and performing resonance impedance measurements.

In another example, water and soot (carbon black) additions may be done to dioxane and measured with a sensor. Water additions may be done as 500 ppm, 1000 ppm, and 2500 ppm additions. Soot (carbon black) may be added as 100 ppm carbon black with 2500 ppm of water. Exemplary resonance spectra of a sensor are presented in FIGS. 16A and 16B. Results of multivariate analysis are presented in FIG. 17. FIG. 16A shows the real part $Z_{re}(f)$ and FIG. 16B shows imaginary part $Z_{im}(f)$ of resonant impedance. Measured samples may be: (0) clean model oil (dioxane); (1) addition of 500 ppm of water; (2) addition of 1000 ppm of water, (3) addition of 2500 ppm of water; (4) addition of 2500 ppm of water and 100 ppm of soot (carbon black). FIG. 17 shows Scores plot of Principal component 1 vs. Principal component 2 illustrating spectral relation between sensor responses to different types of contamination. Samples may be: (0) clean model oil (dioxane); (1) addition of 500 ppm of water; (2) addition of 1000 ppm of water; (3) addition of 2500 ppm of water; (4) addition of 2500 ppm of water and 100 ppm of soot (as carbon black).

Figure 18A:
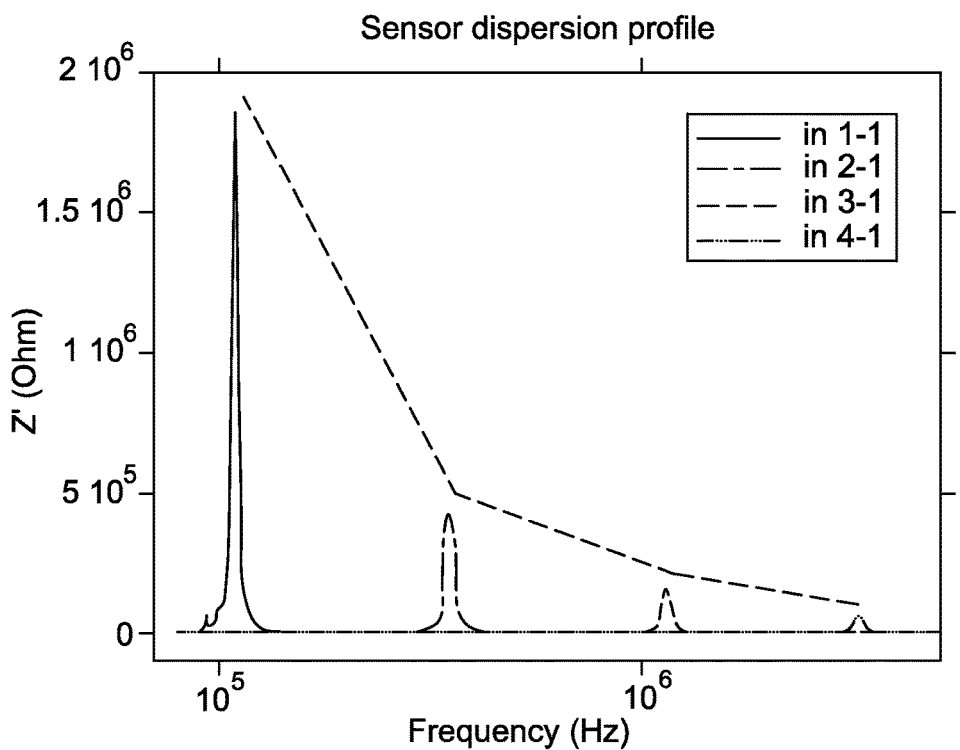
FIG. 18A displays a plot of four resonant spectral profiles from a single sensor for uncontaminated dioxane.
Figure 18B:
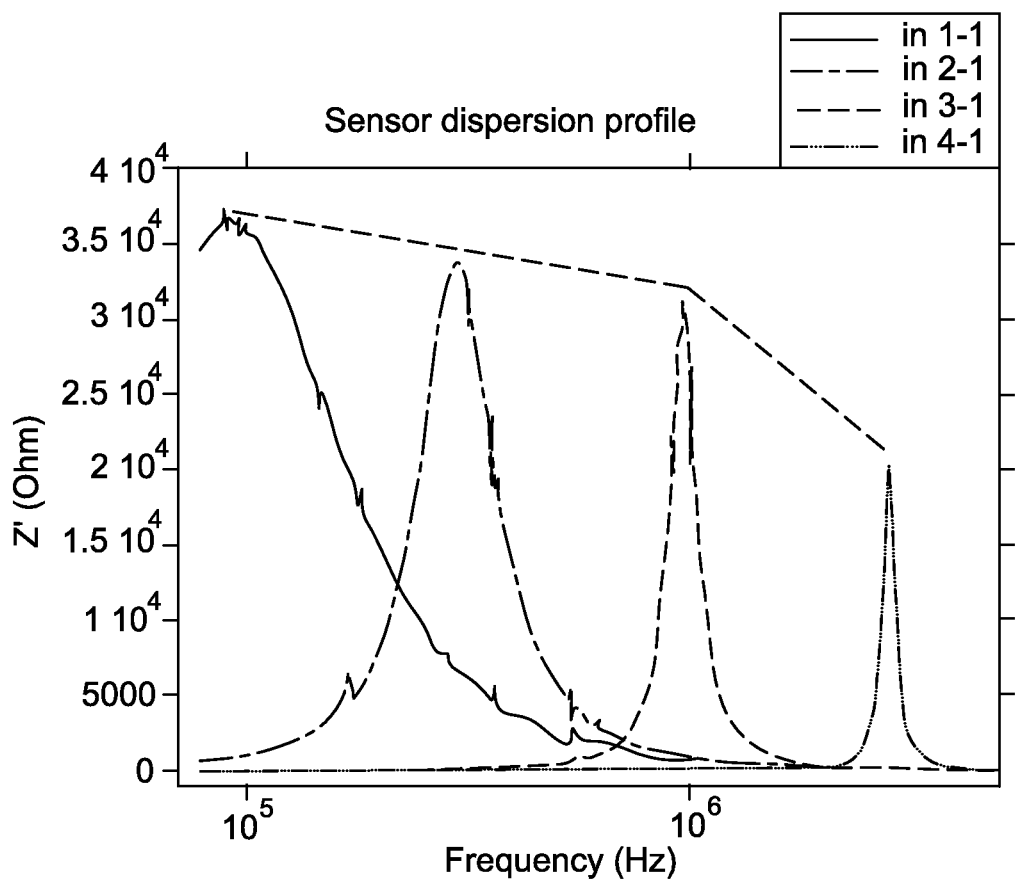
FIG. 18B displays a plot of resonant spectral profiles from a single sensor upon addition of water into the dioxane.

In another example, a multiresonant sensor system may be built with four resonant frequencies. The 1,4-dioxane can be used as a model chemical for oil, because its dielectric constant is somewhat similar to oil and it is miscible with water. Water additions may be done to dioxane and measured with a sensor. Four example resonance spectra of the sensor are presented in FIGS. 18A and 18B. These values illustrate that the dispersion profile of the sensor in non-contaminated dioxane (FIG. 18A) has changed its shape upon addition of water (FIG. 18B). Also, the widths and the magnitudes of the resonance peaks have been modified by water addition.

Figure 19:
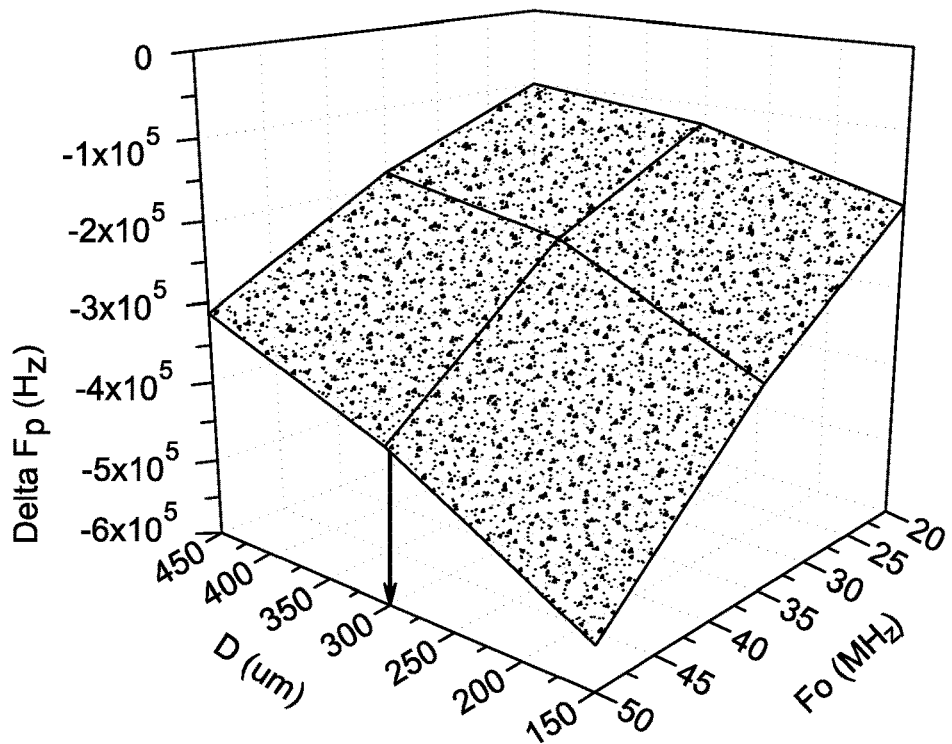
FIG. 19 is plot of effects of sensor design on sensitivity of Fp measurements.
Figure 20:
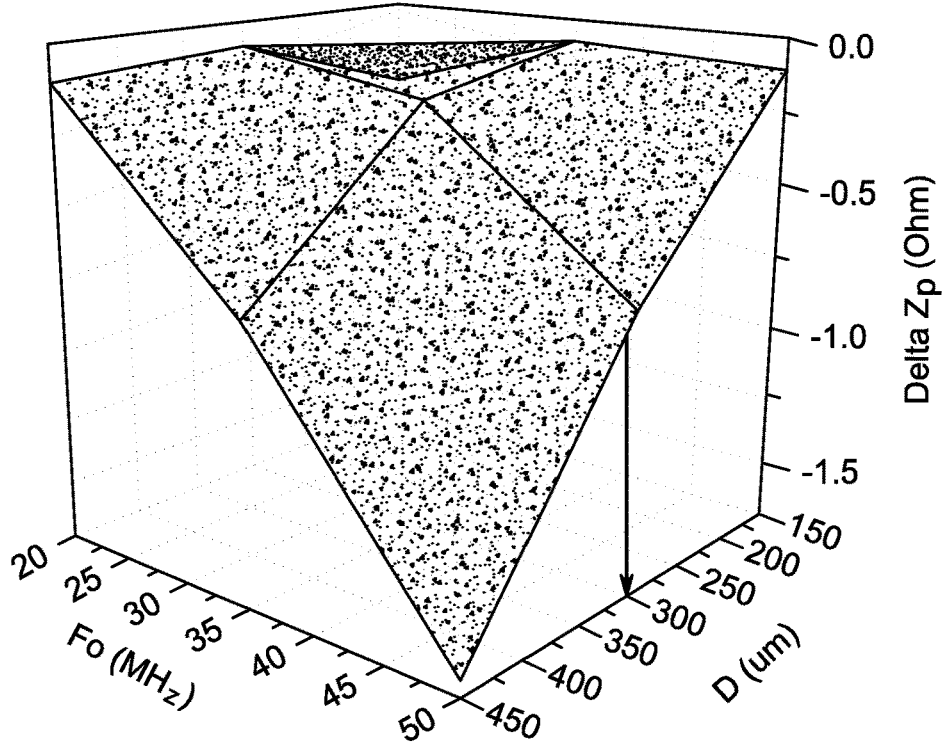
FIG. 20 displays effects of sensor design on sensitivity of Zp measurements.

In another example, sensor electrode geometries and resonant frequency may be optimized for the maximum Fp and Zp responses to water. A two-factor design of experiments may be done by varying interdigital electrode (IDE) spacing D and electrode width W, where D=W=150, 300, 450 micrometers (μm) and varying resonance frequency, Fp, as Fp=20, 35, 50 MHz (in air). Measurements may be performed by adding water to dioxane at 5000 ppm concentration. FIG. 19 shows effects of sensor design on sensitivity of Fp measurements. FIG. 20 shows effects of sensor design on sensitivity of Zp measurements. A 300 um IDE spacing and 50 MHz operation frequency yielded both strong Fp and Zp signals.

Figure 21:
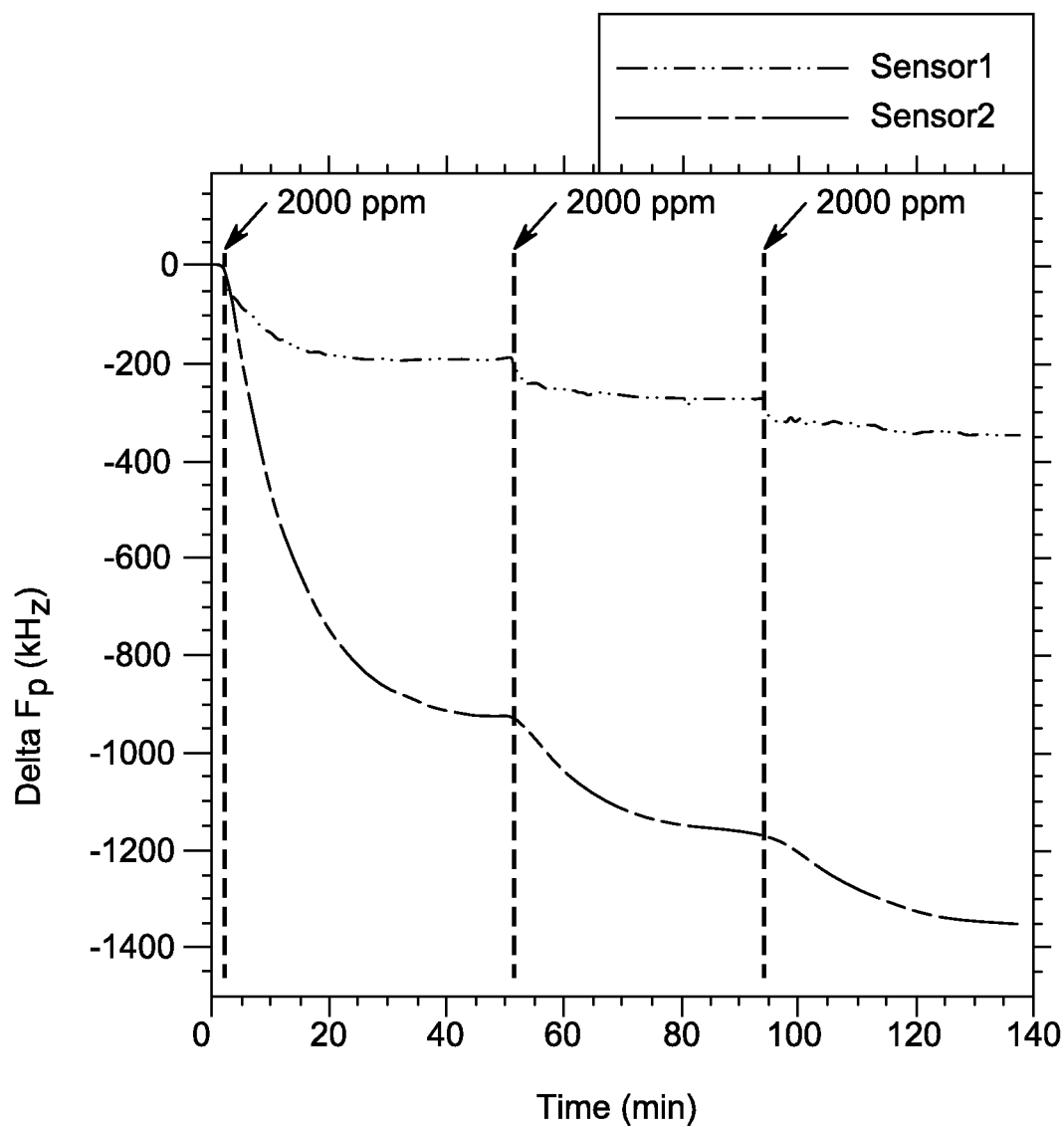
FIG. 21 is plot of results of measurements of water in oil with two multivariable resonant sensors.

In another example shown in FIG. 21, determination of water in oil may be performed by circulating oil in a test loop and adding water at 2000 ppm increments to generate water concentrations in oil of 2000 ppm, 4000 ppm, and 6000 ppm. Measurements may be performed using two resonant sensors. Sensor 1 had area of 2 cm² with the electrode width/spacing of 0.4 mm/0.4 mm and resonating at 80 MHz in air. Sensor 2 may be one of geometries from the design of experiments and had area of 4 cm² with the electrode width/spacing of 0.15 mm/0.15 mm and resonating at ~50 MHz in air. The limit of detection of water in oil may be determined at the signal-to-noise level of three to be 3-12 ppm (Sensor 1) and 0.6-2.6 ppm (Sensor 2) based on the measured sensor noise levels and signal levels at 2000 ppm of added water.

Figure 22:
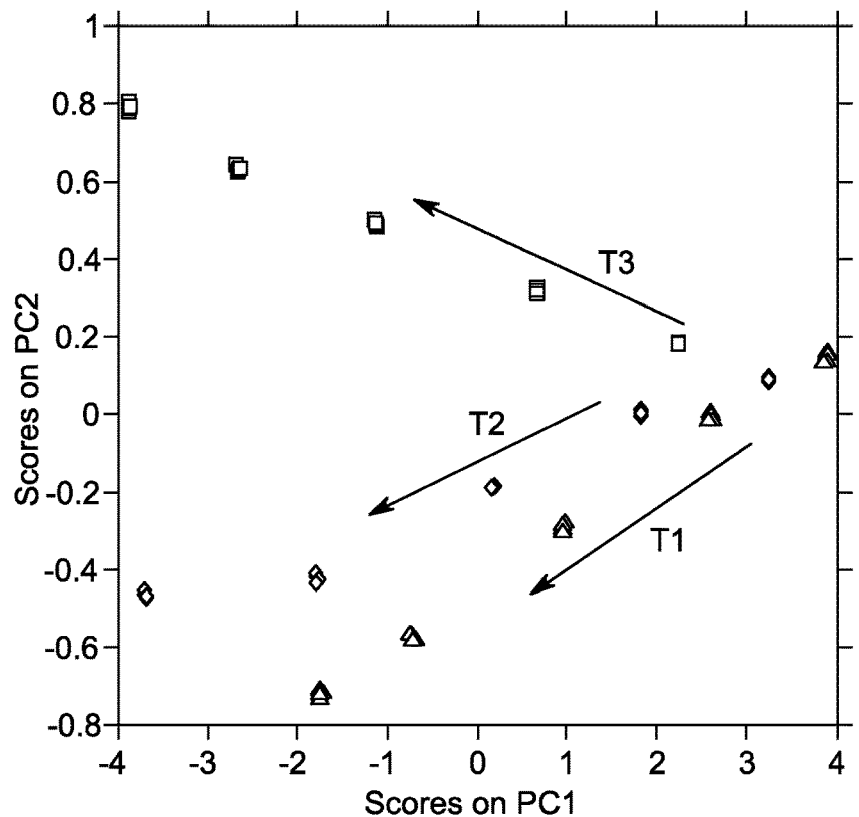
FIG. 22 is a scores plot of a developed PCA model of responses of the resonant sensor to additions of water at different temperatures, showing different response directions.
Figure 23:
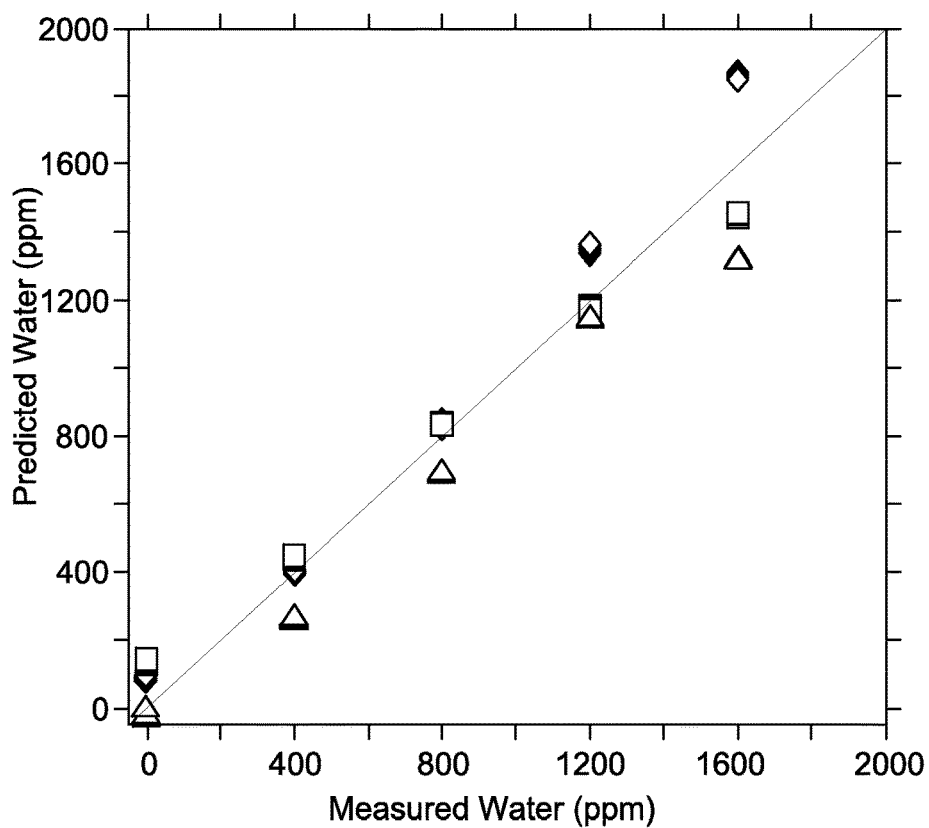
FIG. 23 is plot of results of multivariate linear regression model using partial least squares technique to quantify water concentrations in oil using responses of the single sensor.

In another example, determination of water in oil at different oil temperatures may be performed by circulating oil in a test loop and adding water at 400 ppm increments to generate water concentrations in oil of 400 ppm, 800 ppm, 1200 ppm, and 1600 ppm. The nominal temperatures of oil may be T1=80 degrees Celsius, T2=100 degrees Celsius, and T3=120 degrees Celsius as produced by a thermal bath. FIG. 22 depicts a scores plot of a developed PCA model illustrating that responses of the resonant sensor to additions of water at different temperature may be in different directions. Each individual arrow in FIG. 21 points in the direction of increasing water concentrations at oil temperatures T1, T2, and T3. FIG. 23 may depict results of multivariate linear regression model using partial least squares (PLS) technique to quantify water concentrations in oil using responses of the single sensor. The PLS technique may determine correlations between the independent variables and the sensor response by finding the direction in the multidimensional space of the sensor response that explains the maximum variance for the independent variables. FIG. 24 shows that such multivariate linear regression may be able to predict water concentrations independent of oil temperature.

Figure 24A:
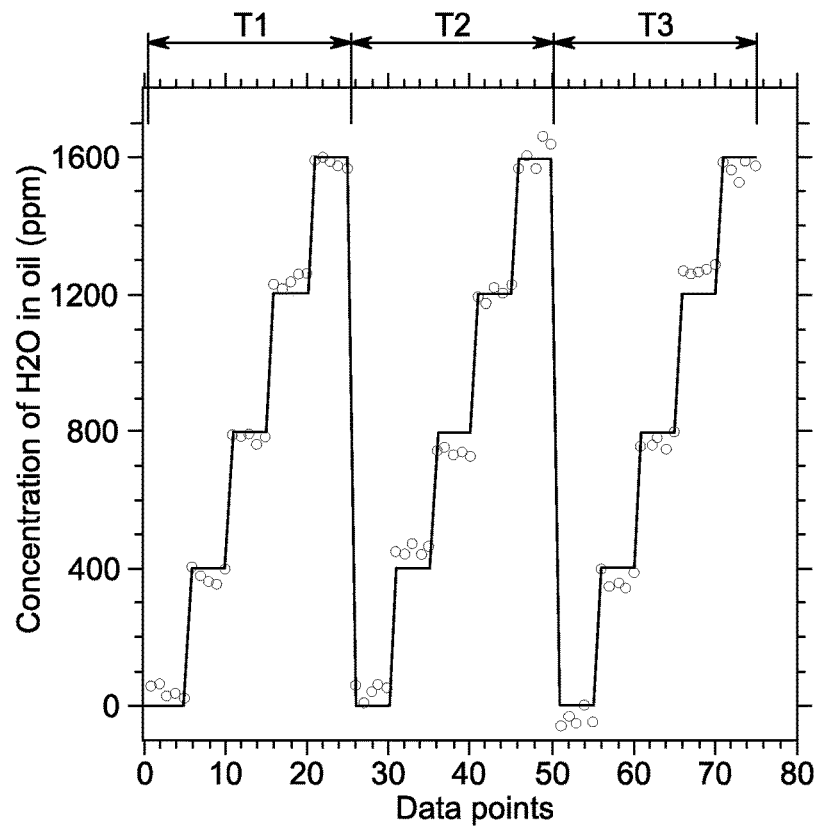
FIG. 24A is a plot of the actual (measured) concentrations of water in oil over time at three temperatures (solid line) and predicted concentrations (open circles)
Figure 24B:
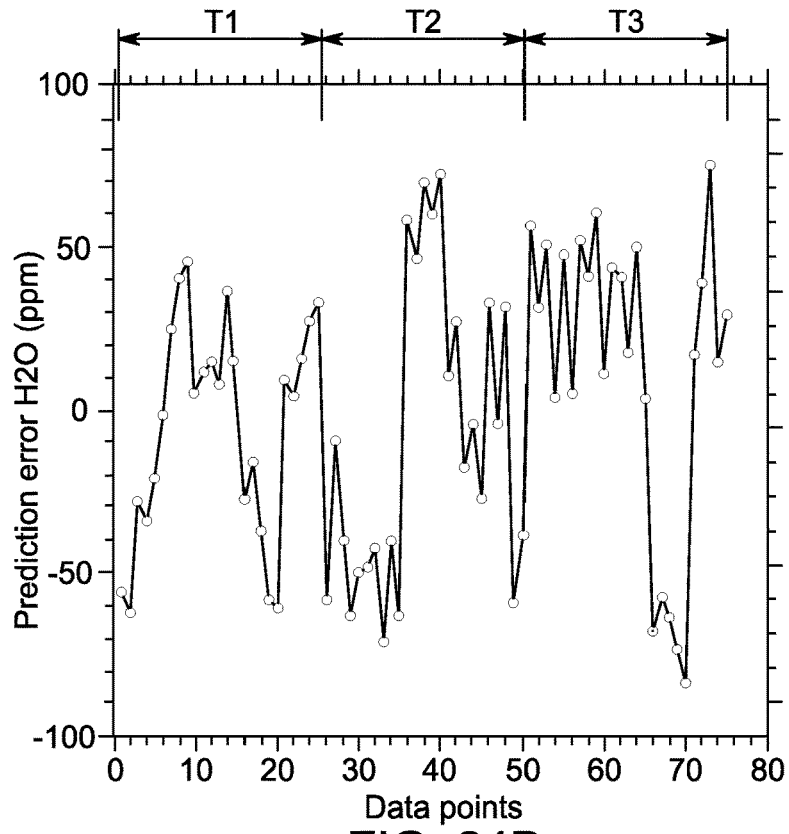
FIG. 24B is a plot of prediction error between actual and predicted concentrations of water in oil over time at three temperatures.
Figure 24C:
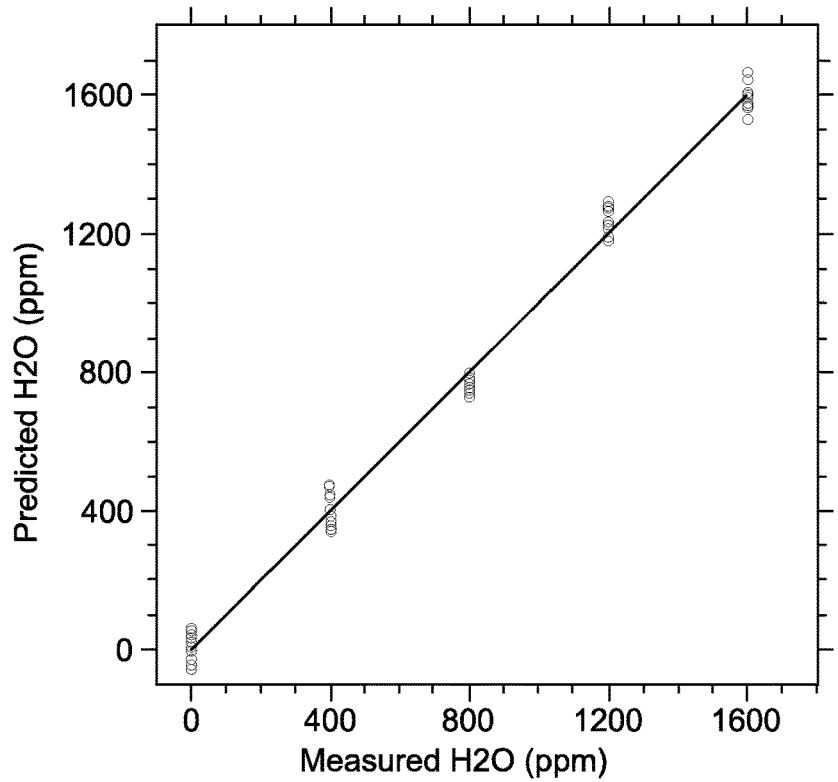
FIG. 24C is a plot of correlation between actual (measured) and predicted concentrations of water in oil at three temperatures.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be performed using a multivariate non-linear (quadratic) regression. FIG. 24A depicts the actual (measured) concentrations of water in oil at three temperatures (solid line) and predicted concentrations (open circles). FIG. 24B depicts prediction error between actual and predicted concentrations of water in oil at three temperatures. FIG. 24C depicts correlation plot between actual (measured) and predicted concentrations of water in oil at three temperatures.

Figure 25A:
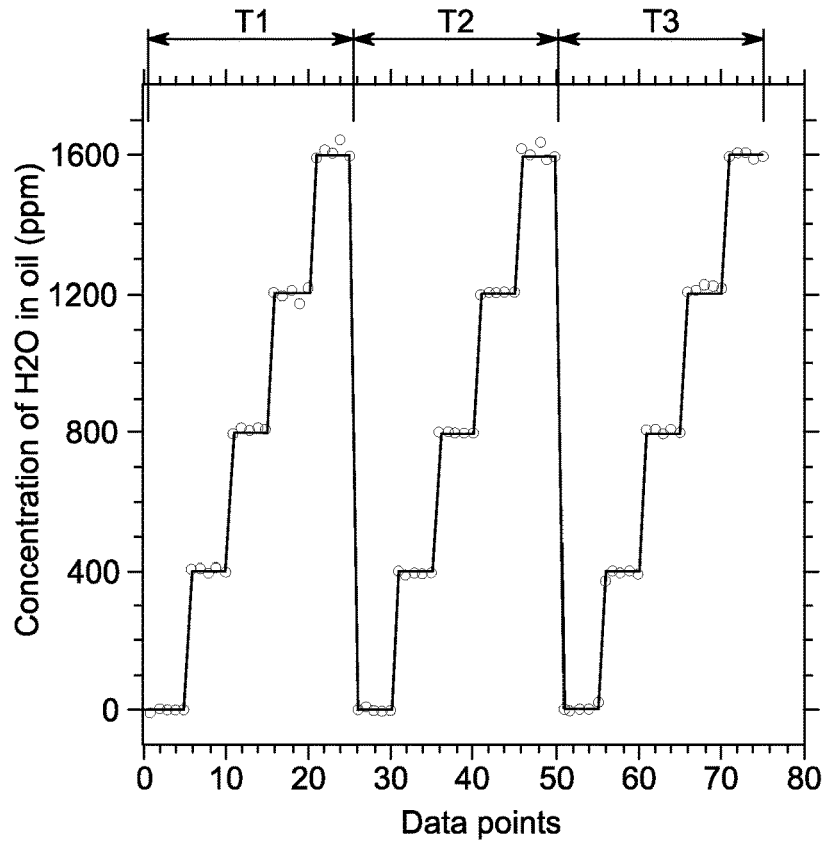
FIG. 25A is a plot of the actual (measured) concentrations of water in oil over time at three temperatures (solid line) and predicted concentrations (open circles) using responses of a multivariable resonant sensor and oil temperature sensor.
Figure 25B:
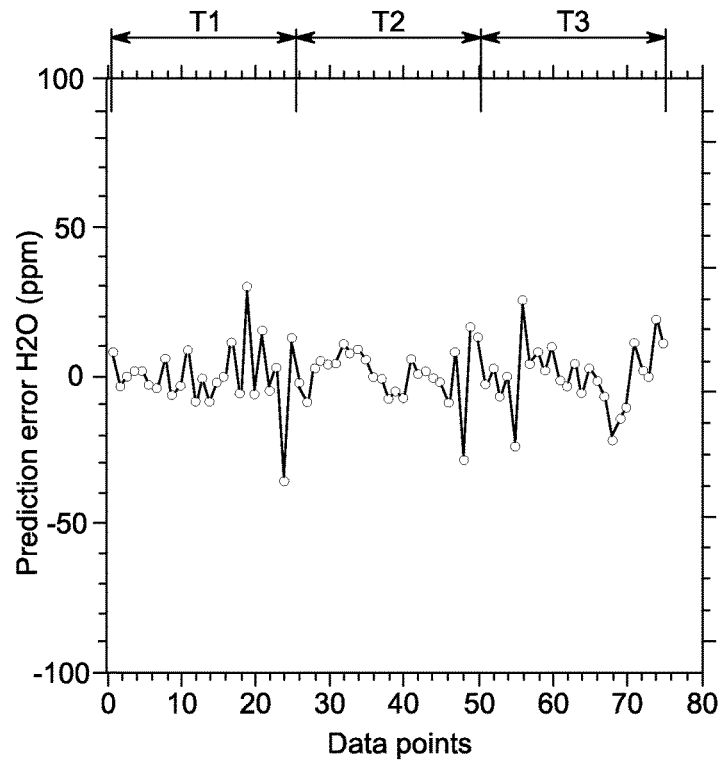
FIG. 25B is a plot of prediction error between actual and predicted concentrations of water in oil over time at three temperatures using responses of a multivariable resonant sensor and oil temperature sensor.
Figure 25C:
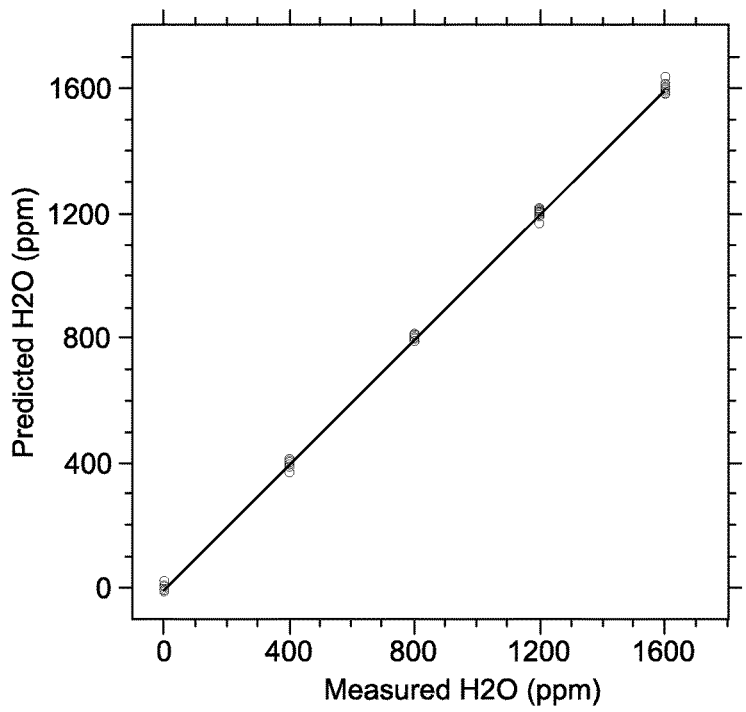
FIG. 25C is a plot of correlation between actual (measured) and predicted concentrations of water in oil at three temperatures using responses of a multivariable resonant sensor and oil temperature sensor.

Analysis of this sensor data of determination of water in oil (0 ppm, 400 ppm, 800 ppm, 1200 ppm, and 1600 ppm) at different nominal temperatures of oil (80 degrees Celsius, 100 degrees Celsius, and 120 degrees Celsius) may be further performed using a multivariate non-linear (quadratic) regression with an additional input from a temperature sensor positioned in measured oil. FIG. 25A depicts the actual (measured) concentrations of water in oil at three temperatures (solid line) and predicted concentrations (open circles). FIG. 25B depicts prediction error between actual and predicted concentrations of water in oil at three temperatures. FIG. 25C depicts correlation plot between actual (measured) and predicted concentrations of water in oil at three temperatures.

Figure 26:
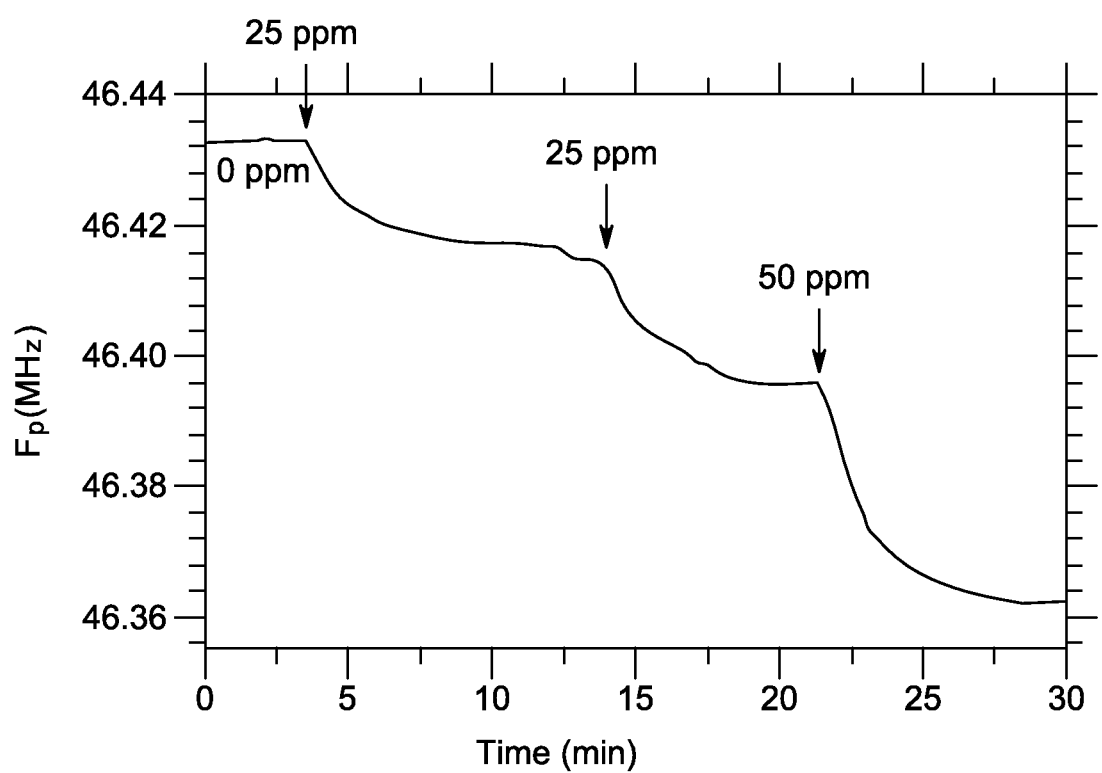
FIG. 26 is a response of the developed resonant sensor to water leaks into engine oil at levels of 25, 25, and 50 ppm each.

One of the developed multivariable sensors having an area of 4 cm² with the electrode width/spacing of 0.15 mm/0.15 mm and resonating at ~50 MHz in air may measure low concentration water leaks in oil. FIG. 26 depicts response of this developed resonant sensor to water leaks into engine oil at levels of 25 ppm, 25 ppm, and 50 ppm each. The data in this figure illustrates that this sensor may detect the water leaks at least a lowest tested level of 25 ppm with high signal-to-noise quality.

Figure 27A:
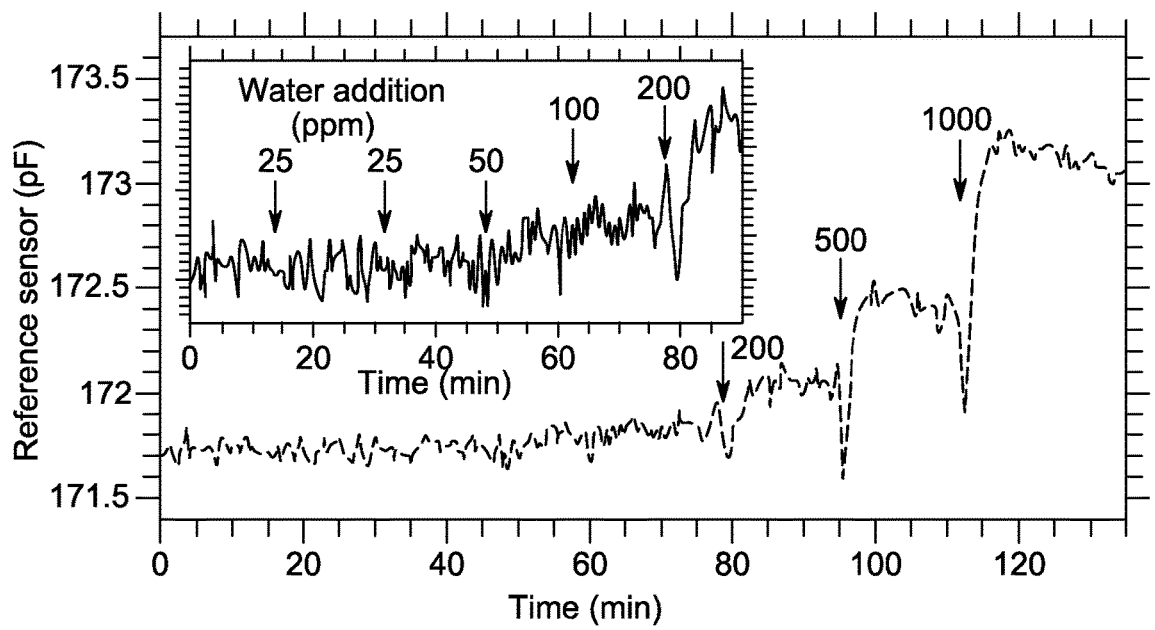
FIG. 27A is a response of a reference capacitance sensor to water leaks into engine oil at levels of 25, 25, 50, 100, 200, 500, and 1000 ppm each. Inset shows response to initial water leaks.
Figure 27B:
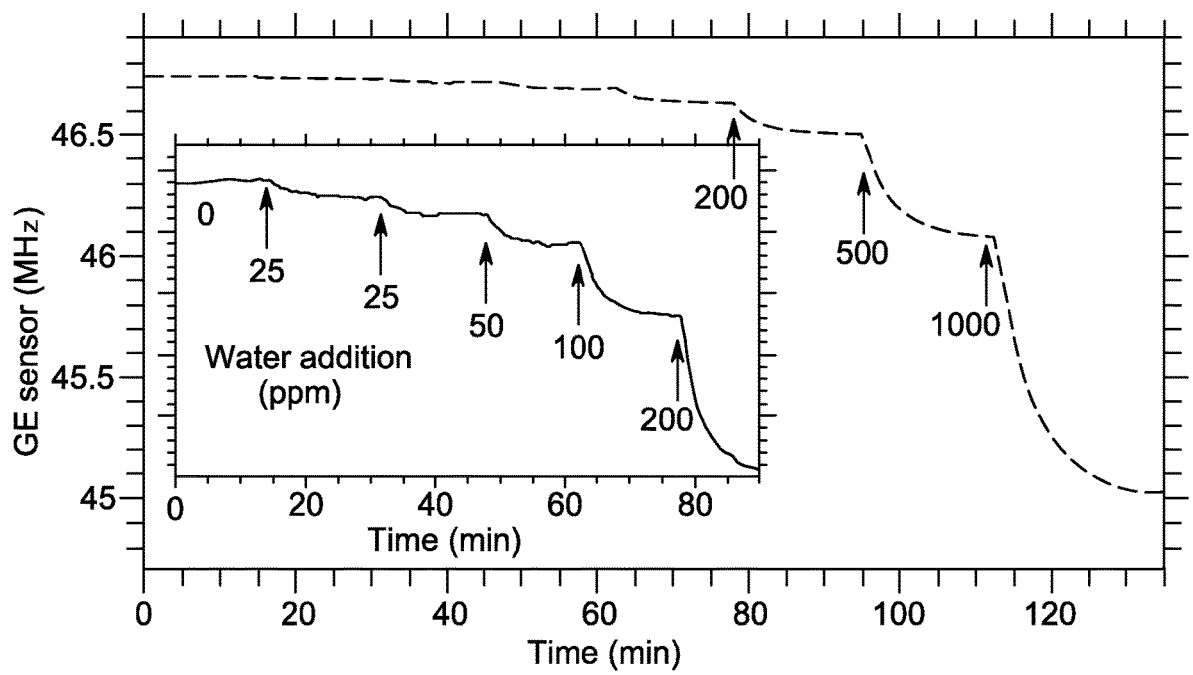
FIG. 27B is a response of a developed resonant sensor to water leaks into engine oil at levels of 25, 25, 50, 100, 200, 500, and 1000 ppm each. Inset shows response to initial water leaks.

The performance of this developed resonant sensor may compare with the performance of a standard non-resonant capacitance sensor that served as a reference capacitance sensor. The comparison may be performed by having both sensors in the same circulating-oil loop where water leaks may be introduced and presented to both sensors. Water leaks levels may be 25, 25, 50, 100, 200, 500, and 1000 ppm. FIG. 27A depicts the response of a reference capacitance sensor to water leaks into engine oil at levels of 25, 25, 50, 100, 200, 500, and 1000 ppm each. This figure illustrates that the reference capacitance sensor did not show an appreciable signal change from its noise until water leaks of 25, 25, 50, 100, and 200 ppm 200 ppm may be introduced. In contrast, FIG. 27B shows the response of a resonant sensor according to an embodiment to water leaks into engine oil where this sensor may detect the smallest water leak at 25 ppm and detected all other water leaks presented to both sensors.

Figure 28A:
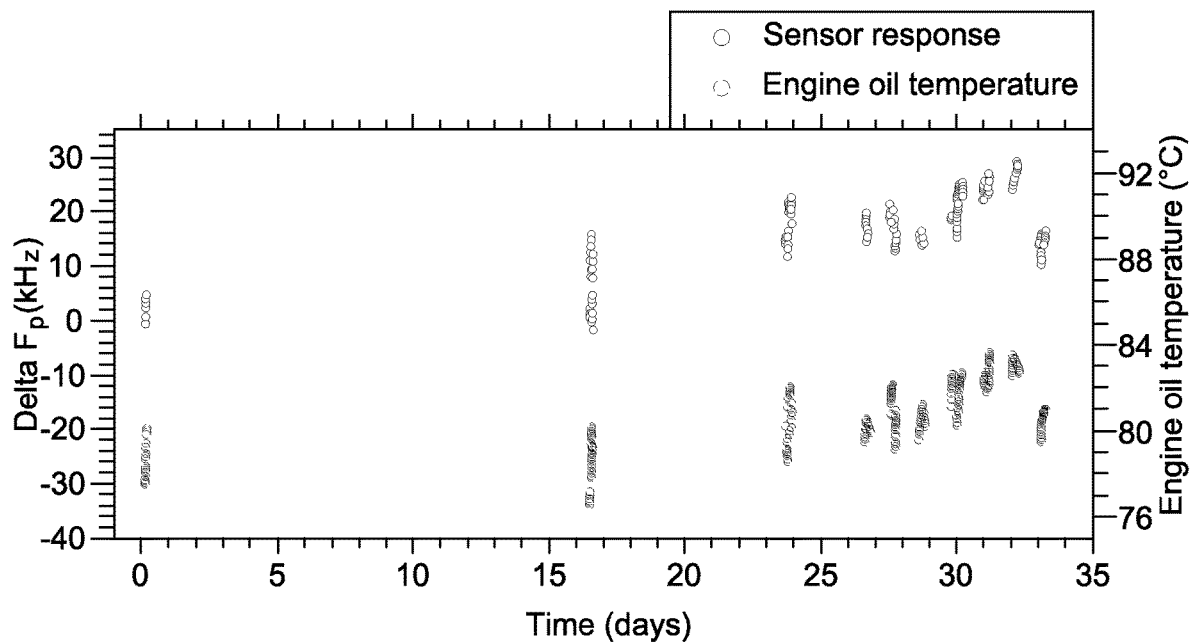
FIG. 28A shows operation of the developed resonant sensor in a single cylinder locomotive engine for ~34 days. Shown is temperature of oil and sensor response.
Figure 28B:
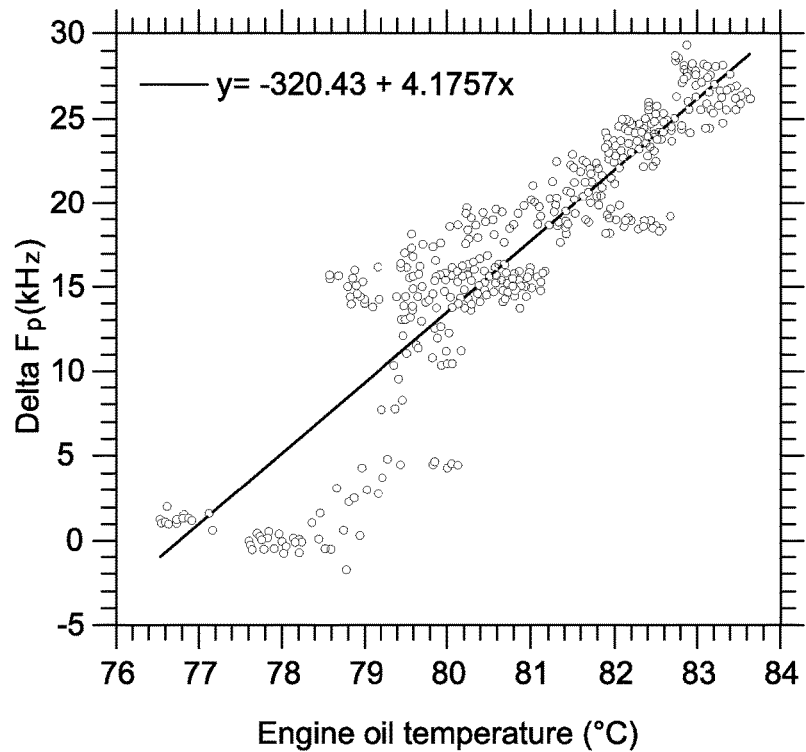
FIG. 28B shows correlation between response of the developed resonant sensor in a single cylinder locomotive engine for ~34 days and the temperature of oil.

This resonant sensor may be tested in a single cylinder locomotive engine test bed for about 34 days. FIG. 28A may depict results of operation of the developed resonant sensor in a single cylinder locomotive engine for temperature of oil and sensor response. FIG. 28B illustrates correlation between response of the developed resonant sensor in a single cylinder locomotive engine for about 34 days and the temperature of oil.

In another example, sources of leaks in engine may be determined by identifying dynamic signatures of the leaks, relating the identified signature with the known leak signature from a specific engine component, and determining the location of the leak based on the signature. Such approach may provide the ability for proactive maintenance, may replace the reactive maintenance, and may increase the time-in-use for assets having lubrication systems or with an internal combustion engine.

Figure 29:
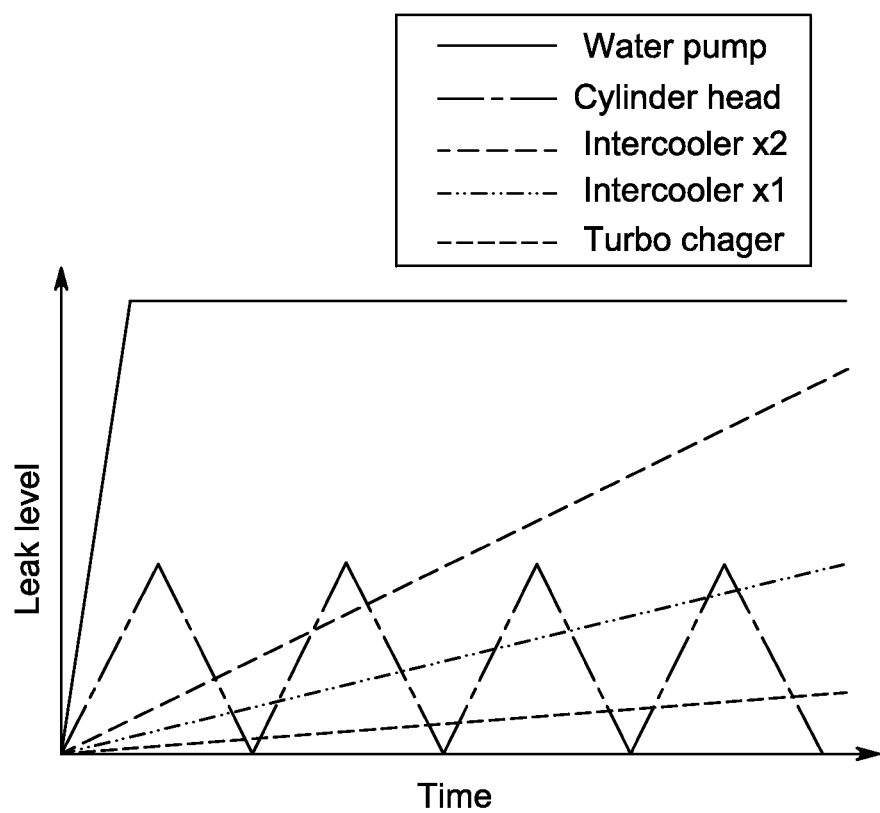
FIG. 29 is a schematic of dynamic signatures of leaks in typical components in an internal combustion engine.

Non-limiting examples of such assets with internal combustion engines include various vehicle types, each having its own set of operating parameters. Embodiments disclosed herein may provide a prognostics sensor tool for early determination of leaking components via dynamic leak signatures. These sensors may be applied in multiple locations in the engine to pinpoint the origin of leak. FIG. 29 depicts a schematic of dynamic signatures of leaks of a turbo charger (1-2 turbo chargers per engine), an intercooler (2 intercoolers per engine), a water pump (1 water pump per engine), and a cylinder head (12-16 cylinder heads per engine).

Technical effects may include a technique for assessing fluid health, such as the health of engine oil. Such techniques may determine if the fluid may be contaminated or needs to be replaced, which provides service and overall process benefits, such as improved engine health in the case of fluids in use in engines.

This written description uses examples to disclose the invention, and to enable one of ordinary skill in the relevant art to practice embodiments of the invention, including making and using the devices or systems and performing the methods. The patentable scope of the invention is defined by the claims, and may include other examples that occur to one of ordinary skill in the relevant art. Such other examples are intended to be within the scope of the claims if they have structural elements that do not differ from the literal language of the claims, or if they include equivalent structural elements with insubstantial differences from the language of the claims.

The invention claimed is:

1. A system, comprising:
    a sensor comprising:
        a resonant inductor-capacitor-resistor (LCR) circuit; and
        a sensing region comprising:
            at least the inductor of the LCR circuit:
            at least two electrodes electrically coupled to the LCR circuit, wherein the at least two electrodes are configured to be placed in operational contact with a fluid of interest without the inductor being placed in operational contact with the fluid of interest; and
            a memory chip coupled to the LCR circuit and configured to be placed in operational contact with the fluid of interest, the memory chip further configured to store information corresponding to the sensor;
    a sensor reader; and
    a controller configured to communicate wirelessly with the sensor and including data processing circuitry and memory storing routines to:
        wirelessly receive an electrical signal from the sensor, wherein the signal includes resonant impedance spectra of the sensing region in operational contact with the fluid over a measured spectral frequency range;
        analyze the resonant impedance spectra; and
        determine one or more properties of the fluid based on the analyzed resonant impedance spectra.

2. The system of claim 1, wherein the operational contact is direct contact with the fluid.

3. The system of claim 1, further comprising a dielectric protective layer configured to separate the sensing region from direct contact with the fluid while maintaining operational contact of the sensing region with the fluid.

4. The system of claim 1, wherein the sensing region comprises a sensing material, and wherein the sensing material is a dielectric and is chemically inert to, or chemically resistant to degradation by, the fluid at a temperature in a range of from about 1 degrees Celsius up to about 260 degrees Celsius.

5. The system of claim 1, wherein the sensing region comprises a sensing material, and wherein the sensing material is a dielectric and is chemically inert or resistant to the fluid at a temperature in a range of from about zero degrees Celsius down to about negative 260 degrees Celsius.

6. The system of claim 1, wherein the controller is configured to determine the properties of the fluid by identifying one or more components based on a characteristic change in resonance parameters associated with the one or more components, the resonance parameters determined from the resonant impedance spectra.

7. The system of claim 1, wherein the controller is configured to determine the properties of the fluid by quantifying one or more components based on a characteristic change in resonance parameters associated with the one or more components, the resonance parameters determined from the resonant impedance spectra.

8. The system of claim 7, wherein the one or more components comprise one or more of water, soot, wear products, or hydrocarbon.

9. The system of claim 1, wherein the fluid comprises one or more of oil, water, solvent, mixture of solvents, or fuel, and wherein the measured spectral frequency range comprises a resonant frequency of the resonant LCR circuit and/or a range of frequencies around the resonant frequency.

10. The system of claim 1, wherein the sensor is a passive RFID sensor.

11. The system of claim 1, wherein the controller is configured to analyze the resonant impedance spectra by analyzing at least four spectral parameters of each resonant impedance spectrum.

12. The system of claim 11, wherein the controller is configured to analyze the resonant impedance spectra further by analyzing at least one or more additional spectral parameters including Fp, Zp, F1, Z1, F2, or Z2, where Fp is a frequency of a maximum of a real part of each respective resonant impedance spectrum, Zp is a magnitude of the real part of each respective resonant impedance spectrum, F1 is a resonant frequency of an imaginary part of each respective resonant impedance spectrum, Z1 is a magnitude of the resonant frequency of the imaginary part of each respective resonant impedance spectrum, F2 is an anti-resonant frequency of the imaginary part of each respective resonant impedance spectrum, and Z2 is a magnitude of the anti-resonant frequency of the imaginary part of each respective resonant impedance spectrum.

13. The system of claim 1, wherein the LCR circuit is a first LCR circuit, and further comprising one or more additional LCR circuits and one or more tuning components coupled to respective LCR circuits that are configured to couple or isolate each respective LCR circuit to the sensing region based on a tuning input, where each LCR circuit has a different resonant frequency.

14. The system of claim 13, wherein the tuning input is based on a desired frequency range of the sensor, and wherein the desired frequency range includes frequencies of 100 MHz or greater.

15. The system of claim 13, wherein the tuning components comprise one or more variable inductors or capacitors.

16. The system of claim 13, further comprising a thermal element in thermal contact with the sensing region of the sensor and configured to supply at least one of a local heating or a local cooling adjacent to the sensing region.

17. The system of claim 1, wherein the controller is further configured to analyze resonant impedance spectra of the sensor based on the signal, and determine one or more properties of the fluid based on the analyzed resonant impedance spectra.

18. The system of claim 1, wherein the sensor operates at a frequency determined at least in part by an operating frequency used by the memory chip.

19. A method, comprising:
    wirelessly exciting, by a controller configured to communicate wirelessly with a sensor, the sensor in contact with a fluid, wherein the sensor comprises a sensing region with an LCR resonant circuit that is not in operational contact with the fluid, a memory chip coupled to the LCR resonant circuit and configured to be placed in operational contact with the fluid and to store data corresponding to the sensor, and at least two electrodes electrically coupled to the LCR resonant circuit, wherein the at least two electrodes are in operational contact with the fluid and operate at two or more resonant frequencies in a frequency range of analysis;
    wirelessly receiving, by the controller, a signal from the sensor across the frequency range of analysis, wherein the signal includes a resonant impedance spectra of the fluid; and
    determining, by the controller, two or more properties of the fluid based at least in part on the resonant impedance spectra.

20. The method of claim 19, wherein the fluid is oil, wherein determining the two or more properties of the fluid based at least in part on the resonant impedance spectra comprises determining a concentration of fuel and a concentration of water in the oil based at least in part on the resonant impedance spectra, and further comprising determining, by the controller, dynamic signatures relating to changes of chemical constituents in the fluid over time or under determined conditions based at least in part on the resonant impedance spectra.

21. The method of claim 19, further comprising responding, by the controller, to a change in one or both of a temperature and a complex permittivity of the fluid by obtaining one or more signatures of the fluid based at least in part on the resonant impedance spectra of the fluid at one or both of a fluid temperature and a fluid complex permittivity.

22. A system, comprising:
a resonant sensor configured to sense a complex permittivity of a fluid in operational contact with a sensing region including a memory chip configured to be placed in operational contact with the fluid and to store information corresponding to the sensor, the sensing region further including at least two electrodes coupled to the memory chip and to an inductor-capacitor-resistor (LCR) circuit of the sensor that is not in contact with the fluid, wherein the at least two electrodes are in operational contact with the fluid; and a controller configured to communicate wirelessly the sensor and including data processing circuitry and memory storing routines to:
  wirelessly receive an electrical signal from the sensor, wherein the signal includes resonant impedance spectra of the fluid over a measured spectral frequency range;
  determine a complex permittivity of the fluid based at least in part on the resonant impedance spectra;
  determine dynamic signatures relating to changes of chemical constituents in the fluid over time or under determined conditions based on the determined complex permittivity over time; and
  identify a source of a leak in an engine based on the dynamic signatures.

23. The system of claim 22, wherein the inductor of the LCR circuit is configured to be placed in operational contact with the fluid.

* * * * *